(12) United States Patent
Banville et al.

(10) Patent No.: US 6,414,179 B1
(45) Date of Patent: Jul. 2, 2002

(54) ALPHA-AND BETA-SUBSTITUTED TRIFLUOROMETHYL KETONES AS PHOSPHOLIPASE INHIBITORS

(75) Inventors: Jacques Banville, St-Hubert; Anne Marinier, Kirkland, both of (CA); Yonghua Gai, Killingworth, CT (US); Serge Plamondon, Ste-Catherine; Stephan Roy, St-Lambert, both of (CA); Neelakantan Balasubramanian, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/816,574

(22) Filed: Mar. 23, 2001

Related U.S. Application Data

(63) Continuation-in-part of application No. 09/780,554, filed on Feb. 9, 2001, now abandoned.
(60) Provisional application No. 60/186,107, filed on Mar. 1, 2000, and provisional application No. 60/183,521, filed on Feb. 18, 2000.

(51) Int. Cl.⁷ .......................................... C07C 261/00
(52) U.S. Cl. ........................ 560/30; 560/60; 562/426; 564/317; 568/325; 568/308; 514/672
(58) Field of Search ................ 514/678; 562/426; 564/317; 568/308, 325; 560/30, 60

(56) References Cited

U.S. PATENT DOCUMENTS

| 5,453,443 A | 9/1995 | Perrier et al. ............. 514/570 |
| 5,866,318 A | 2/1999 | Rydel et al. ............... 435/4 |

FOREIGN PATENT DOCUMENTS

| EP | 369657 | * 4/1999 | ............ C12Q/1/44 |
| JP | 10-067754 | * 3/1998 | ........ C07D/239/46 |
| WO | WO 97/21676 | 6/1997 | |
| WO | WO 98/08818 | 3/1998 | |
| WO | WO 98/25893 | 6/1998 | |
| WO | WO 99/15129 | 4/1999 | |

OTHER PUBLICATIONS

I. P. Street, et al, "Slow–and Tight–Binding Inhibitors of the 85–kDa Human Phospholipase $A_2$," Biochemistry, 32, pp. 5935–5940, 1993.

K. M. Abdullah, et al, "Synthesis and Preparation of an Affinity Chromatography col. for the Purification of Cytosolic Phospholipase $A_2$," Bioorganic & Medicinal Chemistry Letters, 5(5), pp. 519–522, 1995.

D. L. Boger, et al, "Trifluoromethyl Ketone Inhibitors of Fatty Acid Amide Hydrolase: A Probe of Structural and Conformational Features Contributing to Inhibition," Bioorganic & Medicinal Chemistry Letters, 9, pp. 265–270, 1999.

P. Norman, "Medicinal Chemistry in Eastern England–Ninth Symposium," Idrugs, 1(1), pp. 49–54, 1998.

* cited by examiner

*Primary Examiner*—Paul J. Killos
(74) *Attorney, Agent, or Firm*—David M. Morse

(57) ABSTRACT

Inhibitors of the cytosolic phospholipase A2 enzymes are provided which are of use in controlling a wide variety of inflammatory diseases. The inhibitors of the present invention have the general formula

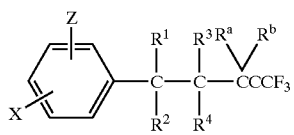

where X, Z, $R^1$, $R^2$, $R^3$, $R^4$, $R^a$ and $R^b$ are as defined in the specification.

9 Claims, No Drawings

ALPHA-AND BETA-SUBSTITUTED TRIFLUOROMETHYL KETONES AS PHOSPHOLIPASE INHIBITORS

CROSS-REFERENCE TO RELATED APPLICATIONS

This application is a Continuation-in-Part of U.S. Ser. No. 09/780,554 filed Feb. 9, 2001 now abandoned which claims the benefit of U.S. Provisional Application Ser. No. 60/186,107 filed Mar. 1, 2000 and No. 60/183,521 filed Feb. 18, 2000.

BACKGROUND OF THE INVENTION

I. Field of the Invention

The present invention relates to certain alpha- and/or beta-substituted trifluoromethylketone compounds, their salts, hydrates and derivatives thereof, a process for their preparation, intermediates useful in their preparation, pharmaceutical compositions containing them and such ketone compounds as inhibitors of phospholipase $A_2$ enzymes that are involved in the human inflammatory diseases and are thus useful agents in the treatment of inflammatory diseases such as asthma, arthritis, inflammatory bowel disease and neurodegenerative diseases.

II. Background of the Invention and Description of the Prior Art

Inflammatory diseases of the skin, such as psoriasis and atopic dermatitis, afflict greater than 5% of the population. And the inflammatory disease such as asthma affects more than 10 million people in US alone. Currently, the treatment of these disorders typically involves the use of topical and inhalation of coticosteroids and bronchodilators. However, these agents also have undesirable side effects such as skin atrophy which limit the duration of therapy. In addition, topical application of a drug is difficult for many patients where the affected area may be very large.

Phospholipase $A_2$ ($PLA_2$) is the common name for phosphatide 2-acylhydrolase which catalyzes the hydrolysis of the sn-2-acyl ester bond of phosphoglycerides and results in production of lysophospholipids and free fatty acids. When the fatty acid is arachidonic acid, further action by cyclooxygenase and 5-lipoxygenase enzymes results in eicosanoid production, which is implicated in inflammation, and leukotrienes which are linked to asthma. Lysophophospholipid metabolism results in production of platelet activating factor and both lysophospholipids and platelet activating factor also play a role in inflammation.

$PLA_2$ enzymes exist as secreted forms (MW~12,000–15,000) and cytosolic forms (MW~85,000). The cytosolic or $cPLA_2$ enzymes appear to play a key role in the pathway leading to the formation of platelet activating factor and the eicosanoids.

Inappropriate activation of the cytosolic $PLA_2$ enzymes, therefore, can result in a variety of chronic and acute conditions including asthma, cerebral ischemia [Clemens et al., *Stroke*, 1996, 27: 527–535], Alzheimer's Disease [Stephenson et al., *Neurobiology of Stroke*, 1996, 3: 51–63 and see also U.S. Pat. No. 5,478,857], rheumatoid arthritis, neutrophil and platelet activation [Huang et al., *Mediators of Inflammation*, 1994, 3: 307–308], chronic skin inflammation and damage to the skin resulting from exposure to ultraviolet light [Gresham et al., *American Journal of Physiology*, 1996, 270; *Cell Physiology*, 39:C1037–C1050] and macrophage activation [Balsinde et al., *Journal of Biological Chemistry*, 1996, 271: 6758–6765].

Inhibitors of the $cPLA_2$ enzymes may, therefore, be of use in controlling a wide variety of inflammatory diseases. The literature describes a significant number of compounds said to be phospholipase $A_2$ inhibitors.

*Biochemistry*, 1993, 32: 5935–5940, discloses a trifluoromethyl ketone analog of arachidonic acid having the formula

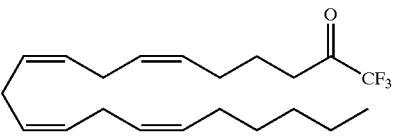

as a selective inhibitor of $cPLA_2$.

*Bioorganic Med. Chem. Lett.*, 1995, 5: 519–522, discloses selective $cPLA_2$ inhibitors of the formula

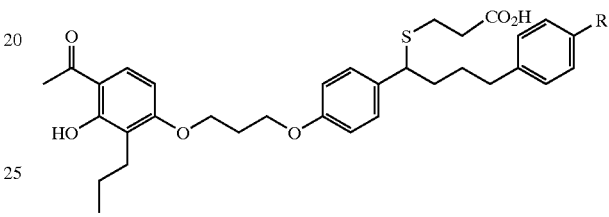

where R is either H or OH.

Japanese published Patent Application JP09268153A (Derwent No. 97-554679/51) discloses $cPLA_2$ inhibitors of the formula $RCOCF_3$ where RCO is an acyl residue of an n-3 series highly unsaturated fatty acid. The compounds are said to be useful as antiinflammatory or antiallergic drugs.

Certain trifluoromethylketone have been disclosed as inhibitors of fatty acid amide hydrolase in *Bioorg. & Med. Chem. Lett.*, 1999, 9: 265–270.

Published Application WO 98/25893 discloses arylsulfonamide compounds of the general formula

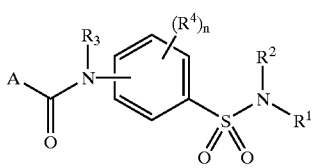

wherein:
  A represents a $C_4$–$C_{10}$ alkyl group, an aryl group, an arylalkyl group, radicals selected from the group consisting of —CH=CH—B, —O—B, —S—B, and —NH—B, or radicals of formula —CH$_2$—X,
wherein:
  B represents a non-aromatic $C_3$–$C_8$ carbocycle, a $C_3$–$C_8$ alkyl group, a heterocycle or an arylalkyl group, each of which is optionally substituted with one or more members independently selected from the group consisting of a halogen atom, a $C_1$–$C_4$ alkyl group, a $C_1$–$C_4$ alkoxy group, cyano, nitro, a heterocycle, an aryl group and an aryloxy group, and
  X is a member selected from the group consisting of a halogen atom, —S-aryl, —S-heterocycle, and —PO$_3$R$_2$ wherein each R is independently selected from the group consisting of a hydrogen atom and $C_1$–$C_3$ alkyl;
  $R^1$ and $R^2$ each independently represent a hydrogen atom, a lower alkyl group, or a group represented by the formula: —$(CH_2)_q$—A' wherein q is an integer of 2 to 4, and A' is a member selected from the group consisting of a hydroxyl group, a group represented by the formula:

wherein $R^5$ and $R^6$ each independently represent a hydrogen atom, a lower alkyl group, or a group represented by the formula:

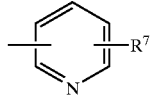

wherein $R^7$ represents a hydrogen atom, a lower alkyl group, or a group represented by the formula:

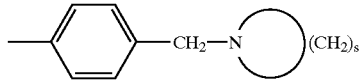

wherein s is an integer of 2 to 5; or $R^1$ and $R^2$ each independently represent an unsubstituted cycloalkyl group, or a cycloalkyl substituted with a lower alkyl or halogen or condensed with an aromatic ring, a bicycloalkyl, or tricycloalkyl, said bicycloalkyl or tricycloalkyl being an aliphatic saturated hydrocarbon group made of two or three rings, respectively, with at least two carbon atoms being common to each ring, or an azabicycloalkyl group which is a bicycloalkyl group as described above in which one carbon atom is replaced by a nitrogen atom or a group represented by the formula:

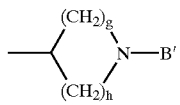

wherein g and h are each an integer of 1 to 4, and B' stands for a lower alkyl group, an arylalkyl group, an arylalkyl group substituted by lower alkyl; halogen or a lower alkoxy group, or a pyridylalkyl group, or a pyridylalkyl group substituted with a lower alkyl group, a halogen or a lower alkoxy group; or $R^1$ and $R^2$ may be combined together to form a 6- or 7-membered ring which may contain a nitrogen or oxygen atom in addition to the nitrogen atom to which $R^1$ and $R^2$ are bonded, and said 6- or 7-membered ring may be substituted with a lower alkyl, arylalkyl, cycloalkylalkyl or heteroarylalkyl group;

$R^3$ represents a hydrogen atom, a lower alkyl group, or a $C_3$-$C_8$ cycloalkyl group;

$R^4$ represents a hydrogen atom, a lower alkyl group, a lower alkoxy group or a halogen atom;

n is an integer of 1 to 4, provided that when n is 2, the two $R^4$ groups may form a cyclohexenyl or phenyl ring together with two adjacent carbon atoms constituting the benzene ring; and any pharmacologically acceptable salts thereof as inhibitors of phospholipase $A_2$ activity, particularly $cPLA_2$.

Published Application WO 98/08818 discloses Inhibitors of phospholipase enzymes of formulae I, II and III

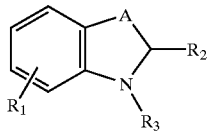

I

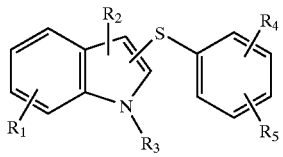

II

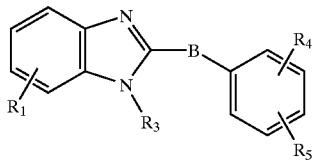

III or a pharmaceutically acceptable salt thereof, wherein:

A is independent of any other group and is selected from the group consisting of —$CH_2$— and —$CH_2$—$CH_2$—;

B is independent of any other group and is selected from the group consisting of —$(CH_2)_n$—, —$(CH_2O)_n$—, —$(CH_2S)_n$—, —$(OCH_2)_n$—, —$(SCH_2)_n$—, —$(CH=CH)_n$—, —$(C\equiv C)_n$—, —$CON(R_6)$—, —$N(R_6)CO$—, —$O$—, —$S$— and —$N(R_6)$—;

$R_1$ is independent of any other R group and is selected from the group consisting of —X—$R_6$, —H, —OH—, halogen, —CN, —$NO_2$, $C_1$-$C_5$ alkyl, alkenyl, alkinyl, aryl and substituted aryl;

$R_2$ is independent of any other R group and is selected from the group consisting of —H, —COOH, —$COR_5$, —$CONR_5R_6$, —$(CH_2)_n$—W—$(CH_2)_m$—Z—$R_5$, —$(CH_2)_n$—W—$R_5$, —Z—$R_5$, $C_1$-$C_{10}$ alkyl, alkenyl and substituted aryl;

$R_3$ is independent of any other R group and is selected from the group consisting of —H, —COOH, —$COR_5$, —$CONR_5R_6$, —$(CH_2)_n$—W—$(CH_2)_m$—Z—$R_5$, —$(CH_2)_n$—W—$R_5$, —Z—$R_5$, $C_1$-$C_{10}$ alkyl, alkenyl and substituted aryl;

$R_4$ is independent of any other R group and is selected from the group consisting of —H, —OH, $OR_6$, $SR_6$, —CN, —$COR_6$, —$NHR_6$, —COOH, —$CONR_6R_7$, —$NO_2$, —$CONHSO_2R_8$, $C_1$-$C_5$ alkyl, alkenyl and substituted aryl;

$R_5$ is independent of any other R group and is selected from the group consisting of —H, —OH, —$O(CH_2)_nR_6$, —$SR_6$, —CN, —$COR_6$, —$NHR_6$, —COOH, —$NO_2$, —COOH, —$CONR_6R_7$, —$CONHSO_2R_8$, $C_1$-$C_5$ alkyl, alkenyl, alkinyl, aryl substituted aryl, —$CF_3$, —$CF_2CF_3$ and

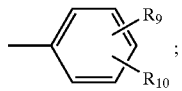

;

$R_6$ is independent of any other R group and is selected from the group consisting of —H, $C_1$-$C_5$ alkyl, alkenyl, alkinyl, aryl and substituted aryl;

$R_7$ is independent of any other R group and is selected from the group consisting of —H, $C_1$–$C_5$ alkyl, alkenyl, alkinyl, aryl and substituted aryl;

$R_8$ is independent of any other R group and is selected from the group consisting of $C_1$–$C_3$ alkyl, aryl and substituted aryl;

$R_9$ is independent of any other R group and is selected from the group consisting of —H, —OH, a halogen, —CN, —$OR_6$, —COOH, —$CONR_6R_7$, tetrazole, —$CONHSO_2R_8$, —$COR_6$, —$(CH_2)_nCH(OH)R_6$ and —$(CH_2)_nCHR_6R_5$;

$R_{10}$ is independent of any other R group and is selected from the group consisting of —H, —OH, a halogen, —CN, —$OR_6$, —COOH, —$CONR_6R_7$, tetrazole, —$CONHSO_2R_8$, —$COR_6$, —$(CH_2)_nCH(OH)R_6$ and —$(CH_2)_nCHR_6R_5$;

W is, independent each time used including within the same compound, selected from the group consisting of —O—, —S—, —$CH_2$—, —CH=CH—, —C≡C— and —$N(R_6)$—;

X is independent of any other group and is, independently each time used including within the same compound, selected from the group consisting of —O—, —S— and —$N(R_6)$—;

Z is independent of any other group and is, independently each time used including within the same compound, selected from the group consisting of —$CH_2$—, —O—, —S—, —$N(R_6)$—, —CO—, —$CON(R_6)$— and —$N(R_6)CO$—;

m is, independently each time used including within the same compound, an integer from 0 to 4; and n is independently of m and is, independently each time used including within the same compound, an integer from 0 to 4.

*Drugs*, 1998, 1(1): 49–50, discloses a limited series of $cPLA_2$ inhibitors as shown below

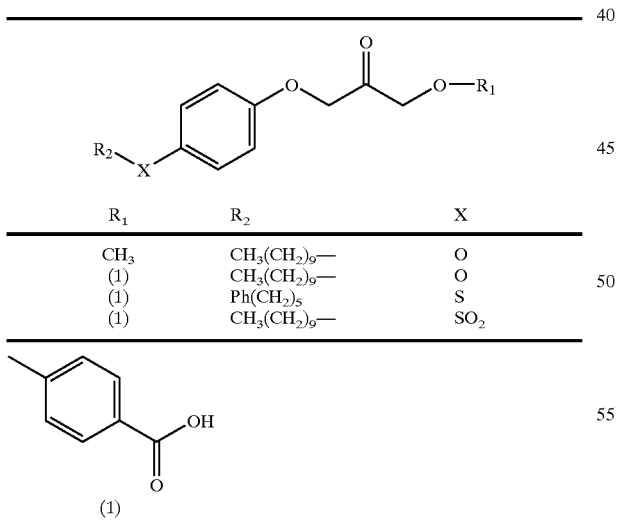

| $R_1$ | $R_2$ | X |
|---|---|---|
| $CH_3$ | $CH_3(CH_2)_9$— | O |
| (1) | $CH_3(CH_2)_9$— | O |
| (1) | $Ph(CH_2)_5$— | S |
| (1) | $CH_3(CH_2)_9$— | $SO_2$ |

U.S. Pat. No. 5,866,318 relates to methods for inhibiting cell death in mammalian cells, particularly in neuronal cells, by administering a suitable inhibitor of phospholipase $A_2$ activity, typically an inhibitor of $cPLA_2$.

Published Application WO 97/21676 discloses certain azetidinone compounds as phospholipase inhibitors in the treatment of atherosclerosis.

U.S. Pat. No. 5,453,443 discloses a series of biaryl ketones which are reported to inhibit $PLA_2$ enzymes. These compounds have the generic formula

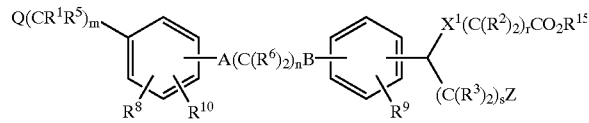

wherein:

$R^1$ is selected from
(a) hydrogen,
(b) —$C_{1-6}$alkyl, and
(c) —$C_{1-6}$alkyl-phenyl;
or wherein $R^1$ and $R^5$ are joined such that together with the carbon atoms to which they are attached there is formed a saturated or unsaturated carbon ring of 3, 4, 5, 6, 7 or 8 atoms;

$R^2$ and $R^3$ are each independently selected from
(a) hydrogen,
(b) —$C_{1-6}$alkyl, and
(c) —$C_{1-6}$alkyl-phenyl;
or wherein two $R^2$ or two $R^3$ are joined such that together with the carbon atoms to which they are attached there is formed a saturated or unsaturated carbon ring of 3, 4, 5, 6, 7 or 8 atoms;

$R^5$ is as defined above or is selected from
(a) hydrogen,
(b) —$C_{1-6}$alkyl,
(c) —$C_{1-6}$alkyl-phenyl $C_{1-6}$alkyl,
(d) —OH,
(e) —O—$C_{1-6}$alkyl, or
(f) —O—$C_{1-6}$alkyl-phenyl $C_{1-6}$alkyl;

$R^6$ is selected from
(a) hydrogen,
(b) —$C_{1-6}$alkyl,
(c) —$C_{1-6}$alkyl-phenyl, wherein the phenyl is optionally substituted with $C_{1-2}$alkyl;
(d) —OH,
(e) —O—$C_{1-6}$alkyl, or
(f) —$C_{1-6}$alkyl-phenyl, wherein the phenyl is optionally substituted with $C_{1-2}$alkyl;
or wherein two $R^6$ are joined to form O= or are joined together such that together with the carbon atom to which they are attached there is formed a saturated or unsaturated carbon ring of 3, 4, 5, 6, 7 or 8 atoms;

$R^8$, $R^9$ and $R^{14}$ are each independently selected from
(a) H,
(b) —$C_{1-6}$alkyl,
(c) halo,
(d) —CN,
(e) —OH,
(f) —$OC_{1-6}$alkyl,
(g) —$OC_{1-6}$alkyl-phenyl,
(h) —$SR^{11}$,
(i) $S(O)R^{11}$, or
$S(O)_2R^{11}$;

$R^{10}$, $R^{15}$, $R^{16}$ and $R^{17}$ are each independently selected from
(a) hydrogen,
(b) —$C_{1-6}$ alkyl, and
(c) —$C_{1-6}$ alkyl-phenyl;

$R^{11}$ is selected from
(a) —$C_{1-6}$ alkyl,
(b) —$C_{2-6}$ alkenyl, (c) —CF$_3$,
(d) -phenyl(R$^{12}$)$_2$, or
(e) —C$_{2-6}$ alkenyl-phenyl(R$^{12}$)$_2$;

R$^{12}$ is
(a) hydrogen,
(b) —C$_{1-6}$ alkyl,
(c) Cl, F, I or Br;

R$^{13}$ is perfluoro C$_{1-6}$alkyl;

A and B are each independently
(a) covalent bond,
(b) O,
(c) S,
(d) S(O), or
(e) S(O)$_2$;

Q is selected from
(a) —CH(OH)R$^{13}$,
(b) —COR$^{13}$,
(c) —COR$^{16}$, or
(d) —C$_{1-4}$alkylCOCOOR$^{17}$;

X$^1$ is selected from
(a) —O—,
(b) —S—,
(c) —S(O)—,
(d) —S(O)$_2$—;

Z is
(a) H, or
(b) -phenyl-(R$^{14}$)$_3$;

m is 0, 1, 2, 3 or 4;
n is 2, 3, 4, 5, 6 or 7; and
r and s are each independently 0, 1, 2, 3, 4, 5, 6, 7 or 8.

Published Application WO 99/15129 discloses selective cPLA$_2$ inhibitors having the formula

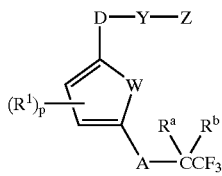

wherein

W is CH=CH, CH=N, O or S;

R$^1$ is (C$_1$–C$_6$)alkyl, (C$_2$–C$_6$)alkenyl, (C$_2$–C$_6$)alkynyl, (C$_1$–C$_6$)alkoxy, (C$_1$–C$_6$)alkylthio, halo, hydroxy, cyano,

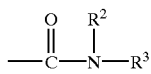

in which R$^2$ and R$^3$ are each independently hydrogen or (C$_1$–C$_6$)alkyl, —COO—(C$_1$–C$_6$)alkyl, CF$_3$, (C$_1$–C$_6$) alkylphenyl, phenyl or phenyl substituted by one or more, preferably 1–3, of (C$_1$–C$_6$)alkyl, —COO—(C$_1$–C$_6$)alkyl,

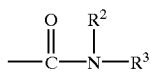

in which R$^2$ and R$^3$ are as defined above, halo, hydroxy, —O—(C$_1$–C$_6$)alkyl, —S—(C$_1$–C$_6$)alkyl or (C$_2$–C$_6$) alkenyl;

p is 0, 1 or 2;

A is V—(R$^c$)$_n$—;

R$^c$ is a straight or branched chain alkyl group;

n is 0 or an integer of from 1 to 6;

R$^a$ and R$^b$ when taken together form an oxo (=O) group, or R$^a$ and R$^b$ are each independently hydrogen or OH;

V is O, —S—, —SO—, —SO$_2$, —CONH or NHCO when n is an integer of from 1 to 6 or V is (C$_2$–C$_6$) alkenyl or a bond when n is 0 or an integer of from 1 to 6;

D is —(CH$_2$)$_m$ or a bond linking the

ring to Y;

m is an integer of from 1 to 6;

Y is —O—, —S—, —SO—, —SO$_2$;

or a bond;

R$^4$ is as defined below for R$^7$;

Z is

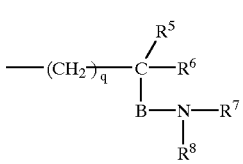 (a)

in which B is:

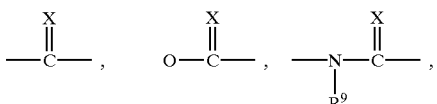

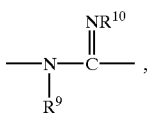

—SO$_2$— or a bond;

X is S or O;

q is an integer from 1 to 6;

R$^9$ is hydrogen or (C$_1$–C$_6$)alkyl;

R$^{10}$ is hydrogen, CN, NO$_2$, OH, —O—(C$_1$–C$_6$)alkyl, (C$_1$–C$_6$) alkyl, phenyl or (C$_1$–C$_6$)alkylphenyl;

R$^5$ and R$^6$ are each independently hydrogen or (C$_1$–C$_{18}$) alkyl;

R$^7$ and R$^8$ are each independently
(a) hydrogen;
(b) (C$_1$–C$_{18}$)alkyl;
(c) (C$_1$–C$_{18}$)alkyl substituted by one or more of
(1) phenyl;
(2) phenyl substituted by 1–5 fluoro, 1–3 (for each of the following phenyl substituents) halo (other than fluoro), 1–3 ($C_1$–$C_6$)alkoxy, 1–3 ($C_1$–$C_6$)alkyl, nitro, cyano, hydroxy, trifluoromethyl, ($C_1$–$C_6$)alkylthio, amino, 1–3 ($C_1$–$C_6$) alkylamino, di($C_1$–$C_6$)alkylamino, —$CO_2H$, —COO—($C_1$–$C_6$)alkyl, —$SO_3H$, —$SO_2NHR^{15}$ in which $R^{15}$ is hydrogen or ($C_1$–$C_6$)alkyl, or

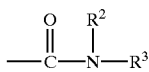

in which $R^2$ and $R^3$ are as defined above;

(3) heterocyclic selected from oxadiazolyl, isoxazolyl, oxazolyl, furyl and thiazolyl;

(4) heterocyclic substituted by one or more of, preferably 1–3, phenyl, phenyl substituted by 1–3 (for each of the following) halo, ($C_1$–$C_6$) alkoxy, ($C_1$–$C_6$)alkyl, nitro, cyano, hydroxy, trifluoromethyl, ($C_1$–$C_6$)alkylthio, amino, ($C_1$–$C_6$)alkylamino, di($C_1$–$C_6$)alkylamino, $CO_2H$, —COO—($C_1$–$C_6$)alkyl, —$SO_3H$, $SO_2NHR^{15}$ in which $R^{15}$ is hydrogen or ($C_1$–$C_6$)alkyl, or

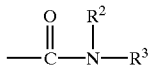

in which $R^2$ and $R^3$ are as defined above, ($C_1$–$C_6$)alkyl or ($C_1$–$C_6$)alkyl substituted by one or more, preferably 1–3, phenyl or heterocyclic groups, said phenyl or heterocyclic group being unsubstituted or substituted by 1–3 (for each of the following) halo, 1–3 ($C_1$–$C_6$)alkoxy, 1–3 ($C_1$–$C_6$)alkyl, nitro, cyano, hydroxy, trifluoromethyl, ($C_1$–$C_6$) alkylthio, amino, 1–3 ($C_1$–$C_6$)alkylamino, di($C_1$–$C_6$)alkylamino, COOH, —COO—($C_1$–$C_6$)alkyl, —$SO_3H$, —$SO_2NHR^{15}$ in which $R^{15}$ is hydrogen or ($C_1$–$C_6$)alkyl, or

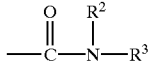

in which $R^2$ and $R^3$ are each independently hydrogen or ($C_1$–$C_6$)alkyl, the heterocyclic radical being selected from imidazolyl, oxadiazolyl, isoxazolyl, pyrrolyl, pyrazolyl, oxazolyl, furyl, thianyl or thiazolyl;

(5) carboxy or —COO—($C_1$–$C_6$)alkyl;

(6) hydroxy, halo, —O—($C_1$–$C_6$) alkyl or —S—($C_1$–$C_6$)alkyl, with the proviso that the OH, ethers or thioethers cannot be on the carbon bearing the heteroatoms;

(7) cyano;

(8) halo, trifluoromethyl or trifluoroacetyl;

(9) $CH_2$ L—$R^{16}$ in which L is

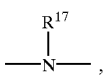

—O—, —S—, —SO—, —$SO_2$—,

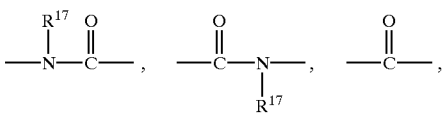

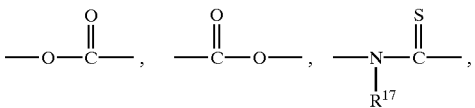

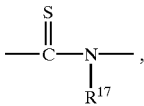

or —O—$SiR^{16}R^{18}R^{19}$ or a bond in which $R^{16}$ and $R^{17}$ are each independently ($C_1$–$C_{18}$)alkyl or ($C_2$–$C_{18}$)alkenyl or ($C_1$–$C_{18}$)alkyl or ($C_2$–$C_{18}$)alkenyl substituted by one or more, preferably 1–3, phenyl or heterocyclic radicals, said phenyl or heterocyclic radicals being unsubstituted or substituted by 1–5 fluoro, 1–3 halo (other than fluoro), 1–3 ($C_1$–$C_6$)alkoxy, 1–3($C_1$–$C_6$)alkyl, nitro, cyano, hydroxy, 1–3 trifluoromethyl, 1–3 ($C_1$–$C_6$)alkylthio, amino, 1–3($C_1$–$C_6$)alkylamino, 1–3 di($C_1$–$C_6$)alkylamino, $CO_2H$, 1–3 —COO($C_1$–$C_6$)alkyl,

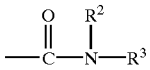

or —$SO_2NHR^9$ in which $R^9$ is hydrogen or ($C_1$–$C_6$)alkyl and $R^2$ and $R^3$ are as defined above;

(b)

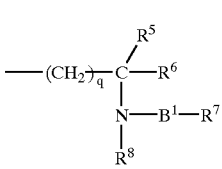

in which B is

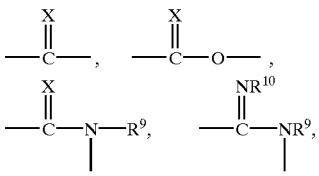

—$SO_2$—, —$PO(OR^9)_2$ or a bond; providing that when $B^1$ is —$PO(OR^9)_2$; then $R^7$ becomes $R^9$, and when $B^1$ is

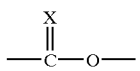

or —SO$_2$—, then R$^7$ cannot be hydrogen;
X, q, R$^5$, R$^6$, R$^7$, R$^8$, R$^9$ and R$^{10}$ are as defined in (a);

(c)

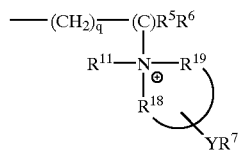

in which q, R$^5$ and R$^6$ are as defined above;
R$^{18}$, R$^{19}$ and R$^{11}$ are as defined above for R$^7$ and R$^8$ except that they may not be hydrogen, or R$^{18}$ and R$^{19}$ taken together with the nitrogen to which they are attached represent a 4, 5- or 6-membered heterocyclic ring and Y, R$^7$ and R$^{11}$ are as defined above, or R$^{18}$, R$^{19}$ and R$^{11}$ taken together with the nitrogen to which they are attached represent pyridinium, said pyridinium group being unsubstituted or substituted by (C$_1$–C$_{12}$)alkyl, (C$_1$–C$_{12}$)alkoxy, amino, (C$_1$–C$_{12}$)alkylamino, di(C$_1$–C$_{12}$)alkylamino,

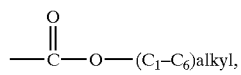

—S—(C$_1$–C$_{12}$)alkyl,

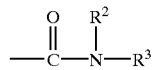

in which R$^2$ and R$^3$ are as defined above, phenyl or phenyl (C$_1$–C$_{10}$)alkyl;

(d)

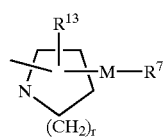

in which R$^{13}$ is (C$_1$–C$_{18}$)alkyl or (C$_1$–C$_{18}$)alkyl substituted by carboxy,

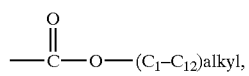

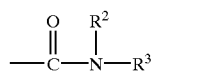

in which R$^2$ and R$^3$ are as defined above, hydroxy, —O—(C$_1$–C$_6$) alkyl, —O—(C$_1$–C$_6$) alkyl or —S—(C$_1$–C$_6$) alkyl substituted by 1 or 2 phenyl or substituted phenyl groups, the substituents for the substituted phenyl groups being 1–5 fluoro or 1–3 (for each of the following phenyl substituents) halo (other than fluoro), (C$_1$–C$_6$)alkoxy, (C$_1$–C$_6$)alkyl, nitro, cyano, hydroxy, trifluoromethyl, (C$_1$–C$_6$) alkylthio, amino, (C$_1$–C$_6$) alkylamino, di(C$_1$–C$_6$) alkylamino, CO$_2$H, COO—(C$_1$–C$_6$) alkyl, SO$_3$H, SO$_2$NHR$^{15}$ in which R$^{15}$ is hydrogen or (C$_1$–C$_6$) alkyl or

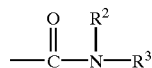

in which R$^2$ and R$^3$ are as defined above;
r is 0 or an integer of from 1 to 3;
R$^7$ is as defined above;
M is —(CH$_2$—)$_m$T where T is

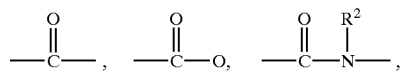

in which R$^2$ is as defined above, —SO$_2$— or a bond when MR$^7$ is on nitrogen and providing that when T is

or —SO— or —SO$_2$—, then R$^7$ cannot be hydrogen, and T is

—O—, —S—, —SO—, —SO2—,

or a bond when MR$^7$ is on a carbon atom of the heterocyclic ring;
R$^{14}$ is hydrogen or (C$_1$–C$_6$)alkyl;
m is 0 or an integer of 1–6;

(e)

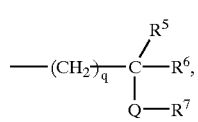

wherein Q is —O—, —S—, —SO— or —SO$_2$—, and q, R$^5$, R$^6$ and R$^7$ are as defined above, providing that when Q is —SO— or —SO$_2$—, R$^7$ cannot be hydrogen;
(f) R$^7$ wherein R$^7$ is defined above, providing that when Y is —SO— or —SO$_2$—, R$^7$ cannot be hydrogen; and
R$^{18}$ and R$^{19}$ are phenyl or phenyl substituted by 1–3 halo, (C$_1$–C$_6$)alkoxy, (C$_1$–C$_6$)alkyl, nitro, cyano, hydroxy, trifluoromethyl, (C$_1$–C$_6$)alkylthio, amino, (C$_1$–C$_6$)alkylamino, di(C$_1$–C$_6$)alkylamino, CO$_2$H, —COO—(C$_1$–C$_6$)alkyl, —SO$_3$H, SO$_2$NHR$^{15}$ in which R$^{15}$ is hydrogen or (C$_1$–C$_6$)alkyl, or

in which $R^2$ and $R^3$ are as defined above; or pharmaceutically acceptable salts, solvates or prodrugs thereof.

$R^{18}$ and $R^{19}$ are phenyl or phenyl substituted by 1–3 halo, $(C_1-C_6)$alkoxy, $(C_1-C_6)$ alkyl, nitro, cyano, hydroxy, trifluoromethyl, $(C_1-C_6)$ alkylthio, amino, $(C_1-C_6)$ alkylamino, di$(C_1-C_6)$alkylamino, $CO_2H$, —COO—$(C_1-C_6)$alkyl, —$SO_3H$, $SO_2NHR^{15}$ in which $R^{15}$ is hydrogen or $(C_1-C_6)$alkyl, or

in which $R^2$ and $R^3$ are as defined above; or pharmaceutically acceptable salts, solvates or prodrugs thereof.

There is nothing in any of the foregoing references, or in the general prior art, to suggest the novel alpha beta substituted trifluoromethyl-ketones of the present invention as cytosolic phospholipase A2 inhibitors.

SUMMARY OF THE INVENTION

An object of the present invention is to provide novel alpha and/or beta substituted trifluoromethylketone compounds which inhibit cytosolic phospholipase $A_2$ enzymes that are pro-inflammatory mediators. Some of the derivatives exhibit increased stability and aqueous solubility.

This invention relates to novel cytosolic phospholipase inhibitors represented by formula I, or a pharmaceutically acceptable salt thereof

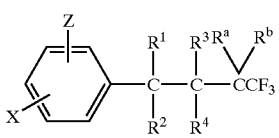

I wherein
$R^a$ and $R^b$ when taken together form an oxo (=O) group, or $R^a$ and $R^b$ are each independently hydrogen or OH;
X is H, $CF_3$, halogen, $NR^5R^6$, $NH(CO)NR^5R^6$, $C(O)NR^5R^6$, OH, $OR^7$, SH, $S(O)_nR^7$, $C(O)OR^8$, $NH(CO)OR^{10}$ $C_1-C_7$ alkyl, $C_2-C_7$ alkenyl, $C_2-C_7$ alkynyl or $C_3-C_7$ cycloalkyl, said alkyl, alkenyl, alkynyl or cycloalkyl group being optionally substituted by $COOR^8$, CN, $C(O)NR^5R^6$, $PO_3R^8$, $SO_3R^8$, heterocyclic, OH, $OR^7$, SH, $S(O)_nR^7$, $NR^5R^6$, $NH(CO)$ $NR^5R^6$, $NH(CO)OR^{10}$, $OC(O)OR^{10}$, aryl or heteroaryl, said aryl or heteroaryl being optionally substituted by one or two groups independently selected from $COOR^8$, $SO_3R^8$, $OCOR^8$, $PO_3R^8$ or heterocyclic;
$R^1$ and $R^2$ are each independently H, OH, $OR^7$, SH, $S(O)_nR^7$, substituted $C_1-C_7$ alkyl, $C_2-C_7$ alkenyl, $C_2-C_7$ alkynyl or $C_3-C_7$ cycloalkyl, said alkyl, alkenyl, alkynyl or cycloalkyl group being substituted by $COOR^8$, CN, $C(O)NR^5R^6$, $PO_3R^8$, $SO_3R^8$, heterocyclic, OH, $OR^7$, SH, $S(O)_nR^7$, $NR^5R^6$, $NH(CO)$ $NR^5R^6$, $NH(CO)OR^{10}$, $OC(O)OR^{10}$, aryl or heteroaryl, said aryl or heteroaryl group being optionally substituted by one or two groups independently selected from $COOR^8$, $SO_3R^8$, $PO_3R^8$ or heterocyclic;
$R^3$ and $R^4$ are each independently H, methylene, OH, $OR^7$, SH, $S(O)_nR^7$, $NHCOR^7$, $COOR^8$, $C(O)NR^5R^6$, substituted $C_1-C_7$ alkyl, $C_2-C_7$ alkenyl, $C_2-C_7$ alkynyl or $C_3-C_7$ cycloalkyl, said alkyl, alkenyl, alkynyl or cycloalkyl group being substituted by $COOR^8$, CN, $C(O)NR^5R^6$, $PO_3R^8$, $SO_3R^8$, heterocyclic, OH, $OR^7$, SH, $S(O)_nR^7$, $NR^5R^6$, $NH(CO)NR^5R^6$, $NH(CO)OR^{10}$, $OC(O)OR^{10}$, aryl or heteroaryl, said aryl or heteroaryl group being optionally substituted by one or two groups independently selected from $COOR^8$, $SO_3R^8$, $PO_3R^8$ or heterocyclic;
$R^5$ and $R^6$ are each independently H, $C_1-C_7$ alkyl, $C_2-C_7$ alkenyl, $C_2-C_7$ alkynyl, $C_3-C_7$ cycloalkyl, heterocyclic, aryl or heteroaryl, said alkyl, alkenyl, alkynyl, cycloalkyl, heterocyclic, aryl or heteroaryl group being optionally substituted with $COOR^8$, CN, $OR^8$, $NR^8R^9$, $SO_3R^8$, $PO_3R^8$, halogen, aryl or heteroaryl, said aryl or heteroaryl substituent being optionally substituted with one or two groups independently selected from $COOR^8$, $SO_3R^8$, $PO_3R^8$ or heterocyclic;
$R^7$ is $C_1-C_7$ alkyl or $C_3-C_7$ cycloalkyl, said alkyl or cycloalkyl group being optionally substituted by $COOR^8$, CN, $C(O)NR^5R^6$, $PO_3R^8$, $SO_3R^8$, heterocyclic, $OR^5$, $SR^5$, $S(O)_nR^{10}$, $NR^5R^6$, $NH(CO)$ $NR^5R^6$, $NH(CO)OR^{10}$, $C(O)_2OR^{10}$, aryl or heteroaryl, said aryl or heteroaryl group being optionally substituted with one or two groups independently selected from $COOR^8$, $SO_3R^8$, $PO_3R^8$ or heterocyclic;
$R^8$ and $R^9$ are each independently H, $C_1-C_7$ alkyl or $C_3-C_7$ cycloalkyl;
$R^{10}$ is the same as $R^5$ and $R^6$ but is not H;
Z is $OR^{11}$, $S(O)_nR^{11}$, $NR^{11}R^{12}$ or $CHR^{11}R^{12}$;
$R^{11}$ and $R^{12}$ are each independently hydrogen, $C_1-C_7$ alkyl, $C_2-C_7$ alkenyl, $C_2-C_7$ alkynyl or $C_3-C_7$ cycloalkyl, said alkyl, alkenyl, alkynyl or cycloalkyl group being optionally substituted with $NR^{13}R^{14}$, $SR^{13}$, $S(O)R^{18}$, $SO_2R^{18}$ or $OR^{13}$, with the proviso that both $R^{11}$ and $R^{12}$ may not both be hydrogen;
$R^{13}$ and $R^{14}$ are each independently H, $SiR^{15}R^{16}R^{17}$, $C_1-C_7$ alkyl, $C_2-C_7$ alkenyl, $C_2-C_7$ alkynyl or $C_3-C_7$ cycloalkyl or aryl, said alkyl, alkenyl, alkynyl, cycloalkyl or aryl group being optionally substituted with 1–3 $COOR^8$, $OR^8$, $SiR^{15}R^{16}R^{17}$, $OR^{15}$, aryl, biaryl or heteroaryl, said aryl, biaryl or heteroaryl group being optionally substituted with 1–3 halogen, $CF_3$, $OR^8$, $COOR^8$, $NO_2$ or CN, or $R^{13}$ and $R^{14}$ when taken together with the nitrogen to which they are attached form a 5–7 membered heterocyclic ring with one or more O, N or S heteroatoms, said ring being optionally substituted with $COOR^8$ or $C_1-C_5$ alkyl optionally substituted with $OR^8$, $COOR^8$ or $C(O)$ $NR^5R^6$;
$R^{15}$, $R^{16}$ and $R^{17}$ are each independently aryl, benzyl, benzhydryl, biaryl, heteroaryl, aryl$(C_1-C_6)$alkyl or heteroaryl$(C_1-C_6)$alkyl, said aryl group being optionally substituted with halogen, $CF_3$, $OR^8$, $COOR^8$, $NO_2$, CN or $C_1-C_7$ alkyl;
$R^{18}$ is the same as $R^{13}$ and $R^{14}$ but is not H;
n is 0, 1 or 2; or a pharmaceutically acceptable salt thereof, with the proviso that at least one of $R^1$, $R^2$, $R^3$ and $R^4$ is other than hydrogen.

Another aspect of this invention involves methods for inhibiting cytosolic $PLA_2$ in a mammal in need thereof which comprises administering to said mammal a therapeutically effective amount of a compound of formula I and methods for using the compounds of formula I to treat various diseases characterized by inappropriate activation of the cytosolic $PLA_2$ enzymes such as asthma, allergic rhinitis, cerebral ischemia, Alzheimer's Disease, rheumatoid arthritis, acute pancreatitis, inflammatory bowel disease, psoriasis, gout, neutrophil and platelet activation, chronic skin inflammation, shock, trauma-induced inflammation such as spinal cord injury, damage to the skin resulting from UV light or burns and macrophage activation. In further aspects, the present invention provides pharmaceutical compositions comprising a therapeutically effective amount of a compound of formula I and a pharmaceutically acceptable carrier and processes for preparing the compounds of formula I.

DETAILED DESCRIPTION

The object of this invention was to discover a selective $cPLA_2$ inhibitor which is active, both topically and orally, in treating inflammatory disease of the skin and other tissues as well as other chronic and acute conditions which have been linked to inappropriate activation of the $cPLA_2$ enzymes. Preferably such compound would also be devoid of undesirable lipid-perturbing activities associated with skin irritation.

The above-mentioned objectives have been met by the compounds of formula I described above.

Definitions

In the present application the numbers in the subscript after the symbol "C" define the number of carbon atoms a particular group can contain. For example, "$C_1$–$C_7$ alkyl" refers to straight and branched chain alkyl groups with 1 to 7 carbon atoms. Similarly, "$C_2$–$C_7$ alkenyl refers to an unsaturated hydrocarbon group containing from 2 to 7 carbon atoms and at least one carbon-carbon double bond. The term "$C_2$–$C_7$alkynyl" refers to an unsaturated hydrocarbon group containing from 2 to 7 carbon atoms and at lease one triple bond.

The term "halogen" or "halo" as used herein refers to fluorine, chlorine, bromine or iodine.

"Aryl" as used herein refers to a $C_6$ monocyclic aromatic ring system or a $C_9$ or $C_{10}$ bicyclic carbocyclic ring system having one or two aromatic rings such as phenyl or naphthyl. It may also refer to a $C_{14}$ tricyclic carbocyclic ring system having two or three aromatic rings such as anthracenyl or phenanthrenyl. Unless otherwise indicated, "substituted aryl" refers to aryl groups substituted with one or more (preferably from 1 to 3) substituents independently selected from ($C_1$–$C_6$)alkyl, halo($C_1$–$C_6$)alkyl, ($C_1$–$C_6$)alkoxy, ($C_1$–$C_6$)alkoxy-carbonyl, ($C_1$–$C_6$)alkanoyl, hydroxy, halo, mercapto, nitro, amino, cyano, ($C_1$–$C_6$)alkylamino, di($C_1$–$C_6$)alkylamino, carboxy, aryl, aryl ($C_1$–$C_6$)alkyl, aryl ($C_1$–$C_6$)alkoxy, heterocyclic, heterocyclic ($C_1$–$C_6$)alkyl and the like. The term "biaryl" refers to two $C_6$ monocyclic aromatic ring systems or two $C_9$ or $C_{10}$ bicyclic carbocyclic ring systems linked together such as o-, m- and p-biphenyl or o-, m- and p-binaphthyl. The term "heteroaryl" refers to a 5- or 6-membered aromatic ring system or a 9- or 10-membered bicyclic aromatic ring system containing one, two or three heteroatoms selected from N, O and S. The term "benzhydryl" refers to a carbon atom bearing two aryl, bis-aryl or heteroaryl groups.

The term "heterocyclic" as used herein refers to a 4-, 5- or 6-membered ring containing one, two or three heteroatoms selected from N, O and S. The 5-membered ring has 0–2 double bonds and the 6-membered ring has 0–3 double bonds. The nitrogen heteroatoms can be optionally quaternized or N-oxidized. The sulfur heteroatoms can be optionally S-oxidized. The term "heterocyclic" also includes bicyclic groups in which any of the above heterocyclic rings is fused to a benzene ring or a cyclohexane ring or another heterocyclic ring. Heterocyclics include: pyrrolyl, pyrrolinyl, pyrrolidinyl, pyrazolyl, pyrazolinyl, pyrazolidinyl, imidazolyl, imidazolidinyl, pyridyl, piperidyl, pyrazinyl, piperazinyl, pyrimidinyl, pyridazinyl, oxazolyl, oxazolinyl, oxazolidinyl, isoxazolyl, isoxazolinyl, isoxazolidinyl, morpholinyl, thiazolyl, thiazolidinyl, isothiazolyl, isothiazolidinyl, indolyl, quinolinyl, benzimidazolyl, benzothiazolyl, benzoxazolyl, benzofuranyl, furyl, dihydrofuranyl, tetrahydrofuranyl, pyranyl, dihydropyranyl, dioxolanyl, thienyl, benzothienyl and diaxanyl.

In a preferred embodiment, the Z substituent in the compounds of formula I is in the para-position.

In another preferred embodiment, the $R^1$ and $R^2$ substituents of a compound of formula I are both hydrogen.

In another preferred embodiment, the $R^3$ and $R^4$ substituents of a compound of formula I are both hydrogen.

In another preferred compound, substituent Z in the compounds of formula I is Y—$Z^1$ in which Y is —O—, —S(O)$_n$—,

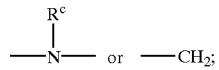 or —CH$_2$;

n is 0, 1 or 2;

$R^c$ is H, —COCF$_3$, —COC$_6$H$_5$, —COO(C$_1$–C$_6$)alkyl,

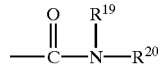

in which $R^{19}$ and $R^{20}$ are each independently H or (C$_1$–C$_6$)alkyl, (C$_1$–C$_{18}$)alkyl or (C$_1$–C$_{18}$)alkyl substituted by one or more of phenyl or phenyl substituted by 1–5 fluoro, 1–3 halo (other than fluoro), 1–3 (C$_1$–C$_6$) alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$)alkylamino, 1–3 di(C$_1$–C$_6$) alkylamino, 1–3 carboxyl, 1–3 —COO(C$_1$–C$_6$)alkyl, 1–3 —SO$_3$H, 1–3 —SO$_2$NHR$^{21}$ in which R$^{21}$ is hydrogen or (C$_1$–C$_6$)alkyl, or

in which $R^{19}$ and $R^{20}$ are as defined above; and $Z^1$ is (a)

in which $n^1$ is 0, 1 or 2 and $R^{22}$ and $R^{23}$ are phenyl or phenyl substituted by 1–5 fluoro, 1–3 halo (other than fluoro), 1–3 (C$_1$–C$_6$)alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$)alkylamino, 1–3 di(C$_1$–C$_6$)alkylamino, 1–3 carboxy, 1–3 —COO($C_1$–$C_6$)alkyl, 1–3 —$SO_3H$, 1–3 —$SO_2NHR^{21}$ in which $R^{21}$ is hydrogen or ($C_1$–$C_6$)alkyl, or

in which $R^{19}$ and $R^{20}$ are as defined above;

(b)

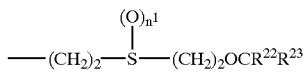

in which $n^1$ is 0, 1 or 2 and $R^{22}$ and $R^{23}$ are as defined above;

(c)

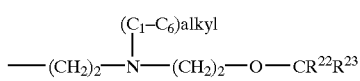

in which $R^{22}$ and $R^{23}$ are as defined above;

(d)

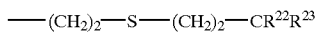

in which $R^{22}$ and $R^{23}$ are as defined above;

(e)

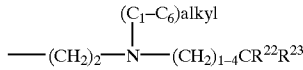

in which $R^{22}$ and $R^{23}$ are as defined above; or (f)

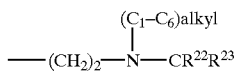

in which $R^{22}$ and $R^{23}$ are as defined above.

Within this preferred subground, more preferred compounds are those wherein $R^1$ and $R^2$ are both hydrogen, $R^3$ is hydrogen, $R^4$ is —OH, —$OCH_3$, —O-i-propyl, —$CH_2OH$, —$CH_2OCH_2OCH_3$, —$COOCH_3$, —$(CH_2)_v$COO-t-butyl, —$(CH_2)_v$$COOC_2H_5$, —$(CH_2)_v$COOH,

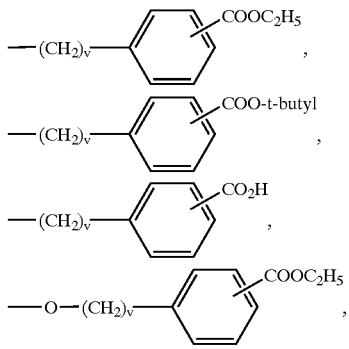

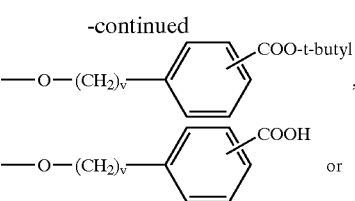

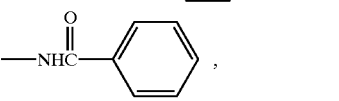

and v is 0 or an integer of from 1–6.

Other preferred compounds within this subgroup are those wherein $R^1$, $R^3$ and $R^4$ are hydrogen, $R^2$ is —S($CH_2$)$_v$COO-t-butyl, —S—($CH_2$)$_v$$CO_2H$, —($CH_2$)$_v$COO-t-butyl, —($CH_2$)$_v$$CO_2H$,

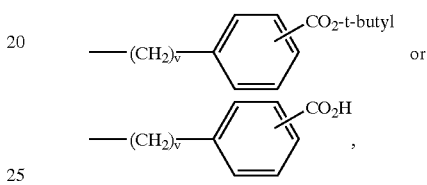

and v is 0 or an integer of from 1–6.

A most preferred embodiment embraces compounds of formula I wherein X is H.

Some of the compounds described herein contain one or more asymmetric centers and may thus give rise to diastereomers and optical isomers. The present invention is meant to include such possible diastereomers as well as their racemic and resolved, enantiomerically pure forms, and pharmaceutically acceptable salts thereof.

As mentioned above the invention also includes pharmaceutically acceptable salts of the compounds of formula I. A compound of the invention can possess a sufficiently acidic, a sufficiently basic, or both functional groups. Accordingly, a compound may react with any of a number of inorganic bases, and organic and inorganic acids, to form a pharmaceutically acceptable salt.

The term "pharmaceutically acceptable salt" as used herein refers to salts of the compounds of formula I which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogen phosphate, dihydrogen phosphate, metaphosphate, pyrophosphate, chloride, bromide, iodide, acetate, propionate, decanoate, caprylate, acrylate, formate, isobutyrate, caproate, heptanoate, propionate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylene-sulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napthalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. Suitable organic bases include trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine, or the like pharmaceutically acceptable amines. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

The present invention also includes solvated forms of the compounds of formula I, particularly hydrates, in which the trifluoromethyl ketone group exists as a mixture of ketonic I and hydrated forms II and are each independently interconvertible and pharmacologically active.

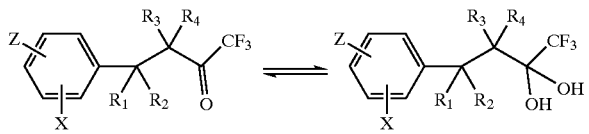

As used herein and in the reaction schemes the term "reduction" is intended to include well-known reduction procedures of ester groups by the use of aluminum or boron hydrides such as lithium aluminum hydride, aluminum hydride, diisobutylaluminum hydride, sodium borohydride, sodium cyanoborohydride and the like in an inert organic solvent such as tetrahydrofuran, ethyl ether, ethanol, dichloromethane and the like. The term "reduction" is also intended to include the various methods of reducing unsaturated bonds. Well-known hydrogenolysis procedures using hydrogen with a catalyst such as palladium or platinum on charcoal, palladium or platinum hydroxide on charcoal, rhodium on charcoal in a solvent such as ethanol or ethyl acetate may be used if appropriate. Other methods including the use of hydrazine or triethylsilane and the Wilkinson's catalyst or a metal in methanol such as magnesium for example may also be useful.

As used herein and in the reaction schemes, the term "hydrolysis" is intended to include conventional hydrolysis procedures of esters well-known to those skilled in the art. For example, methyl or ethyl esters may be removed by the use of aqueous solutions of sodium or potassium alkoxides in tetrahydrofuran or ethanol. The hydrolysis of tert-butyl esters are carried out under acidic conditions such as 90% trifluoroacetic acid or 6N hydrochloric acid in solvents such as tetrahydrofuran or dichloromethane. Allyl esters may be removed by the use of Pd(0) catalyst such as sodium acetate, potassium or sodium 2-ethylhexanoate, pyrolidine or morpholine and the like in an organic solvent such as acetonitrile, tetrahydrofuran, dichloromethane and the like. Finally, silyl esters such as trimethylsilylethyl esters may be cleaved by the use of tetrabutylammonium fluoride in tetrahydrofuran.

As used herein and in the reaction schemes, the term "enol triflate or enol formation" is intended to include conventional and well-known enolate formation procedures and subsequent trapping of this enolate by the well-known triflating or silylating agents. Thus the ketones are treated with an organic base such as 2,6-di-tert-butyl-4-methyl-pyridine, sodium hydride, potassium hydride, lithium diisopropylamide or lithium bis(trimethylsilyl)amide in an inert organic solvent such as tetrahydrofuran, dimethylformamide or dichloromethane and the like. The resulting enolates are then reacted with triflic anhydride or 2-[N,N-bis(trifluoromethylsulfonyl)amino]pyridine and the like or an alkylsilyl halides or triflates.

As used herein and in the reaction schemes, the term "cross-coupling" is intended to include all the cross-coupling methods well-known by those skilled in the art that involve the reaction of a vinyl or aromatic triflate, bromide or iodide with a tin, zinc, magnesium or boronic derivative catalyzed by a palladium(0) or palladium(II) catalyst such as tetrakis(triphenyl-phosphine)palladium(0), bis(triphenylphosphine)palladium(II) chloride, palladium(II) acetate, tris(dibenzylidene-acetone)dipalladium(0), bis(diphenylphosphineferrocene)palladium(II) chloride and the like or a nickel(0) or nickel(II) catalyst such as tetrakis(triphenylphosphine)nickel(0), bis(triphenylphosphine)nickel(II) chloride and the like. Very often, as known by those skilled in the art, copper iodide, lithium chloride, zinc chloride or triphenylarsine, tris(2-furyl)phosphine or tris(2,4,6-trimethoxyphenyl)phosphine must be added. When a boronic acid derivative is used, the reaction proceeds only in the presence of an inorganic base such as potassium phosphate or carbonate or sodium carbonate. These reactions are performed in an inert organic solvent such as dioxane, N-methylpyrrolidone, dimethylformamide, dimethoxyethane, tetrahydrofuran, toluene, benzene and the like.

As used herein and in the reaction schemes the term "alkylation" is intended to include conventional and well-known alkylation procedures. Thus, the desired alcohol or ketone groups which are to be alkylated are treated in the presence of an organic or inorganic base such as sodium hydride, potassium hydride, lithium diisopropylamine or lithium bis(trimethylsilyl)amide in an inert organic solvent such as tetrahydrofuran, dimethylformamide, hexamethylphosphoramide, dimethylsulfoxide, N-methylpyrolidinone and the like. Then an alkylating agent such as an alkyl, allyl or benzyl halide, mesylate or tosylate is added to this generated enolate, alcoholate, phenolate or thiophenolate.

As used herein and in the reaction schemes, the term "Michael addition" is intended to include all conventional methods of conjugate addition of organometallic compounds or anions formed from malonates, cyanoacetates, acetoacetates, β-ketoesters, esters, ketones, alkehydes, nitriles, nitro compounds, sulfones and the like to an α,β-unsaturated ketone. The organometallic compounds include lithium dialkylcopper, organoaluminum, trialkylzinc lithium, arylpalladium, arylmercury, borane reagents and the like. The inert organic solvents used may be tetrahydrofuran, dioxane, dimethylformamide, dichloromethane, benzene and the like.

As used herein and in the reaction schemes, the term "epoxidation" is intended to include the well-known methods of epoxide formation by reaction of an olefin with a peracid, preferably m-chloroperbenzoic acid or peracetic acid in a solvent such as dichloromethane and the like.

As used herein and in the reaction schemes, the term "hydroxylation" is intended to include all the synthetic methodologies introducing and hydroxyl group at position a to a carbonyl functionality. Hence the enol or enolate of the carbonyl functionality is formed by reaction with a base such as sodium hydride, potassium hydride, lithium diisopropylamine or lithium bis(trimethylsilyl)amide in an inert organic solvent such as tetrahydrofuran, dimethylformamide, hexamethylphosphoramide, dimethylsulfoxide, N-methylpyrolidinone and the like. Subsequent reaction with the various oxidizing agents such as trans-2-phenylsulfonyl-3-phenyloxaziridine or trimethylsilylhydroperoxide and the like is then performed.

As used herein and in the reaction schemes the term "acylation" is intended to include conventional and well-known acylation procedures for the preparation of amides such as the use of leaving groups and activating groups on the acyl portion of the fatty acid. For example, the use of acid chlorides and carbodiimide as activating groups in organic solvent such as tetrahydrofuran, dichloromethane or mixture of aqueous-organic solvents in the presence of a base such as triethylamine, pyridine, dimethylaminopyridine and 50% sodium acetate.

Biological Activity

The assay determining the activity of cPLA$_2$ inhibitors is the following:

$^3$H-arachidonate-labeled U937 membranes were prepared from U937 cells grown in RPMI 1640 medium containing L-glutamine supplemented with 10% fetal calf serum and 50 μg/ml gentamycin in a 5% $CO_2$ incubator at 37° C. Sixteen hours prior to harvesting the cells, $^3$H-arachidonate (100 Ci/mmol) was added to the cell culture (1×10$^6$ cells/ml, 0.5 μCi/ml). After washing the cells with HBSS (Hank's Balanced Salts) containing 1 mg/ml HSA (Human Serum Albumin), the cells were lysed by nitrogen cavitation and the homogenate was centrifuged at 2,000×g for 10 minutes. The supernatant was further centrifuged at 50,000×g for 30 minutes after which the pellet was resuspended in water and autoclaved at 120° C. for 15 minutes to inactivate any residual phospholipase A$_2$ activity. This suspension was then recentrifuged at 50,000×g for 30 minutes and the pellet resuspended in distilled water.

Assays of cPLA$_2$ activity using these $^3$H-arachidonate-labeled U937 membranes as substrate typically employ human recombinant cPLA$_2$ [see Burke et al., *Biochemistry*, 1995, 34: 15165–15174] and membrane substrate (22 μM phospholipid) in 20 mM HEPES [N-(2-hydroxyethyl) piperazine-N$^1$-(2-ethanesulfonic acid)] buffer, pH 8, containing 6 mM $CaCl_2$, 0.9 mg/ml albumin and 4 M glycerol. Enzyme assays are allowed to proceed for 3 hours at 37° C. before removing the non-hydrolyzed membranes. The hydrolyzed, radiolabeled fatty acid is then measured by liquid scintillation counting of the aqueous phase.

The effects of inhibitor are calculated as percent inhibition of $^3$H-arachidonate formation, after correcting for nonenzymatic hydrolysis, as compared to a control lacking inhibitor according to the following formula:

percent inhibition=((Control *DPM*–Inhibitor *DPM*)/Control *DPM*)×100%

Various concentrations of an inhibitor were tested, and the percent inhibition at each concentration was plotted as log concentration (abscissa) versus percent inhibition (ordinate) to determine the $IC_{50}$ values.

In this assay the compounds of Examples 1 shown below exhibited cPLA$_2$ $IC_{50}$ values in the range of from about 1 to 50 μm.

Since the compounds of the present invention are selective inhibitors of cytosolic phospholipase A$_2$, they are of value in the treatment of a wide variety of clinical conditions.

Inflammatory disorders which may be treated by inhibition of cytosolic cPLA$_2$ include such conditions as arthritis, psoriasis, asthma, inflammatory bowel disease, gout, trauma-induced inflammation such as spinal cord injury, Alzheimer's Disease, cerebral ischemia, chronic skin inflammation, shock, damage to skin resulting from exposure to ultraviolet light or burns, allergic rhinitis, acute pancreatitis, and the like.

The compounds of the present invention have also been found to be very stable towards keto-reduction. It has been shown that a reliable method to assess keto-stability of compounds is to measure the percent of such compounds remaining after incubation with erythrocyte lysates [Rady-Pentek P., et al., *Eur. J. Clin. Pharmacol.*, 1997, 52(2): 147–153]. The assay is the following.

Male Wistar rates were anesthetized with $CO_2$ and then blood was removed by direct cardio-puncture or through a pre-inserted jugular vein canula into syringes that were pre-rinsed with heparin. The blood was then inserted into heparanized tubes and placed on ice. The blood was centrifuges as 3000 rpm for 5 minutes to separate the plasma. The plasma was removed and an equivalent volume of sterile water was mixed with the erythrocyte fraction. This was mixed by inversion and left on ice for several minutes to lyse the erythrocytes. The erythrocyte-water mixture was then centrifuged at 3000 rpm for 5 minutes to pellet the cellular debris.

Each compound was dissolved in methanol (1 ml) to produce a 2 mM solution. From this solution, 50 μl aliquot was made up to 1 ml in 50% methanol to produce a 100 μM stock solution. From this solution, a dose solution was prepared by diluting 100 μl to 2 ml of a 0.1 M potassium phosphate buffer (pH=7.4) to produce a 2 μM final incubation dilution.

The lysate (250 μl) was then aliquoted into eppendorf tubes, 6 for each compound, i.e. 0 time, 15 minutes, 60 minutes in duplicate. To these aliquots was added 200 μl of the dose solution and this was preheated to 37° C. for 2–3 minutes prior to the addition of NADPH (1 mM final concentration) to start the reactions. The reactions were terminated with the addition of either 0.5 ml or 1 ml of acetonitrile. Following centrifugation at 8000×g for 5 minutes, the supernatant was removed and stored at −20° C. until analysis could proceed by quantitative LC/MS. Samples were analyzed by electrospray ionization (ESI) on a Micromass ZMD 2000® single quadrupole mass spectrometer coupled to a Shimadzu HPLC system. The percent of compound remaining following 15 minutes and 60 minutes incubation is calculated relative to the 0 time point.

Administration Modes

The compounds of formula I are usually administered in the form of pharmaceutical compositions. They can be administered by a variety of routes including oral, rectal, transdermal, subcutaneous, intravenous, intramuscular, and intranasal. The compounds are effective as both injectable and oral compositions. Such compositions are prepared in a manner well known in the pharmaceutical art and comprise at least one active compound defined by formula I and a pharmaceutically acceptable carrier.

In making the compositions employed in the present invention the active ingredient is usually mixed with an excipient, diluted by an excipient or enclosed within a carrier which can be in the form of a capsule, sachet, paper or other container. When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Method of Preparation

The compounds of the present invention can be prepared by various methods which are known in the art. Illustrative methods of preparation are provided in the reaction schemes which follow and in the Examples.

Preparation of compounds of formula I may be accomplished via one or more of the synthetic schemes which are described below. The specific examples which follow illustrate the synthesis of representative compounds of the present invention and are not to be construed as limiting the invention in sphere or scope. The methods may be adapted to variations in order to produce compounds embraced by this invention but not specifically disclosed. Further, variations of the methods to produce the same compounds in somewhat different fashion will also be evident to one skilled in the art.

Scheme A describes methods of preparing the compounds of generic formula I wherein $R_3$ and $R_4$ are hydrogens. Thus, the various substituted benzaldehydes may be reacted with 1,1,1-trifluoroacetone in presence of piperidine and acetic acid in a solvent such as tetrahydrofuran and the like to give the unsaturated trifluoromethylketone II. Then, subsequent conjugate additions may be performed with various cuprates or other nucleophiles to introduce the desired substituents $R_1$ or $R_2$. Alternatively, the various aromatic halides may be converted to the corresponding stannanes or boronates III which are then submitted to a cross-coupling with the enol triflates IV of various α-ketoesters. The resulting coupling adduct V may alternatively be reduced or submitted to a conjugate addition to introduce the $R_2$ substituent. Both resulting esters VIA and VIB are finally converted to the corresponding trifluoromethylketones by the methods known in the art. It should be noted that this last approach may also lead to compounds of generic formula 1 wherein $R_3$ is not a hydrogen. The preparation of enol triflates IV bearing an $R_3$ substituent different from a hydrogen is well-known by those skilled in the art.

The synthetic methods to prepare generic compounds of Formula I wherein $R_1$ and $R_2$ are hydrogens are outlined in Schemes B and C. Conversion of the various propionates VII to the corresponding β-trifluoromethylketoesters IB was performed by using trifluoroacetic anhydride followed by an alcohol $R_8OH$. These trifluoromethylketones may then be protected as enol triflates VII which allow the reduction of the esters to the corresponding alcohols IX. Subsequent hydrolysis of enol ethers IX may afford the unsaturated trifluoromethylketones IC which, if desired, may be submitted to a conjugate addition with various nucleophiles and provide the compounds of the generic structure I substituted at position α.

Other alternative approaches are also described in Scheme B. The various propionates VII may be converted to the corresponding trifluoromethylketones IE by using the various methods known in the art. Protection of these trifluoromethylketones as enol ethers X may be followed by an epoxidation or a bromination of the double bond. The bromides XI resulting from the bromination may then react with various alcohols $R_{20}OH$ to afford the epoxides XII. Subsequent alcoholysis will provide compounds of the generic structure I bearing an α-alkoxy substituent (IF). On the other hand, the various propionates may alternatively be oxidized to the corresponding α-hydroxyesters XIII which may then be alkylated with various halides. The usual conversion of the resulting esters XIV to the trifluoromethylketones afford the compounds of generic structure IF.

When it is desired to have a compound of generic formula I wherein the $R_3$ or $R_4$ substituent is an amine or an amide, the synthesis may preferably be done from various substituted aminoesters of type XV, which after acylation using the conditions well known in the art, may provide the amides XVI. Subsequent conversion to the trifluoromethylketones of generic structure IG may then be performed in using the conditions known in the art.

Scheme A
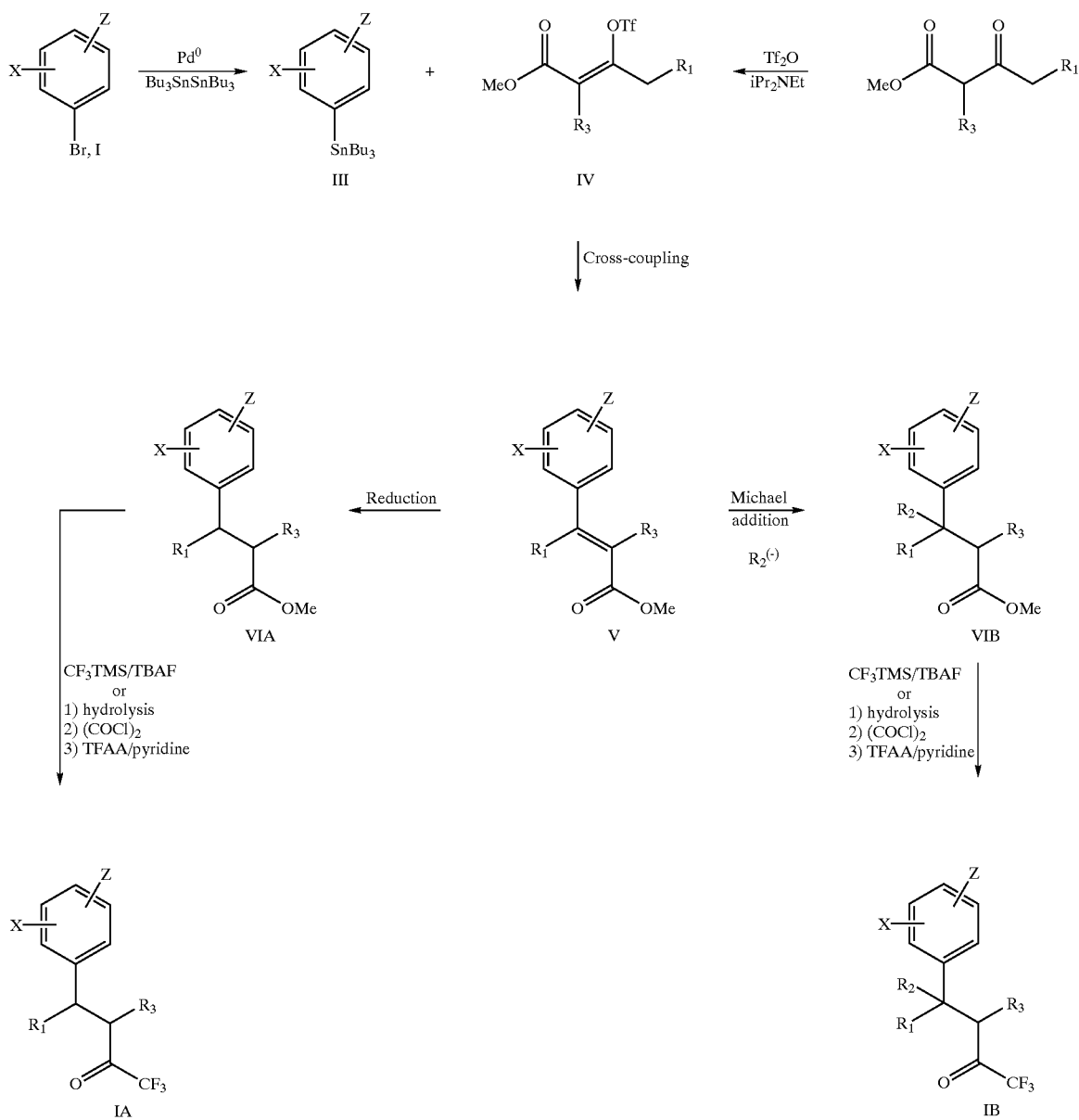

Scheme B
Preparation of the α-substituted analogs:
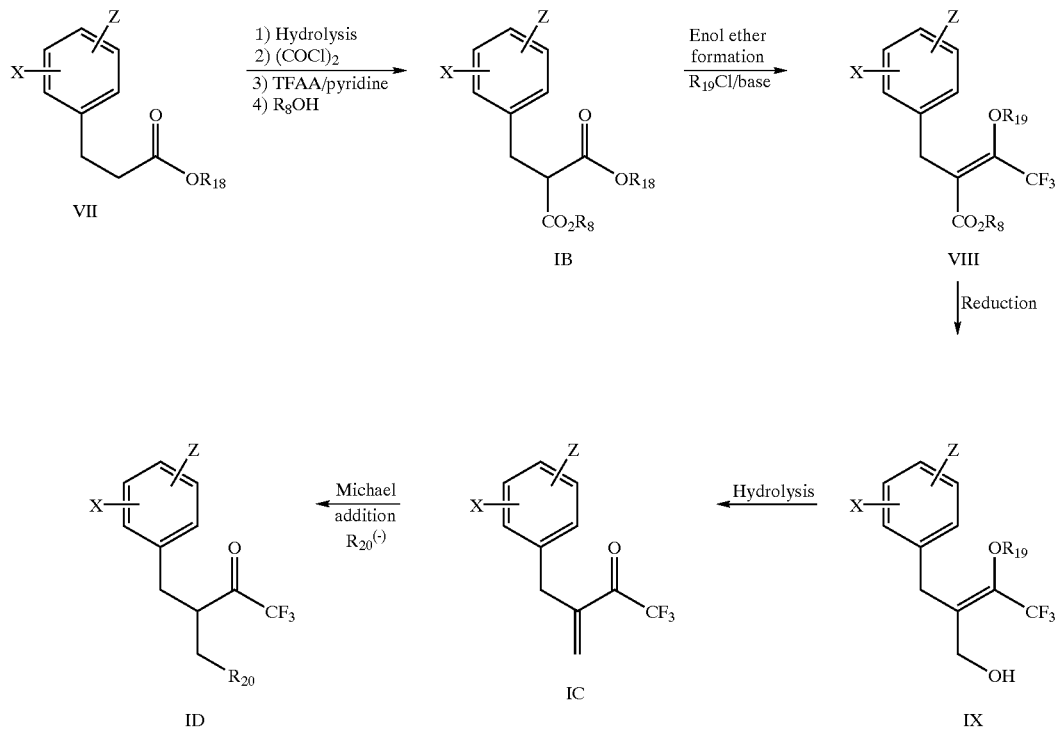
Alternative approach:
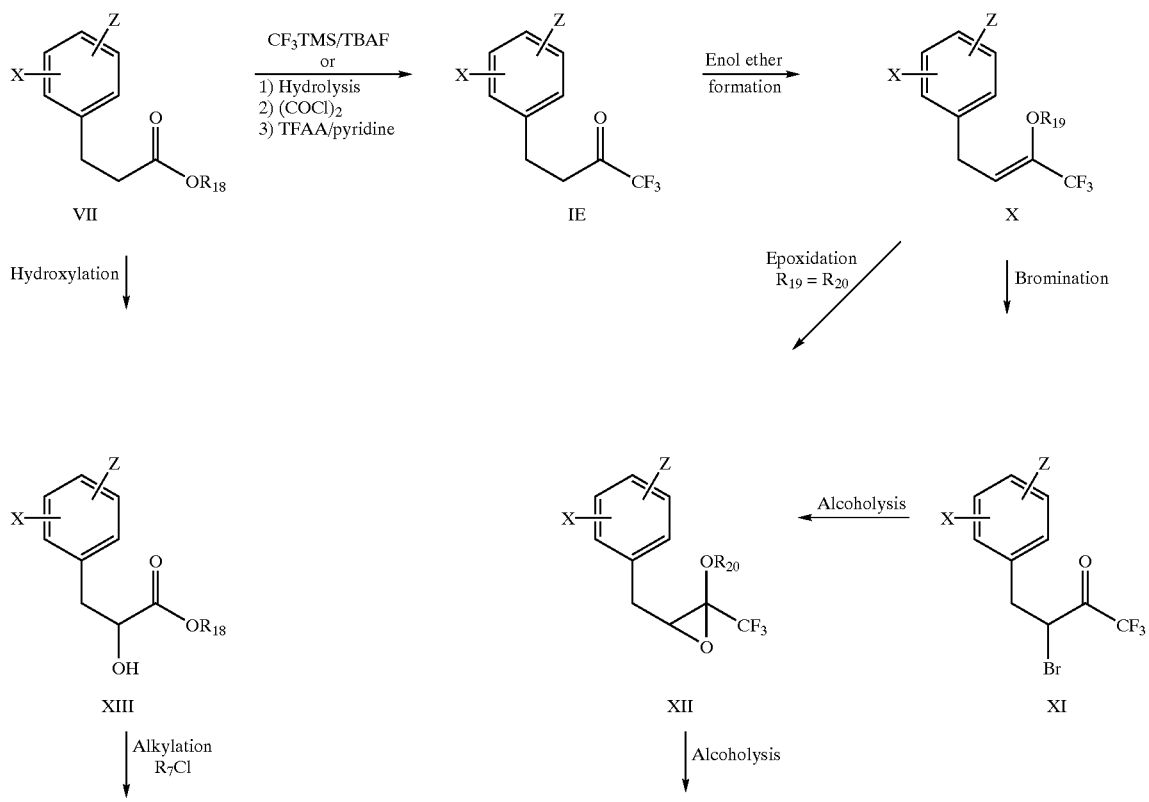

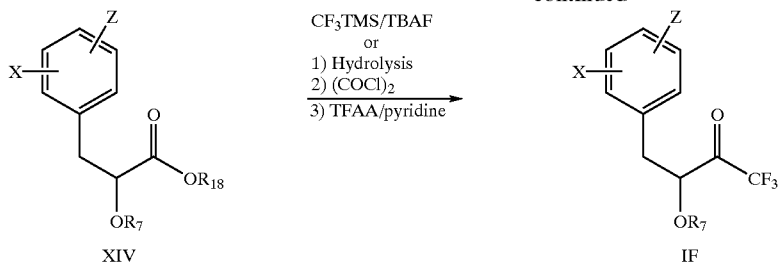

Scheme C
Preparation of α-substituted analogs cont'd:

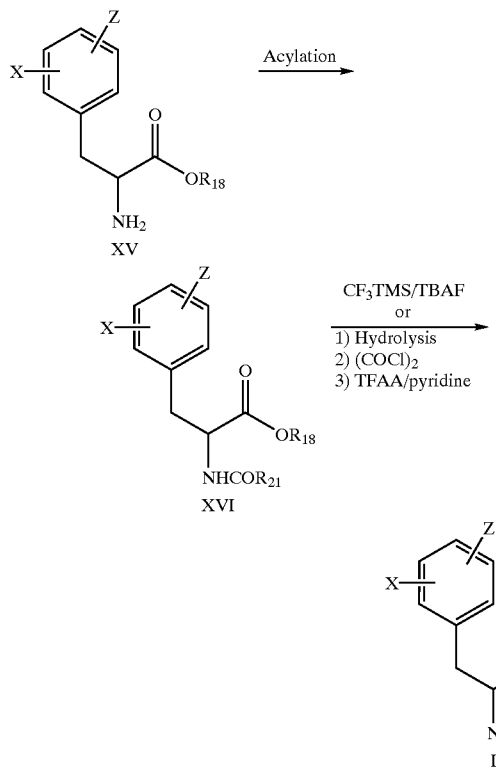

SPECIFIC EXAMPLES

The following examples further illustrate the preparation of the compounds of formula I. The examples are illustrative only and are not intended to limit the scope of the invention in any way. The following abbreviations have the indicated meanings:

| | |
|---|---|
| AcOH | acetic acid |
| EWG | electron-withdrawing groups |
| DIAD | diisopropyl azodicarboxylate |
| TFAA | trifluoroacetic anhydride |
| RT | room temperature |
| THF | tetrahydrofuran |
| TFA | trifluoroacetic acid |
| EEDQ | N-ethoxycarbonyl-2-ethoxy-1,2-dihydroxyquinoline |
| DMF | N,N-dimethylformamide |
| DEAD | diethyl azodicarboxylate |
| CPBA | m-Chloroperbenzoic acid |
| Me | $CH_3$ |
| Ph | phenyl |
| tBu | Tert-butyl |
| TBAF | tetrabutylammonium fluoride |
| $CF_3TMS$ | trifluoromethyltrimethylsilane |
| $Bu_3SnSnBu_3$ | bis-(tributyltin) |

Analytical grade solvents were used for reactions and chromatographies. Flash column chromatographies were performed on Merck silica gel 60 (230–400 Mesh) and Merck silica gel 60 $F_{254}$ 0.5 mm plates were used. All melting points were determined on a Gallenkamp melting point apparatus and were not corrected. $^1H$ NMR spectra were measured on a Bruker AMX400 (400 MHz) instruments. Chemical shifts were reported in units using the solvent as internal standard. The signals are described as s (singlet), d (doublet), t (triplet), qa (quartet), qi (quintet), m (multiplet) and br (broad). Infrared spectras were recorded on a Perkin-Elmer 781 and optical rotations were measured on a Perkin-Elmer 241 apparatus.

Example 1

4-[4-[2-[N-[2-Bis-(4-chlorophenyl)ethyl]-N-methylamino]ethoxy]phenyl]-4-(2-carboxyethylthio)-1,1,1-trifluoro-2-butanone, trifluoroacetic acid salt

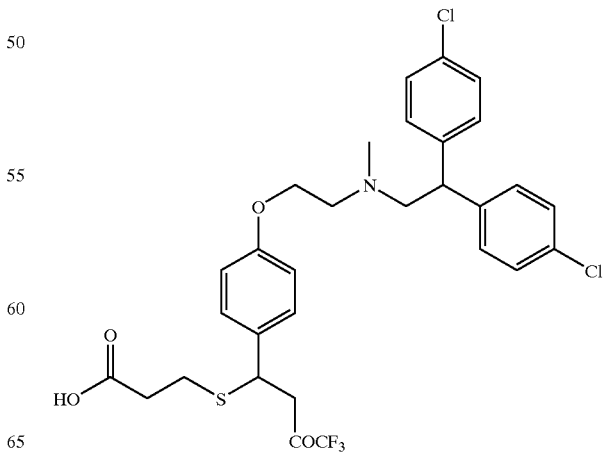

31

Bis(4-chlorophenyl)-N-methyl-N-(2-hydroxyethyl)-acetamide

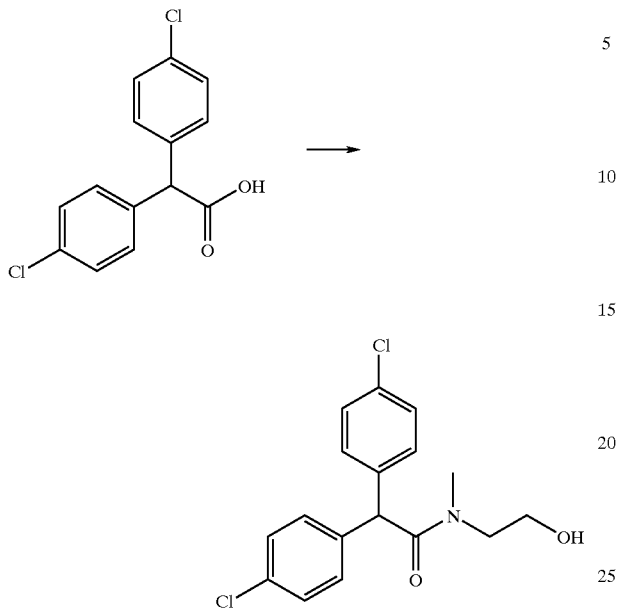

A suspension of the bis(4-chlorophenyl)acetic acid (10.40 g, 36.99 mmol) in dichloromethane (100 ml) was treated with oxalyl chloride (6.2 ml, 71.07 mmol) and dimethylformamide (1 drop). The mixture was stirred at room temperature overnight and was then concentrated under vacuum and coevaporated with toluene. The residue was dissolved in tetrahydrofuran (50 ml) and this solution was added to a mixture of 2-(methylamino)ethanol (6.0 ml, 74.7 mmol) in tetrahydrofuran (100 ml), water (50 ml) and sodium bicarbonate (10 g). The reaction was stirred at room temperature for 1 hour, then diluted with ethyl acetate. This was washed with water, HCl 1N, saturated sodium bicarbonate and brine, dried over anhydrous magnesium sulfate, filtered and concentrated. The residual white solid was crystallized from ethyl acetate to give the title compound (10.81 g, 86%).

$^1$H NMR (CDCl$_3$, δ, ppm): 2.18 (1H, br s, —OH), 2.97 and 3.05 (3H, 2 s, —NCH$_3$), 3.42 and 3.59 (2H, 2 t, J=5.2 Hz, —NCH$_2$—), 3.71 and 3.78 (2H, 2 t, J=5.2 Hz, —CH$_2$O—), 5.17 and 5.51 (1H, 2 s, —CH(Ar)$_2$), 7.15–7.20 (4H, m, aromatic H), 7.27–7.32 (4H, m, aromatic H).

Anal. Calcd. for C$_{17}$H$_{17}$NO$_2$: C, 60.37; H, 5.07; N, 4.14 Found: C, 60.23; H, 4.89; N, 4.14.

2-{2-[Bis(4-chlorophenyl)ethyl]methylamino}ethanol

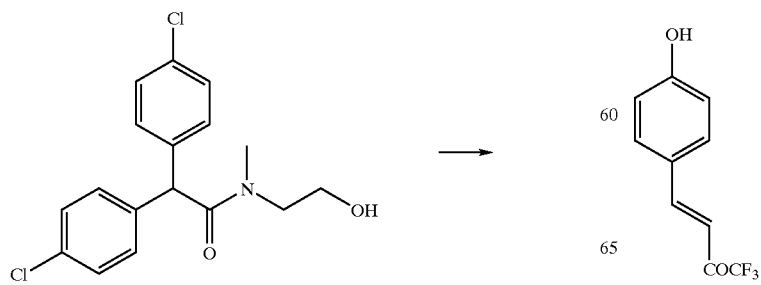

32

-continued

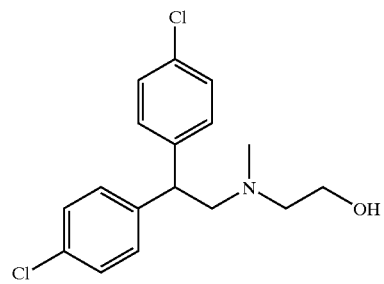

A suspension of the amide (10.80 g, 31.93 mmol) in tetrahydrofuran (35 ml) was treated with BF$_3$.Et$_2$O (4.0 ml, 31.56 mmol) and the mixture was refluxed for ~10 minutes. The mixture was then treated dropwise with Me$_2$SBH$_3$ (4.0 ml, 42.17 mmol) and the reaction was refluxed for another 15 minutes. The solvent was distilled and the residue was then heated to 110–120° C. for 1 hour. This was then treated at room temperature with 6N HCl (17 ml) and the reaction was again heated to 110–120° C. for 1 hour. The mixture was then cooled down to 0–5° C. and treated with 6M NaOH (55 ml). The mixture was extracted with ethyl ether and the organic extracts were washed with brine and dried over anhydrous magnesium sulfate, filtered and concentrated. The residue was distilled bulb to bulb to give the title material (9.03 g, 87%), b.p. 120–130° C. at 0.05 torr.

$^1$H NMR (CDCl$_3$, δ, ppm): 2.34 (3H, s, —NCH$_3$), 2.65 (2H, t, J=4.9 Hz, —CH$_2$—CH$_2$N—), 3.08 (2H, d, J=7.5 Hz, —NCH$_2$—CH—), 3.54 (2H, t, J=4.9 Hz, —CH$_2$O—), 4.26 (1H, t, J=7.5 Hz, —CH(Ar)$_2$), 7.16–7.18 (4H, m, aromatic H), 7.28–7.30 (4H, m, aromatic H).

(E)-4-[4-[2-[N-[2-Bis-(4-chlorophenyl)ethyl]-N-methylamino]ethoxy]phenyl]-1,1,1-trifluoro-3-buten-2-one

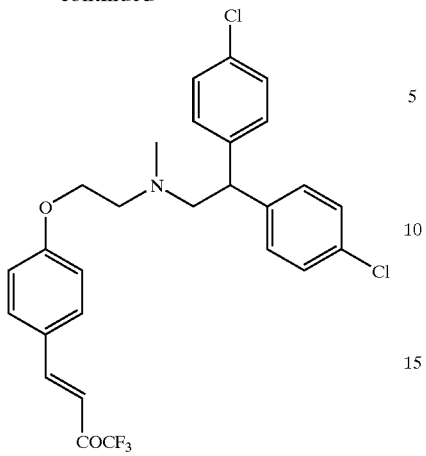

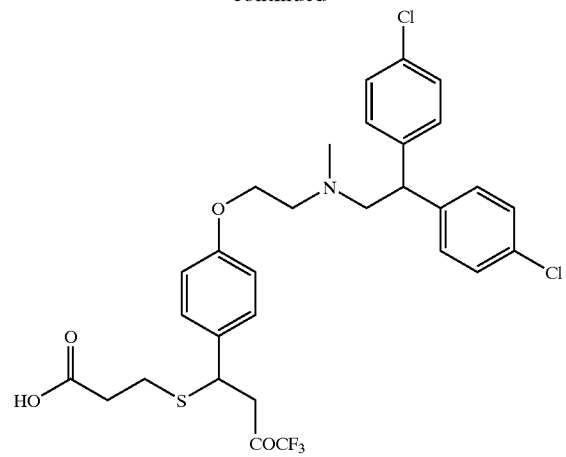

To a stirred solution of (E)4-(4-hydroxyphenyl-1,1,1-trifluoro-3-buten-2-one [Patent Application WO 99/15129] (2.91 g, 10.45 mmol), 2-{2-[bis(4-chlorophenyl)ethyl]methylamino}ethanol (3.388 g, 10.45 mmol) and triphenylphosphine (3.02 g, 11.5 mmol) in tetrahydrofuran (60 ml) at 0° C. was added diisopropylazodicarboxylate (2.27 ml, 11.5 mmol). The mixture was stirred at room temperature overnight. The solvent was evaporated and the residual oil was purified on silica gel chromatography to give the title material (2.25 g, 41%) as a yellow solid.

$^1$H NMR ($C_6D_6$, δ, ppm): 7.79 (1H, d, J=15.8 Hz, H-4), 7.13–7.11 and 6.80–6.77 (2×4 H, 2 m, H-benzhydryl), 6.94 (2H, d, J=8.8 Hz, H-phenyl), 6.67 (1H, d, J=15.8 Hz, H-3), 6.52 (2H, d, J=8.8 Hz, H-phenyl), 3.78 (1H, t, J=7.9 Hz, —CH(Ar)$_2$), 3.48 (2H, t, J=5.8 Hz, —OCH$_2$—), 2.64 (2H, d, J=7.9 Hz, —CH$_2$—CH—), 2.49 (2H, t, J=5.8 Hz, —CH$_2$N—), 2.03 (3H, s, —NCH$_3$).

4-[4-[2-[N-[2-Bis-(4-chlorophenyl)ethyl]-N-methylamino]ethoxy]phenyl]-4-(2-carboxyethylthio)-1,1,1-trifluoro-2-butanone, trifluoroacetic acid salt

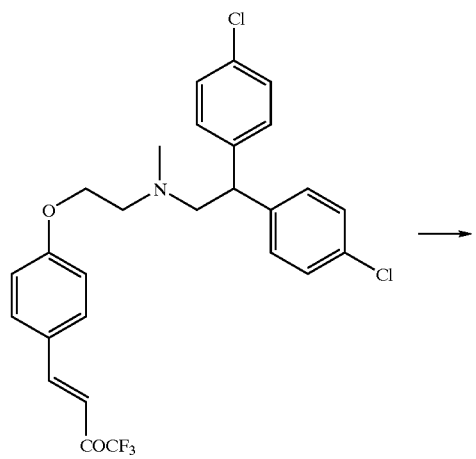

To a stirred solution of (E)4-[4-[2-[N-[2-bis-(4-chlorophenyl)ethyl]-N-methylamino]ethoxy]phenyl]-1,1,1-trifluoro-3-buten-2-one (0.125 g, 0.239 mmol) in toluene (4 ml) was added 3-mercapto-propionic acid (25 ml, 0.287 mmol). The reaction was heated to reflux for 2 hours, then the solvent was evaporated. The residue was dissolved in tetrahydrofuran and the solution was acidified with 1N HCl. Water was added and the salt precipitated. The solid was filtered and lyophilized to give the title material (0.058 g, 39%) as a white fluffy solid.

$^1$H NMR ($C_3D_6O$, δ, ppm): 7.41 (4H, d, aromatic H), 7.28–7.25 (6H, m, aromatic H), 6.79 (2H, d, aromatic H), 4.72 (1H, t, J=7.6 Hz, benzhydryl H), 4.38 (2H, t, J=4.4 Hz, —OCH$_2$—), 4.26 (1H, br t, —CH—S—), 4./09 (2H, d, J=7.5 Hz, —N—C$\underline{H}_2$—CH—), 3.72 (2H, br t, —N—C$\underline{H}_2$—CH$_2$—), 2.66–2.39 (4H, m, —S(CH$_2$)$_2$—), 2.33 (1H, br dd, J=14.8 and 7.2 Hz, —CH$_2$COCF$_3$), 2.22 (1H, dd, J=14.8 and 5.2 Hz, —CH$_2$COCF$_3$).

IR (δ, cm$^{-1}$): 3400.28, 2929.67, 1717.23.

MS (ESI): 628.05 (MH)$^+$, 646.07 (MH+H$_2$O)$^+$.

Example 2

4-[4-[2-[N-[2-Bis-(4-chlorophenyl)ethyl]-N-methylamino]ethoxy]phenyl]-4-(4-carboxybutyl)-1,1,1-trifluoro-2-butanone, trifluoroacetic acid salt

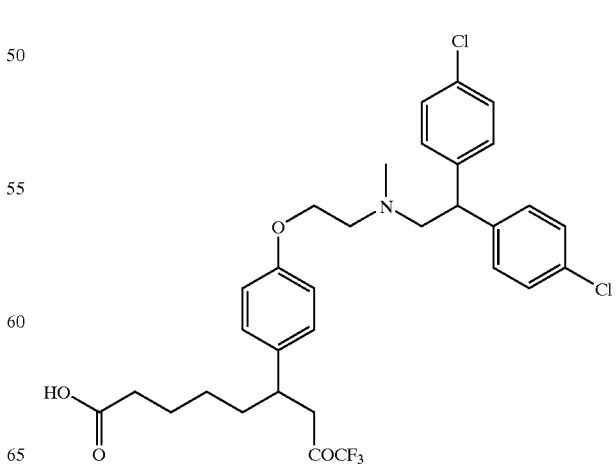

35
Methyl tert-butyl adipate

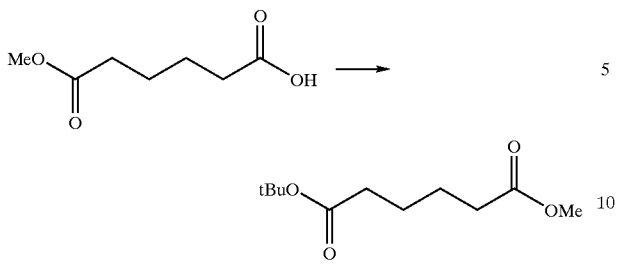

To a stirred solution of mono-methyl adipate (8.0 g, 49.44 mmol) in dichloromethane (60 mL) was added oxalyl chloride (13.1 ml, 149.8 mmol) followed by ten drops of dimethylformamide. The reaction was stirred for 1 hour, then the solvent was evaporated and dried under vacuum for 20 minutes.

The crude acid chloride was then dissolved in dichloromethane (70 ml) and pyridine (6.0 ml, 77.6 mmol) was added followed by tert-butanol (5.0 ml, 87 mmol). The mixture was refluxed for 1 hour, then washed with water, dried over anhydrous magnesium sulfate, filtered and concentrated. The crude residue was filtered on a silica gel pad (hexane/ethyl acetate 1:1) and afforded the title material (9.9 g, 92%) as an oil.

$^1$H NMR ($C_6D_6$, δ, ppm): 1.48 (9H, s, —OtBu), 1.57–1.61 (4H, m, —$(CH_2)_2$—), and 2.10–2.13 (4H, m, 2×—$CH_2COO$—), 3.41 (3H, s, —OMe).

Mono-tert-butyl adipate

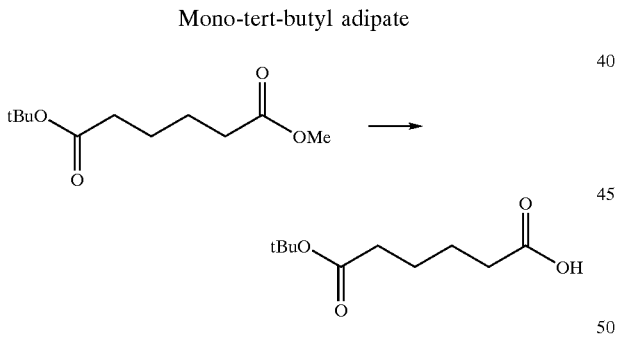

A solution of methyl tert-butyl adipate (9.9 g, 45.8 mmol) in ethanol (70 ml) and tetrahydrofuran (70 ml) was stirred with aqueous sodium hydroxide (1N, 137 ml, 137 mmol) at 0° C. for 2 hours. The mixture was then diluted with water and washed with dichloromethane (2×). The mixture was diluted with dichloromethane and acidified with aqueous hydrochloric acid (1N, 150 ml). The organic layer was separated and the aqueous phase was extracted with dichloromethane. The combined organic layers were dried over anhydrous magnesium sulfate, filtered and concentrated to give the title material (7.82 g, 85%).

$^1$H NMR ($C_6D_6$, δ, ppm): 1.48 (9H, s, —OtBu), 1.52 (4H, m, —$(CH_2)_2$—), 2.05–2.10 (4H, m, 2×—$CH_2COO$—).

36
1-Methyl, 8-tert-butyl 3-oxo-1,8-octanedioate

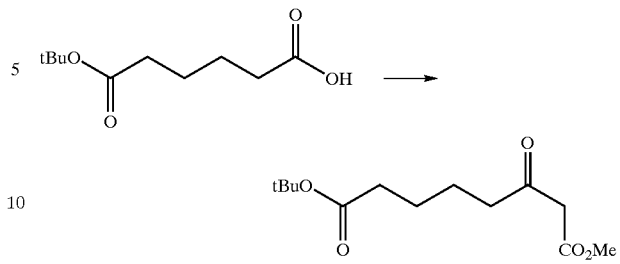

A solution of mono-tert-butyl adipate (7.8 g, 37.5 mmol) in dichloromethane (175 ml) was treated with oxalyl chloride (9.8 ml, 112.5 mmol) followed by ten drops of dimethylformamide. The reaction was stirred at room temperature for 1 hour. The solvent was evaporated and the residue was dried under vacuum.

To a solution of 2,2-dimethyl-1,3-dioxane-4,6-dione (5.42 g, 37.6 mmol) in dichloromethane (30 ml) at 0° C. was added pyridine (6.1 ml, 75 mmol) followed by the crude acid chloride in a solution of dichloromethane (30 ml). The reaction was stirred at 0° C. for 1 hour and at room temperature for 2 hours. The reaction was then washed with water and dried over anhydrous magnesium sulfate, filtered and concentrated. The crude residue was then dissolved in methanol and refluxed for 3 hours. The solvent was evaporated and the residue was purified by silica gel chromatography to give the title material (5.82 g, 60%) as an oil.

1-[2-{2-[Bis(4-chlorophenyl)ethyl]methylamino}ethoxy]-4-bromo-benzene

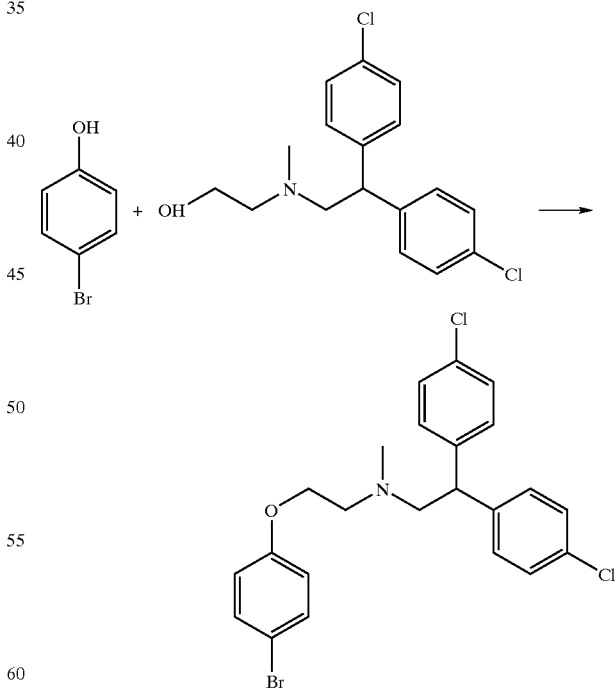

A solution of 4-bromophenol (3.0 g, 17.3 mmol), 2-{2-[bis(4-chlorophenyl)ethyl]methylamino}ethanol (5.61 g, 17.3 mmol) and triphenylphosphine (4.98 g, 19 mmol) in tetrahydrofuran (60 ml) was treated with diisopropyl azodicarboxylate (3.73 ml, 19 mmol) at 0° C. The mixture was stirred at room temperature for 3 hours and the solvent was evaporated. The residue was purified by silica gel chromatography to give the title material (4.11 g, 50%).

$^1$H NMR (C$_6$D$_6$, δ, ppm): 2.01 (3H, s, —NMe), 2.47 (2H, t, J=5.9 Hz, —CH$_2$—CH$_2$N—), 2.63 (2H, d, J=8.0 Hz, —CH—CH$_2$N—), 3.41 (2H, t, J=5.9 Hz, —CH$_2$O—), 3.77 (1H, t, J=8.0 Hz, —CH(Ar)$_2$), 6.42 (2H, d, J=9.1 Hz, aromatic H), 6.77 (4H, d, J=8.1 Hz, aromatic H), 7.11 (4H, d, J=8.1 Hz, aromatic H), 7.22 (2H, d, J=9.1 Hz, aromatic H).

1-[2-{2-[Bis(4-chlorophenyl)ethyl] methylamino}ethoxy]-4-tributylstannyl-benzene

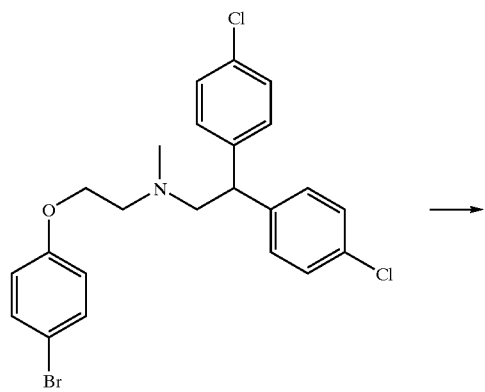

To a stirred solution of 1-[2-{2-[bis(4-chlorophenyl) ethyl]methylamino}ethoxy]-4-bromo-benzene (1.0 g, 2.09 mmol) in dioxane (20 mL) was added bis-(tributyltin) (1.69 ml, 3.35 mmol) and palladium(0) tetrakis (triphenylphosphine) (100 mg). The mixture was refluxed overnight and the solvent was evaporated. The residue was purified by silica gel chromatography to give the title material (1.18 g, 82%).

$^1$H NMR (C$_6$D$_6$, δ, ppm): 0.87 (9H, t, J=7.2 Hz, 3x—CH3), 1.11–1.17 (6H, m, 3x—CH2—), 1.24–1.30 (6H, m, 3x—CH2—), 1.44–1.64 (6H, m, 3x—CH2—), 2.05 (3H, s, —NMe), 2.58 (2H, t, J=5.9 Hz, —CH2CH2N—), 2.68 (2H, d, J=8.2 Hz, —CH—CH2N—), 3.68 (2H, t, J=5.9 Hz, —OCH2—), 3.81 (1H, t, J=8.2 Hz, —CH(Ar)2), 6.79 (4H, d, J=8.1 Hz, aromatic H), 6.95 (2H, d, J=8.6 Hz, aromatic H), 7.12 (4H, d, J=8.6 Hz, aromatic H), 7.52 (2H, d, J=8.1 Hz, aromatic H).

Methyl 3-[4-[2-[N-[2-bis-(4-chlorophenyl)ethyl]-N-methylamino]ethoxy]phenyl]-3-(4-tertbutoxycarbonylbutyl)-2(E)-propenoate and methyl 3-[4-[2-[N-[2-bis-(4-chlorophenyl)ethyl]-N-methylamino]ethoxy]phenyl]-3-(4-tertbutoxycarbonylbutyl)-2(Z)-propenoate

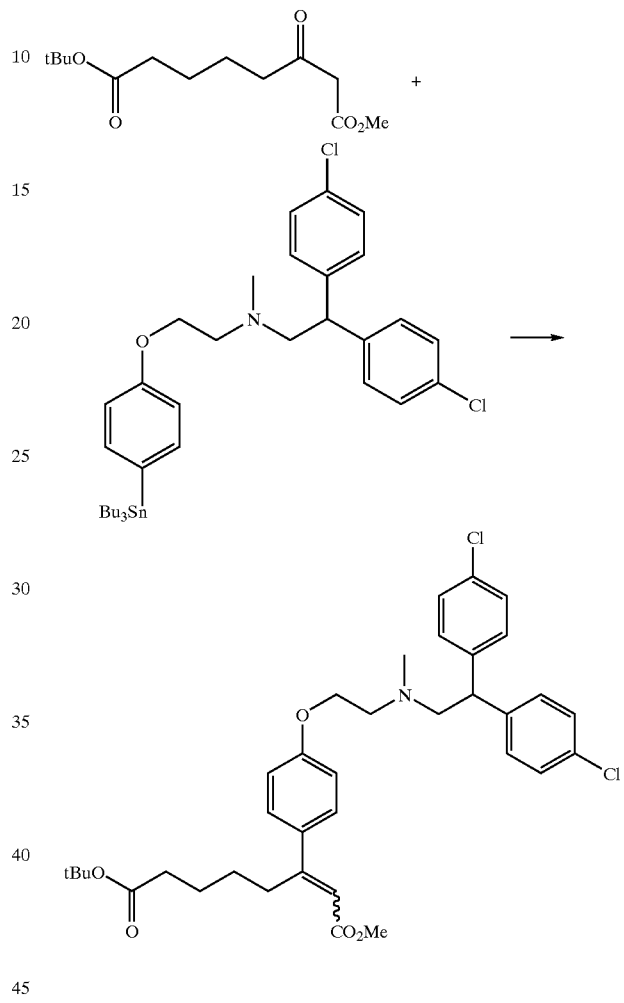

To a stirred solution of 1-methyl, 8-tert-butyl 3-oxo-1,8-octanedioate (0.444 g, 1.72 mmol) in dichloromethane (12 ml) at −78° C. was added diisopropylamine (1.203 ml, 8.58 mmol) and the mixture was stirred for 15 minutes. Triflic anhydride (0.347 ml, 2.06 mmol) was then added at −78° C. and the reaction was stirred for 1 hour. The mixture was then quenched with saturated sodium bicarbonate and diluted with dichloromethane. The organic phase was washed with water and dried over anhydrous magnesium sulfate, filtered and concentrated. The residue was dissolved in N-methylpyrrolidinone (15 ml) and triphenylarsine (50 mg), tris(dibenzylidene-acetone)dipalladium(0) (50 mg) and 1-[2-{2-[bis(4-chlorophenyl)ethyl]methylamino}ethoxy]-4-tributylstannyl-benzene (1.30 g, 1.89 mmol) were added. The reaction was stirred at ~100° C. overnight, then diluted with ethylacetate and washed with water. The organic layer was dried over anhydrous magnesium sulfate, filtered and concentrated. The residue was purified by silica gel chromatography to give the title material (0.902 g, 82%) as a mixture of cis and trans isomers.

39

Methyl 3-[4-[2-[N-[2-bis-(4-chlorophenyl)ethyl]-N-methylamino]ethoxy]phenyl]-3-(5-tertbutoxycarbonylpentyl)-propanoate

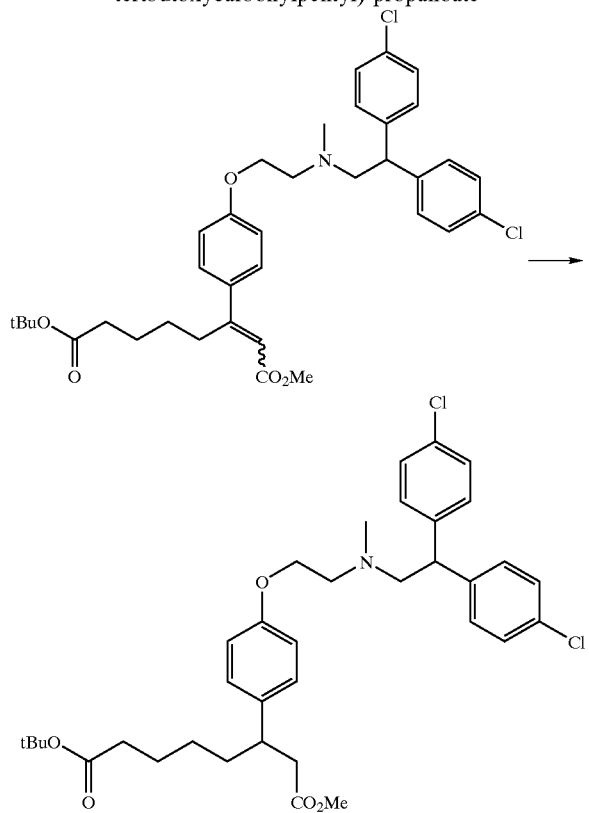

A solution of methyl 3-[4-[2-[N-[2-bis-(4-chlorophenyl)ethyl]-N-methylamino]ethoxy]phenyl]-3-(4-tertbutoxycarbonylbutyl)-2(E)-propenoate and methyl 3-[4-[2-[N-[2-bis-(4-chlorophenyl)ethyl]-N-methylamino]ethoxy]phenyl]-3-(4-tertbutoxycarbonylbutyl)-2(Z)-propenoate (0.360 g, 0.512 mmol) in ethyl acetate (20 ml) and ethanol (10 ml) was hydrogenated (10 psi) in presence of 5% rhodium on carbon (~220 mg). The mixture was filtrate and the solvents were evaporated. The residue was purified by prep TLC plates to give the title material (36 mg, 10%).

4-[4-[2-[N-[2-Bis-(4-chlorophenyl)ethyl]-N-methylamino]ethoxy]phenyl]-4-(4-tertbutoxycarbonylbutyl)-1,1,1-trifluoro-2-butanone

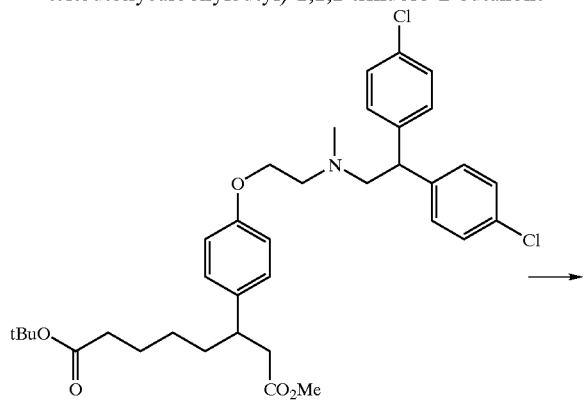

40

-continued

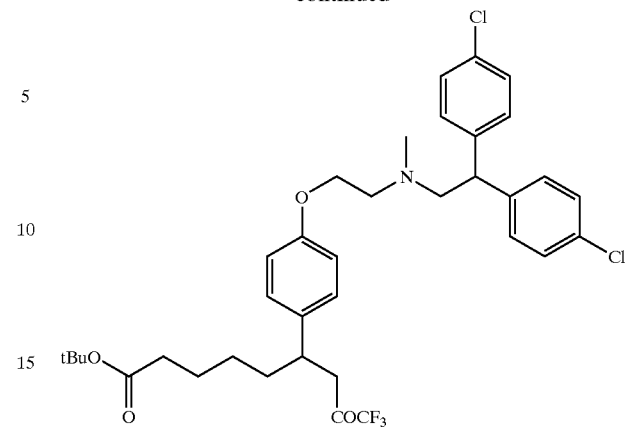

To a stirred solution of methyl 3-[4-[2-[N-[2-bis-(4-chlorophenyl)ethyl]-N-methylamino]ethoxy]phenyl]-3-(4-tertbutoxycarbonylbutyl)-propanoate (0.036 g, 0.056 mmol) in toluene (2 ml) at −78° C. was added trifluoromethyltrimethylsilane (17 μL, 0.112 mmol) and a catalytic amount of dried tetrabutylammonium fluoride. The mixture was warmed to room temperature and stirred for 3 hours. The solvent was evaporated and the residue was purified by silica gel chromatography (toluene/ethyl acetate) to give the title material (12 mg, 31%).

$^1$H NMR (C$_6$D$_6$, δ, ppm): 1.12, 1.36 and 1.47–1.63 (2H, 2H and 2H, 3 m, —(CH$_2$)$_3$—), 1.49 (9H, s, —tBu), 2.12 (2H, t, J=7.2 Hz, —CH$_2$—COO—), 2.16 (3H, s, —NMe), 2.49 (1H, dd, J=18.1 and 5.9 Hz, —CH$_2$CO—), 2.63–2.69 (3H, m, —CH$_2$CO— and —NCH$_2$CH$_2$—), 2.78 (2H, d, J=7.9 Hz, —NCH$_2$CH—), 3.07 (1H, m, —C$_6$H$_4$—CH—), 3.71 (2H, t, J=6.1 Hz, —CH$_2$O—), 3.91 (1H, t, J=8.0 Hz, —CH(Ar)$_2$), 6.83 and 6.89 (2×2H, 2d, J=8.6 Hz, aromatic H), 6.95 and 7.22 (2×4H, 2 d, J=8.5 Hz, aromatic H).

4-[4-[2-[N-[2-Bis-(4-chlorophenyl)ethyl]-N-methylamino]ethoxy]phenyl]-4-(4-carboxybutyl)-1,1,1-trifluoro-2-butanone, trifluoroacetic acid salt

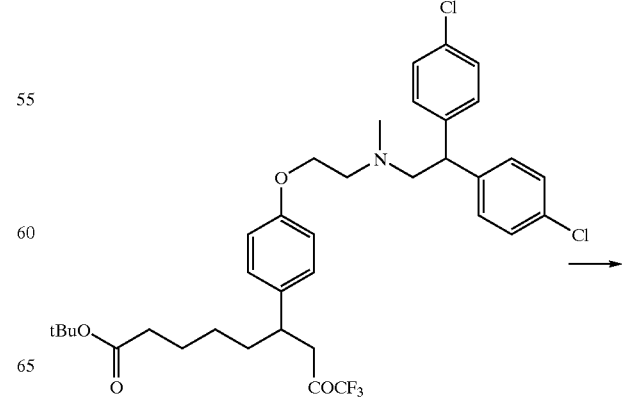

41
-continued

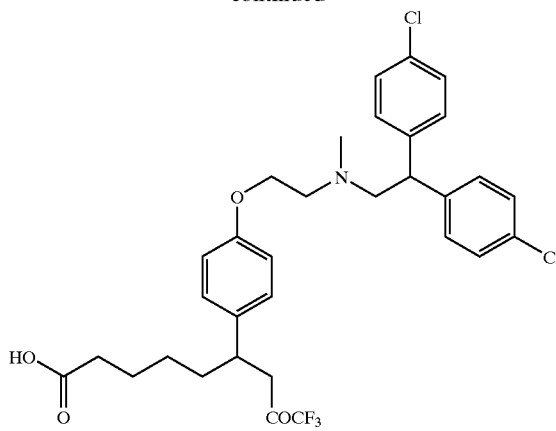

4-[4-[2-[N-[2-Bis-(4-chlorophenyl)ethyl]-N-methylamino]ethoxy]phenyl]-4-(4-tertbutoxycarbonylbutyl)-1,1,1-trifluoro-2-butanone (12 mg, 0.018 mmol) was dissolved in a solution of trifluoroacetic acid in dichloromethane (1 ml, 15%, v:v) and the reaction was stirred for 1 hour. The solvents were co-evaporated with toluene (3×) and the residue was lyophilized to give the title material (9 mg, 80%). MS (ESI): 624 (M+H)$^+$; 622 (M−H)$^-$.

Example 3

4-[4-[2-[N-[2-Bis-(4-chlorophenyl)ethyl]-N-methylamino]ethoxy]phenyl]-3-(5-carboxypentyl)-1,1,1-trifluoro-2-butanone, trifluroacetic acid salt

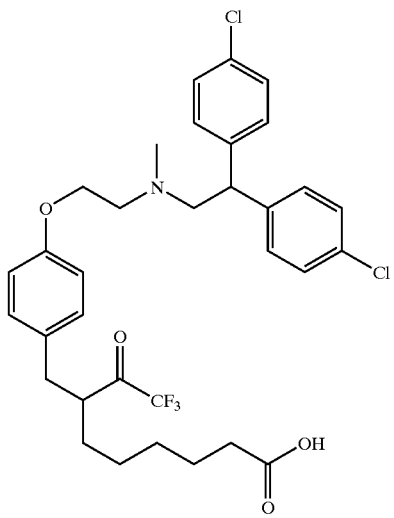

42

4-[4-[2-[N-[2-Bis-(4-chlorophenyl)ethyl]-N-methylamino]ethoxy]phenyl]-3-methoxycarbonyl-1,1,1-trifluoro-2-butanone

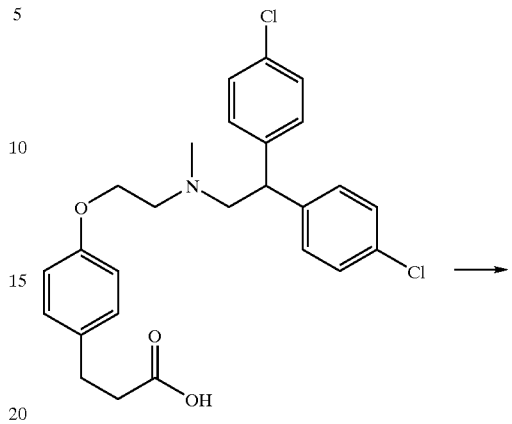

To a solution of 4-[4-[2-[N-[2-bis-(4-chlorophenyl)ethyl]-N-methylamino]ethoxy]phenyl]propanoic acid (9.04 g, 17.76 mmol) in dichloromethane (150ml) was added slowly oxalyl chloride (3.1 ml, 35.52 mmol) and two small drops of DMF. The mixture was stirred at room temperature for 1.5 hours and the excess reagent and solvent were removed in vacuo. The residue was dissolved in dry toluene (150 ml), cooled to 0° C. and treated with trifloroacetic anhydride (7.4 ml, 53.28 mmol). To this mixture at 0° C. was added dropwise pyridine (2.8 ml, 35.52 mmol) over 0.5 hours. The resulting mixture was stirred at room temperature for 3 hours, treated with methanol (20 ml), then stirred for another 0.5 hours, diluted with ethyl acetate (300 ml), washed with water, aqueous sodium bicarbonate, brine, dried over sodium sulfate and concentrated in vacuo. The residue was chromatographed on silica gel (hexane:ethyl acetate= 8:2–7:3) to give the title material (5.6 g, 54%) as a yellow oil.

Treatment of the above free amine with anhydrous hydrogen chloride (1.0M in ether) gave the hydrochloride salt as a white foam.

Anal. Calcd. for $C_{29}H_{29}NCl_2F_3O_4 \cdot HCl \cdot 2H_2O$: C, 53.18%; H, 5.08%; N, 2.14%; Found: C, 53.22%; H, 4.87%; N, 2.13%.

43

4-[4-[2-[N-[2-Bis-(4-chlorophenyl)ethyl]-N-methylamino]ethoxy]phenyl]-3-methoxycarbonyl-1,1,1-trifluoro-2-tert-butyldimethylsilyloxy-2(E and Z)-butene

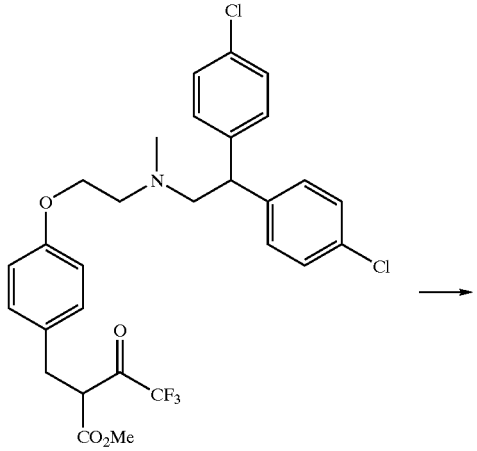

44

4-[4-[2-[N-[2-Bis-(4-chlorophenyl)ethyl]-N-methylamino]ethoxy]phenyl]-3-hydroxymethyl-2-tert-butyldimethylsilyloxy-1,1,1-trifluoro-2(E and Z)-butene

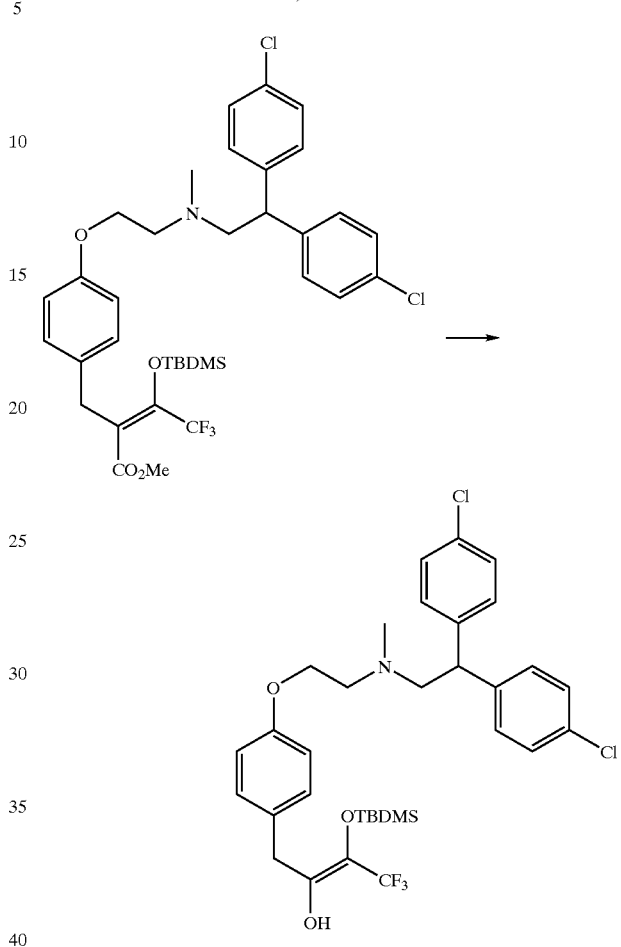

To a solution of 4-[4-[2-[N-[2-bis-(4-chlorophenyl)ethyl]-N-methylamino]ethoxy]phenyl]-3-methoxycarbonyl-1,1,1-trifluoro-2-butanone (5.6 g, 9.61 mmol) and tert-butyl dimethylsilyl chloride (2.9 g, 19.22 mmol) in dimethylforamide (60 ml) at 0° C. was added dropwise triethylamine (3 ml, 22.1 mmol). The mixture was stirred at room temperature for 1 hour, poured into saturated aqueous sodium bicarbonate (500 ml). The mixture was stirred for 10 minutes and extracted with diethyl ether. The organic phase was washed with aqueous sodium bicarbonate, brine, dried over magnesium sulfate and concentrated in vacuo. Chromatography of the residue on silica gel (hexane:ethyl acetate=90:10–80:20) gave the title material (5.5 g, 81%) as a pale yellow oil and as a mixture of isomers.

$^1$H NMR ($C_6D_6$, δ, ppm): 0.13 and 0.17 (6H, 2s, 2x—Me), 0.85 and 0.96 (9H, 2 s, —tBu), 2.04 (3H, s, —NMe), 2.54 (2H, t, J=5.9 Hz, —NCH$_2$CH$_2$—), 2.67 (2H, d, J=7.8 Hz, —NCH$_2$—CH—), 3.28 and 3.26 (3H, 2 s, —OMe), 3.58 (2H, t, J=5.9 Hz, —OCH$_2$—), 3.80 (3H, m, —CH(Ar)$_2$ and —CH$_2$—C=C=), 6.74 (2H, d, J=8.5 Hz, aromatic H), 6.79 (4H, d, J=8.4 Hz, aromatic H), 7.12 (4H, d, J=8.4 Hz, aromatic H), 7.19 (2H, d overlapped by $C_6D_6$, aromatic H).

Anal. Calcd. for $C_{35}H_{42}NCl_2F_3O_4Si \cdot 0.2H_2O$: C, 60.03%; H, 6.10%; N, 2.00%; Found: C, 59.94%; H, 6.08%; N, 2.02%.

To a solution of 4-[4-[2-[N-[2-bis-(4-chlorophenyl)ethyl]-N-methylamino]ethoxy]phenyl]-3-methoxycarbonyl-1,1,1-trifluoro-2-tert-butyldimethylsilyloxy-2-butene (3.1 g, 4.45 mmol) in toluene (35 ml) at −78° C. was added dropwise diisopropylaluminum hydride (1M in toluene, 17.8 ml, 17.8 mmol). The mixture was stirred at this temperature for 0.5 hours, quenched with aqueous ammonium chloride. After 15 minutes at room temperature, the mixture was filtered and washed with ethyl acetate. The filtrate was washed with saturated aqueous ammonium chloride, brine, dried over magnesium sulfate and concentrated in vacuo. The residue was chromatographed on silica gel (hexane:ethyl acetate=75:25) to give the title material (2.61 g, 87%) as a pale yellow oil.

$^1$H NMR ($C_6D_6$, δ, ppm): 0.16 and 0.43 (6H, 2 s, 2x—CH$_3$), 0.95 (9H, s, —tBu), 2.05 and 2.06 (3H, 2 s, —NMe), 2.56 and 2.57 (2H, 2 t, J=5.8 Hz, —NCH$_2$CH$_2$—), 2.68 (2H, d, J=7.8 Hz, —NCH$_2$CH—), 3.62 (2H, t, J=5.8 Hz, — OCH$_2$—), 3.70 (2H, br s, —CH$_2$—C=C—), 3.80 (1H, t, J=7.8 Hz, —CH(Ar)$_2$), 4.08 and 4.01 (2H, 2s, —CH$_2$OH), 6.72–6.80, 6.91–6.93 and 7.10–7.14 (2H, 4H and 4H, 3 m, aromatic H).

45

3-[4-[2-[N-[2-Bis-(4-chlorophenyl)ethyl]-N-methylamino]ethoxy]phenylmethyl]-1,1,1-trifluoro-3-buten-2-one

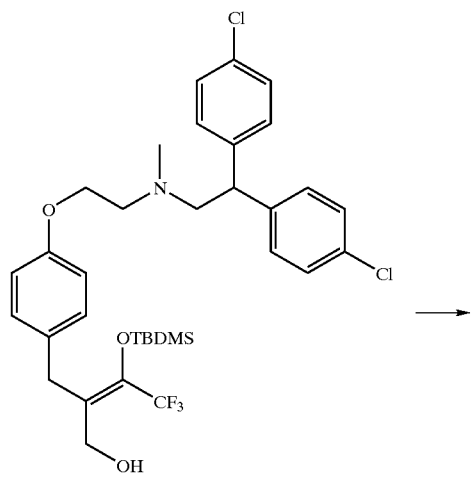

46

4-[4-[2-[N-[2-Bis-(4-chlorophenyl)ethyl]-N-methylamino]ethoxy]phenyl]-3-(5-ethoxycarbonylpentyl)-1,1,1-trifluoro-2-butanone

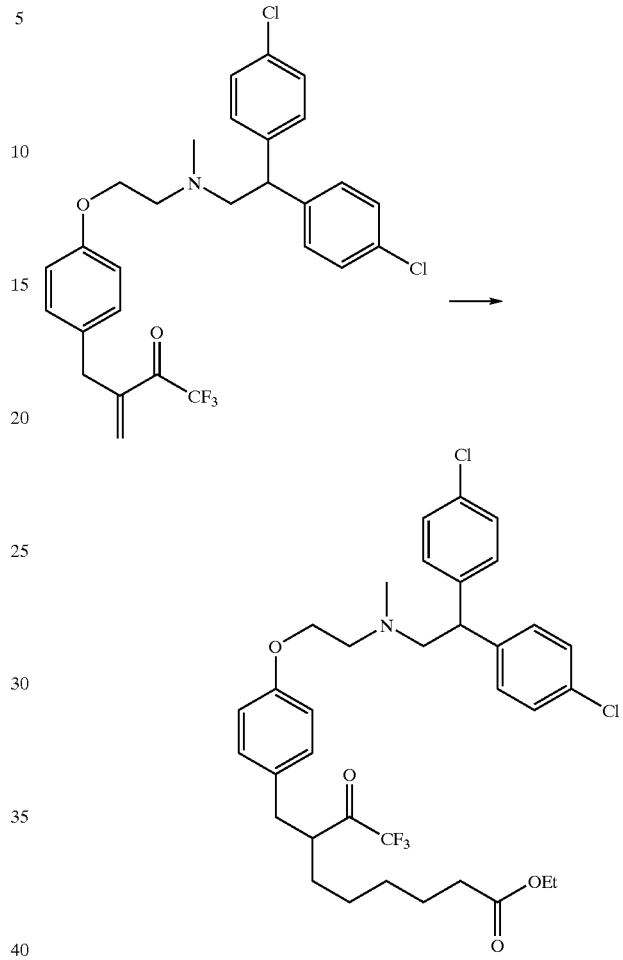

4-[4-[2-[N-[2-Bis-(4-chlorophenyl)ethyl]-N-methylamino]ethoxy]phenyl]-3-hydroxymethyl-2-tert-butyldimethylsilyloxy-1,1,1-trifluoro-2-butene (1.06 g, 1.58 mmol) in trifluoroacetic acid (10 ml) was stirred at room temperature for 0.5 hours, concentrated in vacuo, diluted with ethyl acetate, washed twice with sodium bicarbonate, brine, dried over magnesium sulfate and concentrated in vacuo. The residue was chromatographed on silica gel (dichloromethane:ethyl acetate=100:0–95:5) to give the title material (721 mg, 85%) as a pale yellow oil. Treatment of the above free amine with anhydrous hydrogen chloride (1.0 M in ether) gave the hydrochloride salt as a white foam.

$^1$H NMR ($C_6D_6$, δ, ppm): 2.05 (3H, s, —NMe), 2.56 (2H, t, J=5.9 Hz, —NC$\underline{H}_2$—CH$_2$—), 2.68 (2H, d, J=7.8 Hz, —NC$\underline{H}_2$CH—), 3.31 (2H, s, —CH$_2$—C=), 3.60 (2H, t, J=5.9 Hz, —CH$_2$O—), 3.80 (1H, t, J=7.8 Hz, —CH(Ar)$_2$), 5.43 and 5.93 (2×1H, 2 s, =CH$_2$), 6.71 (2H, J=8.6 Hz, aromatic H), 6.79 (4H, d, J=8.4 Hz, aromatic H), 6.86 (2H, d, J=8.5 Hz, aromatic H), 7.12 (4H, d, J=8.4 Hz, aromatic H).

Anal. Calcd. for $C_{28}H_{26}NCl_2F_3O_2 \cdot HCl \cdot H_2O$: C, 57.44%; H, 4.78%; N, 2.45%; Found: C, 57.5%; H, 4.78%; N 2.45%.

To a freshly prepared 4-ethoxycarbonylbutylzinc iodide (1.6 ml in THF, 0.96 mmol) at −40° C. was added slowly trimethylsilylmethyl lithium (1M in pentane, 1.2 ml, 1.2 mmol). The mixture was stirred at this temperature for 1 hour and 1.5 ml of which was transferred to a flask at −78° C. To this were then added 1-methyl-2-pyrrolidinone (0.09 ml), trimethylsilyl bromide (0.09 ml) and 3-[4-[2-[N-[2-bis-(4-chlorophenyl)ethyl]-N-methylamino]ethoxy]phenylmethyl]-1,1,1-trifluoro-3-buten-2-one (200 mg, 0.37 mmol) dissolved in THF (1 ml). The resulting mixture was stirred at −30° C. for 3 hours, quenched with saturated aqueous ammonium chloride, diluted with ethyl acetate, washed with saturated aqueous ammonium chloride, brine, dried over magnesium sulfate and concentrated in vacuo. The residue was dissolved in THF (5 ml), cooled to −20° C. and treated with tetrabutylammonium fluoride/acetic acid (0.4 ml in THF, 0.37 mmol). The mixture was stirred at this temperature for 0.5 hours, quenched with water. After 10 minutes at room temperature, the mixture was diluted with ethyl acetate, washed with aqueous sodium bicarbonate, brine, dried over magnesium sulfate and concentrated in vacuo. Chromatography of the residue on silica gel (hexane:ethyl acetate=85:15) gave the title compound (148 mg, 60%) as a colorless oil.

Treatment of the above free amine with anhydrous hydrogen chloride (1.0 M in ether) gave the hydrochloride salt as a white foam.

Anal. Calcd. for $C_{35}H_{40}NCl_2F_3O_4 \cdot HCl \cdot 1.3H_2O$: C, 57.86%; H, 5.75%; N, 1.93%; Found: C, 57.82%; H, 5.75%; N, 2.02%.

4-[4-[2-[N-[2-Bis-(4-chlorophenyl)ethyl]-N-methylamino]ethoxy]phenyl]-3-(5-carboxypentyl)-1,1,1-trifluoro-2-butanone

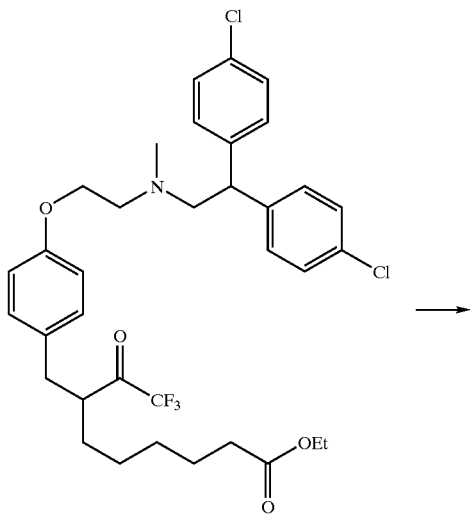

A solution of 4-[4-[2-[N-[2-bis-(4-chlorophenyl)ethyl]-N-methylamino]ethoxy]phenyl]-3-(5-ethoxycarbonylpentyl)-1,1,1-trifluoro-2-butanone (148 mg, 0.22 mmol) in ethanol (4 ml) and water (1 ml) was treated with potassium hydroxide (28 mg, 0.44 mmol) dissolved in water (1 ml). The mixture was stirred at 50° C. for 2 hours, cooled to room temperature, adjusted to pH 3 with 1N HCl and extracted with ethyl acetate. The organic layer was washed with brine, dried over magnesium sulfate and concentrated in vacuo. The residue was purified by preparative HPLC (C-18, acetonitrile-water-trifluoroacetic acid) to give the trifluoacetic acid salt of the title compound (30 mg, 18%) as a white foam.

Anal. Calcd. for $C_{33}H_{36}NCl_2F_3O_4 \cdot CF_3COOH \cdot 0.6H_2O$: C, 55.07%; H, 5.04%; N, 1.84%; Found: C, 54.94%; H, 4.81%; N, 1.89%.

Example 4

4-[4-[2-[N-[2-Bis-(4-chlorophenyl)ethyl]-N-methylamino]ethoxy]phenyl]-3-(4-carboxybutyl)-1,1,1-trifluoro-2-butanone, trifluoacetic acid salt

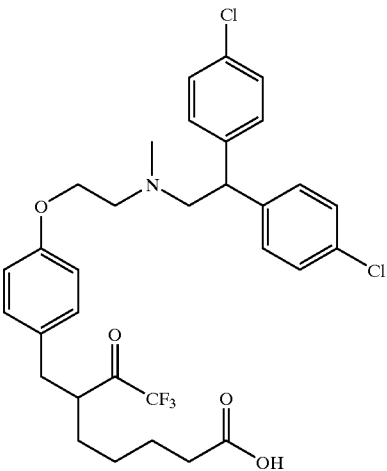

tert-Butyl 4-iodobutanoate

To a solution of concentrated sulfuric acid (2 ml) and 1,4-dioxane (20 ml) in a pressure bottle at 0° C. were added 4-iodobutanoic acid (5.5 g, 25.7 mmol) and isobutene (30 ml). The mixture was stirred at room temperature for 3 days, cooled to 0° C. and poured slowly into an aqueous solution (120 ml) of sodium bicarbonate (10 g). The mixture was stirred at room temperature for 15 minutes and extracted with diethyl ether. The organic phase was washed three times with brine, dried over sodium sulfate and concentrated in vacuo. The residue was chromatographed on silica gel (hexane:dichloromethane=1:1) to give the title compound (4.24 g, 61%) as a pale yellow liquid.

$^1$H NMR (CDCl$_3$, δ, ppm): 1.45 (9H, s, —tBu), 2.09 (2H, qi, J=7.0 Hz, —CH$_2$—C$\underline{H}_2$—CH$_2$—), 2.35 (2H, t, J=7.1 Hz, —C$\underline{H}_2$—CO$_2$tBu), 3.23 (2H, t, J=6.9 Hz, —CH$_2$I).

4-[4-[2-[N-[2-Bis-(4-chlorophenyl)ethyl]-N-methylamino]ethoxy]phenyl]-3-(4-t-butoxycarbonylbutyl)-1,1,1-trifluoro-2-butanone

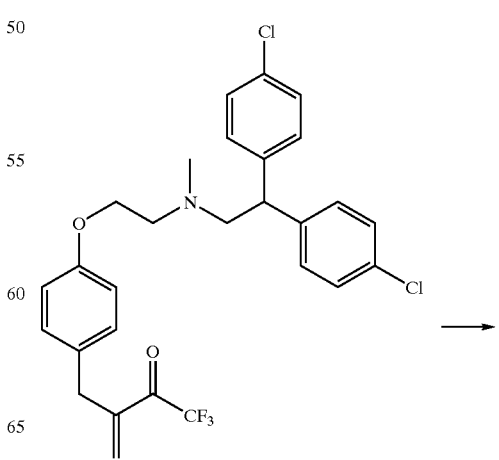

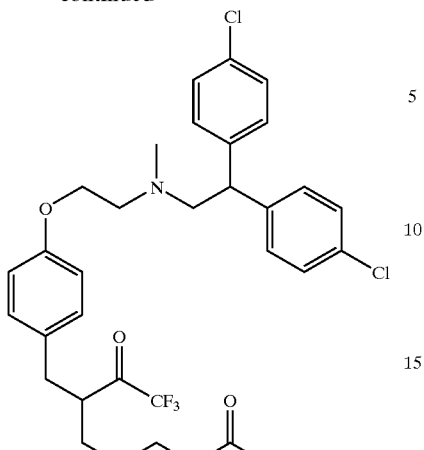

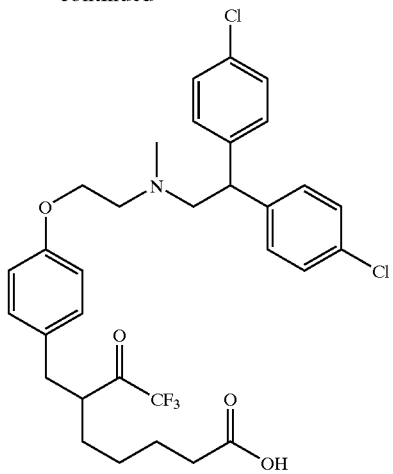

3-[4-[2-[N-[2-Bis-(4-chlorophenyl)ethyl]-N-methylamino]ethoxy]phenylmethyl]-1,1,1-trifluoro-3-buten-2-one (500 mg, 0.9 mmol) and 3-(tert-butoxycarbonyl)propylzinc iodide were reacted by the similar procedure described in Example 3 for the preparation of 4-[4-[2-[N-[2-bis-(4-chlorophenyl)ethyl]-N-methylamino]ethoxy]phenyl]-3-(5-ethoxycarbonylpentyl)-1,1,1-trifluoro-2-butanone to give the title material (250 mg, 25%) as a pale yellow oil.

$^1$H NMR (C$_6$D$_6$, δ, ppm): 1.65–1.26, 1.28–1.32, 1.38–1.43 and 1.57–1.59 (2H, 1H, 2H, 1H, 4 m, —(CH$_2$)$_3$—), 1.45 (9H, s, —tBu), 2.03 (2H, t, J=7.3 Hz, —CH$_2$CO$_2$tBu), 2.10 (3H, s, —NMe), 2.49 (1H, dd, J=13.8 and 6.5 Hz, —CH$_2$CHCO—), 2.61 (2H, t, J=5.9 Hz, —NCH$_2$—CH$_2$—), 2.73 (2H, d, J=7.9 Hz, —NCH$_2$CH—), 2.83 (1H, dd, J=13.8 and 7.8 Hz, —CH$_2$CHCO—), 3.08 (1H, m, —CHCO—), 3.65 (2H, t, J=7.9 Hz, —OCH$_2$—), 3.86 (1H, t, J=7.9 Hz, —CH(Ar)$_2$), 6.77 and 6.92 (2×2H, 2 d, J=8.6 Hz, aromatic H), 6.85 and 7.18 (2×4H, 2 d, J=8.4 Hz, aromatic H(benzhydryl)).

4-[4-[2-[N-[2-Bis-(4-chlorophenyl)ethyl]-N-methylamino]ethoxy]phenyl]-3-(4-carboxybutyl)-1,1,1-trifluoro-2-butanone, trifluoroacetic acid salt

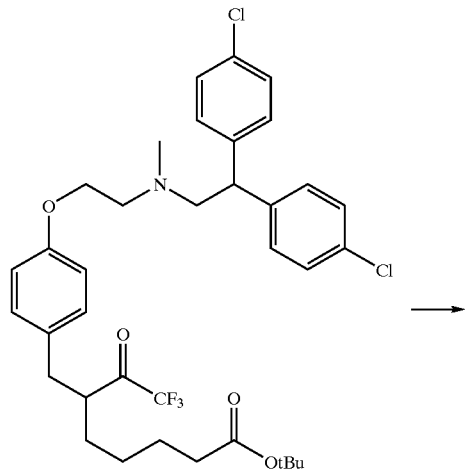

4-[4-[2-[N-[2-Bis-(4-chlorophenyl)ethyl]-N-methylamino]ethoxy]phenyl]-3-(4-t-butoxycarbonylbutyl)-1,1,1-trifluoro-2-butanone (100 mg, 0.15 mmol) was treated with a solution of trifluoroacetic acid (10%) in dichloromethane (5 ml). The mixture was stirred at room temperature for 3 hours and concentrated in vacuo to give the title compound (115 mg, 100%) as a pale yellow syrup.

Anal. Calcd. for C$_{32}$H$_{34}$NCl$_2$F$_3$O$_4$·CF$_3$COOH·2.0 H$_2$O·0.3 CHCl$_3$: C, 50.83%; H, 4.89%; N, 1.73%; Found: C, 50.92%; H, 4.50%; N 1.50%.

MS (ESI): 622.12 (M–H)$^-$.

Example 5

4-[4-[2-[N-[2-Bis-(4-chlorophenyl)ethyl]-N-methylamino]ethoxy]phenyl]-3-(4-carboxyphenylmethyl)-1,1,1-trifluoro-2-butanone, trifluoacetic acid salt

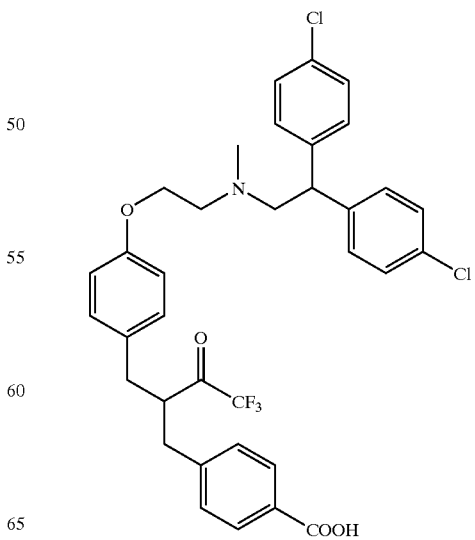

4-[4-[2-[N-[2-Bis-(4-chlorophenyl)ethyl]-N-methylamino]ethoxy]phenyl]-3-(4-tert-butoxycarbonylphenylmethyl)-1,1,1-trifluoro-2-butanone

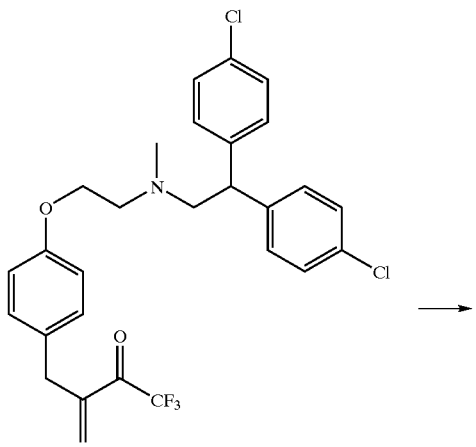

To a stirred solution of tert-butyl 4-iodobenzoate (0.5 g, 1.64 mmol) in 5 ml of THF-pentane-diethyl ether (4:1:1) at −100° C. was added butyllithium (1.6 M in hexane, 1.1 ml, 1.72 mmol). After 3 minutes at this temperature, CuCN.2LiCl (1M in THF, 1.8 ml, 1.8 mmol) was added. After another 10 minutes at this temperature, a solution of trimethylsilyl chloride (0.25 ml, 2 mmol) and 3-[4-[2-[N-[2-bis-(4-chlorophenyl)ethyl]-N-methylamino]ethoxy]phenylmethyl]-1,1,1-trifluoro-3-buten-2-one (0.5 g, 1.64 mmol) in THF (2 ml) was added. The resulting mixture was stirred at −78° C. for 2 hours, quenched with aqueous ammonium chloride. After 15 minutes at room temperature, the mixture was diluted with ethyl acetate, washed with aqueous ammonium chloride, brine, dried over magnesium sulfate and concentrated in vacuo. Chromatography of the residue on silica gel (dichloromethane:ethyl acetate= 100:0–97:3) gave the title material (200 mg, 38%) as a pale yellow oil.

$^1$H NMR (C$_6$D$_6$, δ, ppm): 1.45 (9H, s, —tBu), 2.05 (3H, s, —NMe), 2.44 (2H, br dd, 2×—CH$_2$CHCO—), 2.55 (2H, t, J=5.9 Hz, —NCH$_2$CH$_2$—), 2.67 (2H, d, J=7.9 Hz, —NCH$_2$CH—), 2.77 (2H, m, 2×—CH$_2$CHCO—), 3.37 (1H, m, —CHCO—), 3.59 (2H, t, -J=5.9 Hz, —OCH$_2$—), 3.80 (1H, t, J=7.9 Hz, —CH(Ar)$_2$), 6.70 (2H, d, J=8.6 Hz, aromatic H), 6.78–6.86 (8H, m, aromatic H), 7.11 (4H, d, J=8.4 Hz, aromatic H), 8.08 (2H, d, J=8.1 Hz, aromatic H).

4-[4-[2-[N-[2-Bis-(4-chlorophenyl)ethyl]-N-methylamino]ethoxy]phenyl]-3-(4-carboxyphenylmethyl)-1,1,1-trifluoro-2-butanone, trifluoacetic acid salt

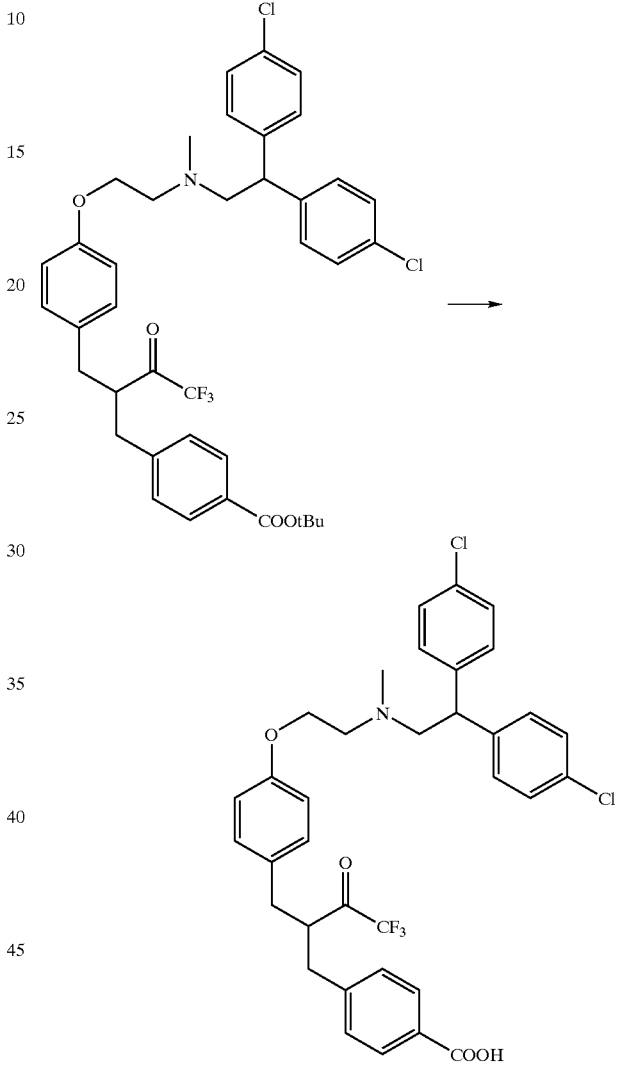

A solution of 4-[4-[2-[N-[2-bis-(4-chlorophenyl)ethyl]-N-methylamino]ethoxy]phenyl]-3-(4-tert-butoxycarbonylphenylmethyl)-1,1,1-trifluoro-2-butanone (114 mg, 0.16 mmol) in 5 ml of trifluoroacetic acid-dichloromethane (1:9) was stirred at room temperature for 1.5 hours and concentrated in vacuo. The residue was dissolved in 10 ml of trifluoroacetic acid-dichloromethane (1:9) and stirred for another 1.5 hours, then concentrated in vacuo to give the trifluoroacetic acid salt of the title material (122 g, 91%) as a white foam.

Anal. Calcd. for C$_{35}$H$_{32}$NCl$_2$F$_3$O$_4$·CF$_3$COOH·1.5H$_2$O·0.3CHCl$_3$: C, 53.63%; H, 4.38%; N, 1.68%; Found: C, 53.63%; H, 4.26%; N, 1.99%.

Example 6

4-[4-[2-[N-[2-Bis-(4-chlorophenyl)ethyl]-N-methylamino]ethoxy]phenyl]-3-(4-carboxyphenylethyl)-1,1,1-trifluoro-2-butanone, trifluoacetic acid salt

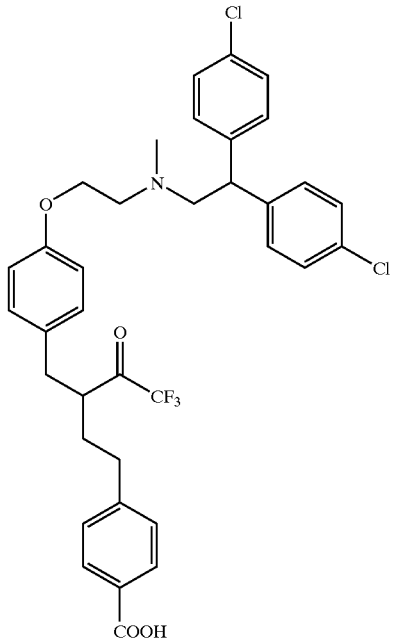

tert-Butyl 4-(bromomethyl)benzoate 4-(Bromomethyl)benzoic acid (6 g, 26 mmol) and isobutene (30 ml) were reacted by the same procedure as described in Example 3 for the preparation of tert-butyl 4-iodobutanoate and afforded the title material (2.4 g) as a pale yellow oil.

$^1$H NMR (CDCl$_3$, δ, ppm): 1.60 (9H, s, —tBu), 4.51 (2H, s, —CH$_2$Br), 7.44 and 7.97 (2×2H, d, J=8.2 Hz, aromatic H).

4-[4-[2-[N-[2-Bis-(4-chlorophenyl)ethyl]-N-methylamino]ethoxy]phenyl]-3-(4-tert-butoxycarbonylphenylethyl)-1,1,1-trifluoro-2-butanone

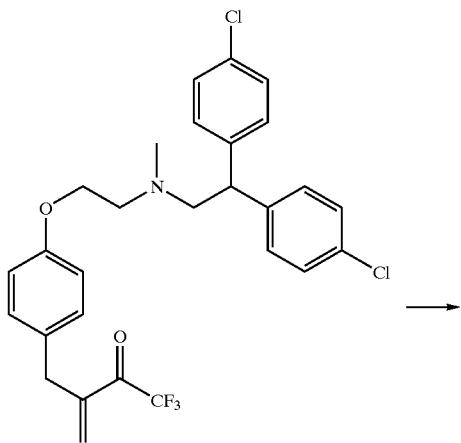

→

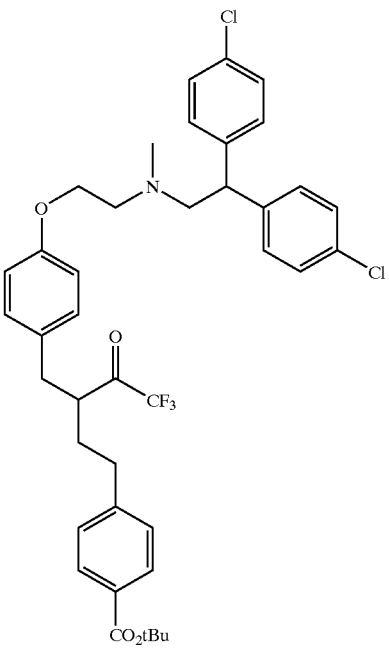

3-[4-[2-[N-[2-Bis-(4-chlorophenyl)ethyl]-N-methylamino]ethoxy]phenylmethyl]-1,1,1-trifluoro-3-buten-2-one (250 mg, 0.45 mmol) and 4-tert-butoxycarbonylphenylmethylzinc bromide (prepared in situ from tert-butyl 4-bromomethylbenzoate) were reacted by the general procedure as described in Example 5 for the preparation of 4-[4-[2-[N-[2-bis-(4-chlorophenyl)ethyl]-N-methylamino]ethoxy]phenyl]-3-(4-tert-butoxycarbonylphenylmethyl)-1,1,1-trifluoro-2-butanone and afforded the title material (30 mg) as a colorless oil.

$^1$H NMR (C$_6$D$_6$, δ, ppm): 1.48 (9H, —tBu), 1.52 and 1.85 (2×1H, 2 m, —CH$_2$—CH$_2$—C$_6$H$_4$—), 2.05 (3H, s, —NMe), 2.16–2.21 and 2.26–2.30 (2×1H, 2 m, —CH$_2$—C$_6$H$_4$—), 2.41 (1H, dd, J=13.8 and 6.8 Hz, —CH$_2$—CHCO—), 2.55 (2H, t, J=5.9 Hz, —NCH$_2$CH$_2$—), 2.68 (2H, d, J=7.7 Hz, —NCH$_2$CH—), 2.77 (1H, dd, J=13.8 and 7.0 Hz, —CH$_2$CHCO—), 3.03 (1H, m, —CHCO—), 3.59 (2H, t, J=5.9 Hz, —OCH$_2$—), 3.80 (1H, t, J=7.7 Hz, —CH(Ar)$_2$), 6.69 (2H, d, J=8.6 Hz, aromatic H), 6.79–6.97 (8H, m, aromatic H), 7.12 (4H, d, J=8.0 Hz, aromatic H), 8.11 (2H, m, aromatic H).

4-[4-[2-[N-[2-Bis-(4-chlorophenyl)ethyl]-N-methylamino]ethoxy]phenyl]-3-(4-carboxyphenylethyl)-1,1,1-trifluoro-2-butanone, trifluoacetic acid salt

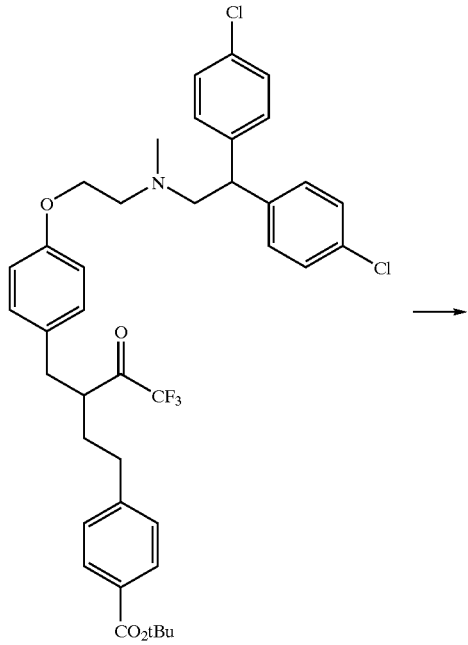

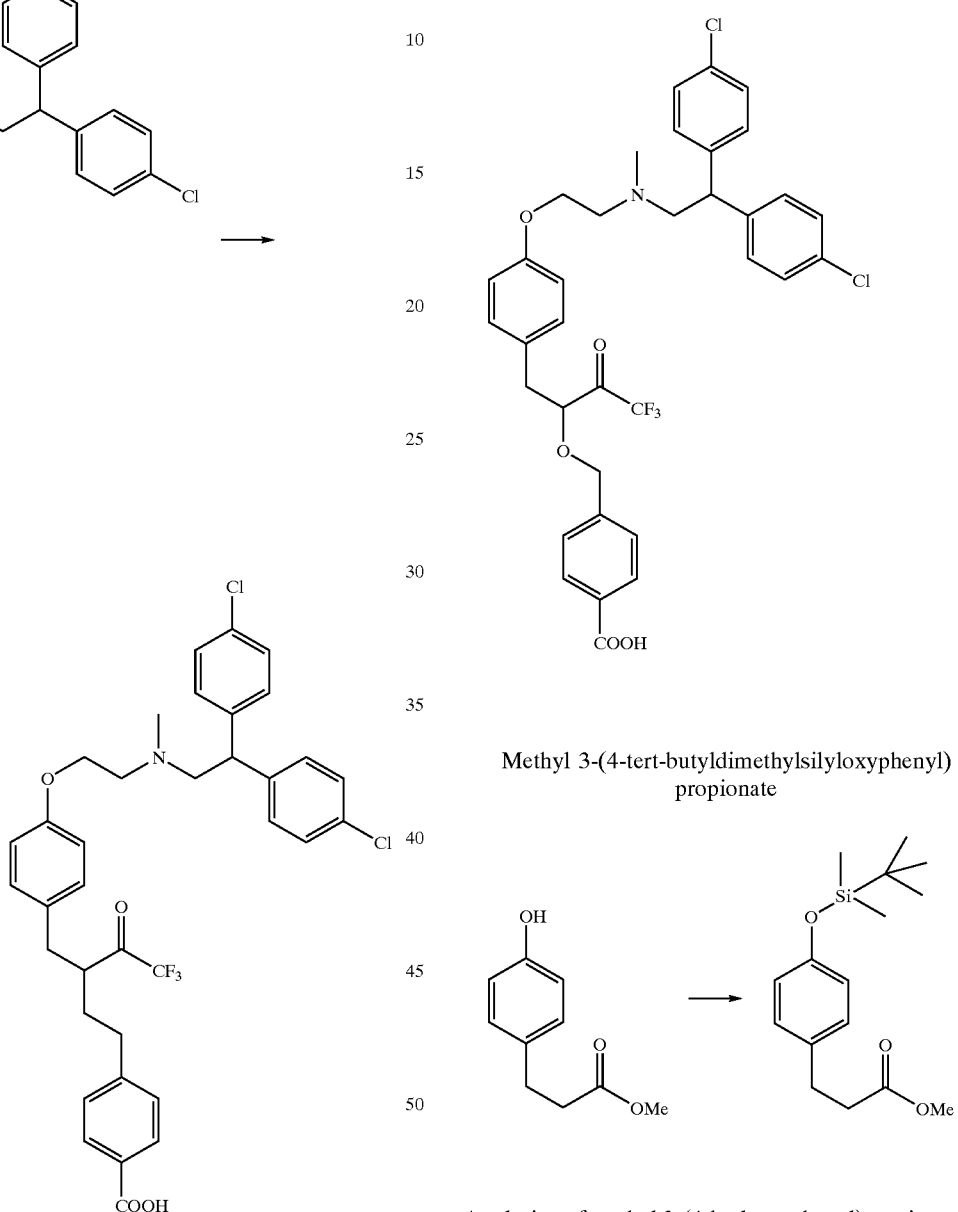

4-[4-[2-[N-[2-Bis-(4-chlorophenyl)ethyl]-N-methylamino]ethoxy]phenyl]-3-(4-tert-butoxycarbonylphenylethyl)-1,1,1-trifluoro-2-butanone (30 mg) was treated with a solution of trifluoroacetic acid (10%) in dichloromethane (5 ml). The mixture was stirred at room temperature for 3 hours and concentrated in vacuo to give the title compound as an off-white foam.

MS(ESI): 670.21 (M−H)⁻.

Example 7

4-[4-[2-[N-[2-Bis-(4-chlorophenyl)ethyl]-N-methylamino]ethoxy]phenyl]-3-[(4-cCarboxyphenyl)methoxy]-1,1,1-trifluoro-2-butanone, trifluoroacetic acid salt

Methyl 3-(4-tert-butyldimethylsilyloxyphenyl) propionate

A solution of methyl 3-(4-hydroxyphenyl)propionate (5 g, 27.7 mmol) and chlorotert-butyldimethylsilane (5 g, 33.3 mmol) in DMF was treated with triethylamine (4.6 ml). The mixture was stirred at room temperature for 20 hours. More chlorotert-butyldimethylsilane (0.8 g) and triethylamine (0.8 ml) were added, the resulting mixture was stirred at room temperature for another 2 hours, poured into saturated aqueous sodium bicarbonate (500 ml). The mixture was stirred at room temperature for 5 minutes and extracted with ether. The organic phase was washed with brine, dried over sodiun sulfate and concentrated in vacuo. Bulb-to-bulb distillation gave the title material (7.39 g, 91%) as a colorless oil (b.p. 104–105° C./0.025 mm Hg).

Methyl 3-(4-tert-butyldimethylsilyloxyphenyl)-2-hydroxypropionate

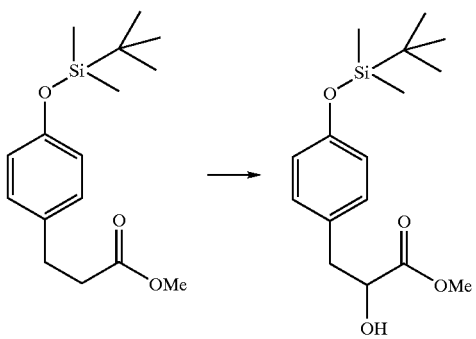

To a solution of methyl 3-(4-tert-butyldimethylsilyloxyphenyl)propionate (5 g, 16.98 mmol) in THF (50 ml) at −78° C. was added dropwise potassium bis(trimethylsilyl)amide (0.5M in toluene, 34 ml, 17 mmol). The mixture was stirred at this temperature for 0.5 hours and treated with dropwise addition of a solution of trans-2-phenylsulfonyl-3-phenyloxaziridine (5.3 g, 20.38 mmol) in THF (30 ml). The mixture was stirred at −78° C. for 1 hour, quenched with aqueous ammonium chloride, warmed to room temperature and diluted with ethyl acetate. The organic phase was washed with aqueous ammonium chloride, brine, dried over sodium sulfate and concentrated in vacuo. Bulb-to-bulb distillation gave the title material (2 g, 38%) as a colorless oil (b.p. 115° C./0.025 mm Hg) which solidified upon standing.

Anal. Calcd. for $C_{16}H_{27}O_4Si$: C, 61.90%; H, 8.44%; Found: C, 61.95%; H, 8.42%.

Methyl 3-(4-tert-butyldimethylsilyloxyphenyl)-2-[(4-tert-butoxycarbonylphenyl)methoxy]propionate

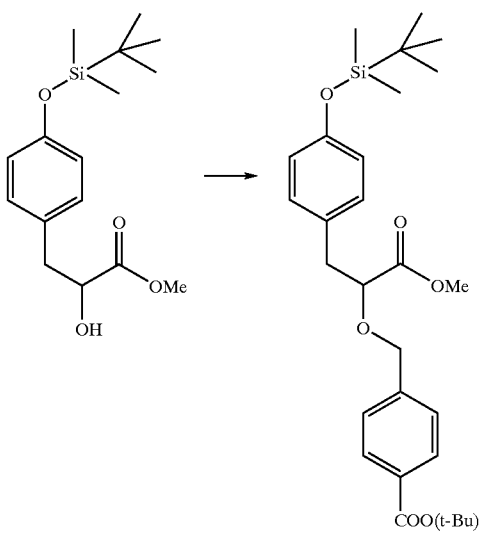

A solution of methyl 3-(4-tert-butyldimethylsilyloxyphenyl)-2-hydroxypropionate (300 mg, 0.97 mmol) in THF (2 ml) at −78° C. was treated with a suspension of sodium hydride (60%, 40 mg, 1 mmol) in THF (1 ml). The mixture was stirred at −40° C. for 15 minutes, then tetrabutyl ammonium iodide (20 mg) and tert-butyl 4-bromomethylbenzoate (270 mg, 0.97mmol) dissolved in THF (1 ml) were added. After the cooling bath was removed, the mixture was stirred for 16 hours, quenched with saturated aqueous ammonium chloride and diluted with ethyl acetate. The organic phase was washed with brine, dried over sodium sulfate and concentrated in vacuo. The residue was chromatographed on silica gel (hexane:ethyl acetate=85:15) to give the title material (200 mg, 41%) as a colorless oil.

Methyl 2-[(4-tert-butoxycarbonylphenyl)methoxy]-3-(4-hydroxyphenyl)propionate

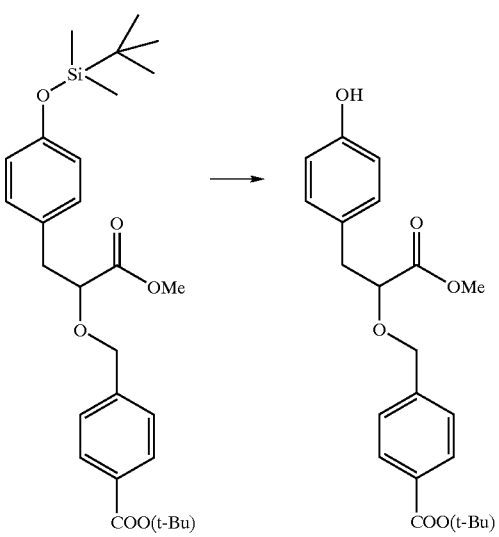

A solution of methyl 3-(4-tert-butyldimethylsilyloxyphenyl)-2-[(4-tert-butoxycarbonylphenyl)methoxy]propionate (310 mg, 0.61 mmol) in THF (5 ml) at −20° C. was treated with tetrabutylammonium fluoride-acetic acid (1.0M in THF, 0.76 ml, 0.76 mmol). The mixture was stirred at this temperature for 15 minutes, quenched with saturated aqueous sodium bicarbonate and extracted with diethyl ether. The organic phase was washed with brine, dried over sodium sulfate and concentrated in vacuo to give the title material (256 mg, 100%) as a pale yellow oil.

59
Methyl 3-[4-[2-[N-[2-bis-(4-chlorophenyl)ethyl]-N-methylamino]ethoxy]phenyl]-2-[(4-tert-butoxycarbonylphenyl)methoxy]propionate

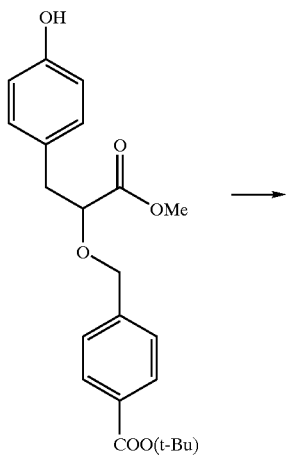

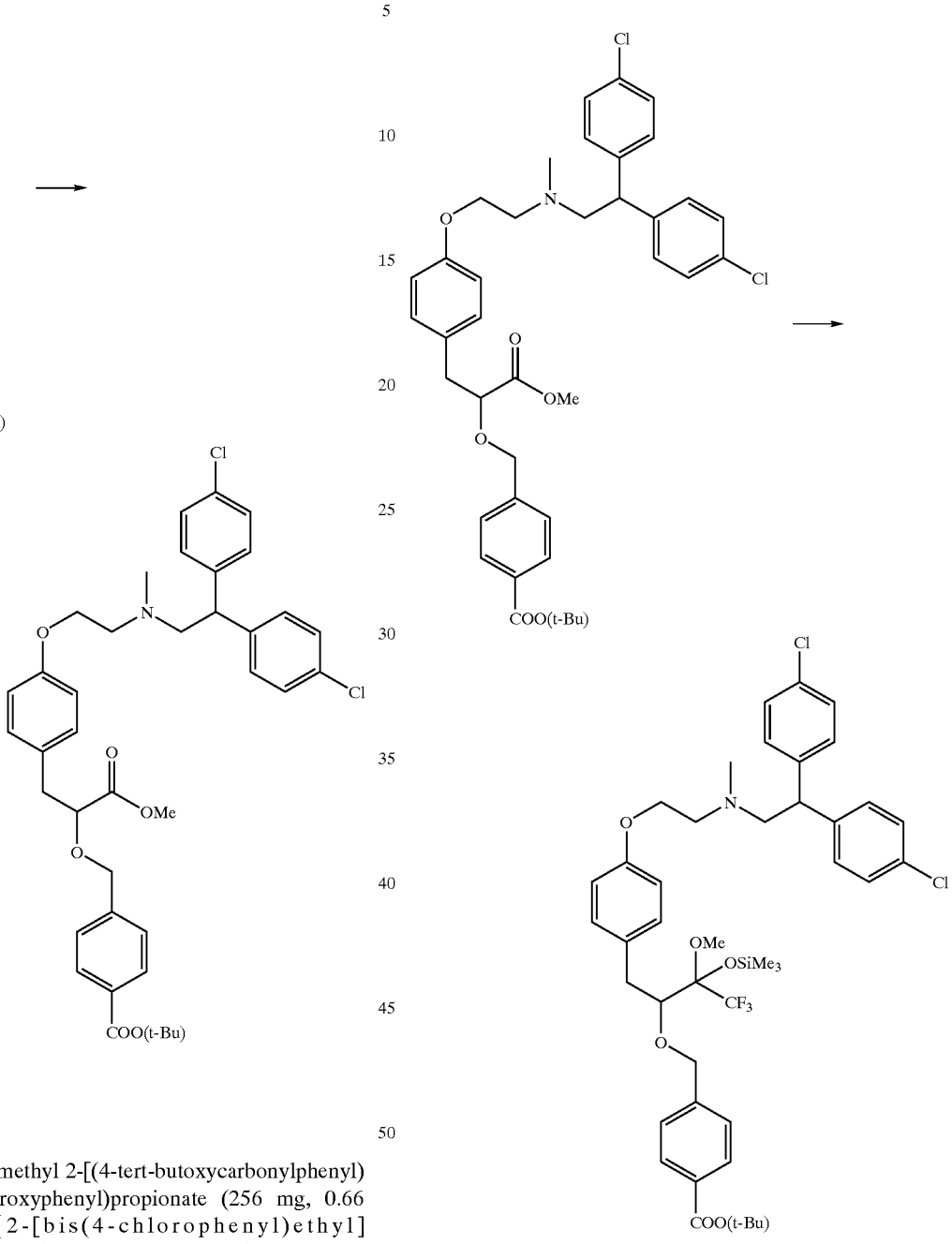

To a solution of methyl 2-[(4-tert-butoxycarbonylphenyl)methoxy]-3-(4-hydroxyphenyl)propionate (256 mg, 0.66 mmol), 2-{2-[bis(4-chlorophenyl)ethyl]methylamino}ethanol (430 mg, 1.32 mmol) and triphenylphosphine (190 mg, 0.73 mmol) in THF (5 ml) was added dropwise diisopropyl azodicarboxylate (0.170 ml, 0.73 mmol). The mixture was stirred at room temperature for 16 hours. More triphenylphosphine (3×50 mg) and diisopropyl azodicarboxylate (3×0.025 ml) were added. The mixture was stirred at room temperature for another 3×2 hours and concentrated in vacuo. The residue was triturated with hexane, filtered and washed with hexane. The filtrate was concentrated in vacuo and the residue was chromatographed on silica gel hexane-ethyl acetate) to give the title compound (250 mg, 55%) as a colorless oil.

60
4-[4-[2-[N-[2-Bis-(4-chlorophenyl)ethyl]-N-methylamino]ethoxy]phenyl]-3-[(4-tert-butoxycarbonylphenyl)methoxy]-1,1,1-trifluoro-2-butanone, methyl trimethylsilyl ketal A solution of methyl 3-[4-[2-[N-[2-bis-(4-chlorophenyl)ethyl]-N-methylamino]ethoxy]phenyl]-2-[(4-tert-butoxycarbonylphenyl)methoxy]propionate (26 mg, 0.037 mmol) and trifluoromethyl trimethylsilane (42 µl, 0.37 mmol) in toluene (1 ml) at −78° C. was treated with tetrabutylammonium fluoride (1.0M in THF, 5 µl, 0.005 mmol). The cooling bath was removed, and the reaction mixture was stirred at room temperature for 15 minutes and concentrated in vacuo. The residue was chromatographed on silica gel (hexane:ethyl acetate 1:0 to 4:1) to give the title compound (30 mg, 96%) as a pale yellow oil.

61

4-[4-[2-[N-[2-Bis-(4-chlorophenyl)ethyl]-N-methylamino]ethoxy]phenyl]-3-[(4-tert-butoxycarbonylpheny)lmethoxy]-1,1,1-trifluoro-2-butanone

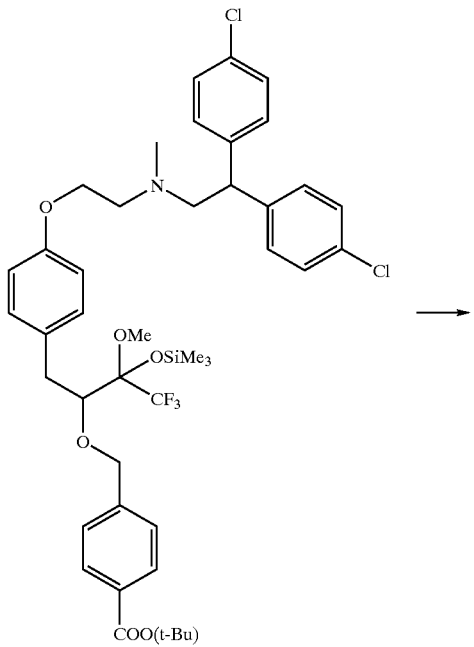

A solution of 4-[4-[2-[N-[2-bis-(4-chlorophenyl)ethyl]-N-methylamino]ethoxy]phenyl]-3-[(4-tert-butoxycarbonylphenyl)methoxy]-1,1,1-trifluoro-2-butanone, methyl trimethylsilyl ketal (30 mg, 0.036 mmoL) in THF (0.5 ml) at 0° C. was treated with a mixture of tetrabutylammonium fluoride and acetic acid (1.0M in THF, 47 μl, 0.047 mmol). The mixture was stirred at room temperature for 0.5 hours, diluted with ethyl acetate, washed with saturated aqueous sodium bicarbonate, brine, dried over sodium sulfate and concentrated in vacuo. The residue was chromatographed on silica gel (hexane:ethyl acetate= 1:1) to give the title compound (14 mg, 53%) as a colorless oil.

62

4-[4-[2-[N-[2-Bis-(4-chlorophenyl)ethyl]-N-methylamino]ethoxy]phenyl]-3-[(4-carboxyphenyl)methoxy]-1,1,1-trifluoro-2-butanone, trifluoroacetic acid

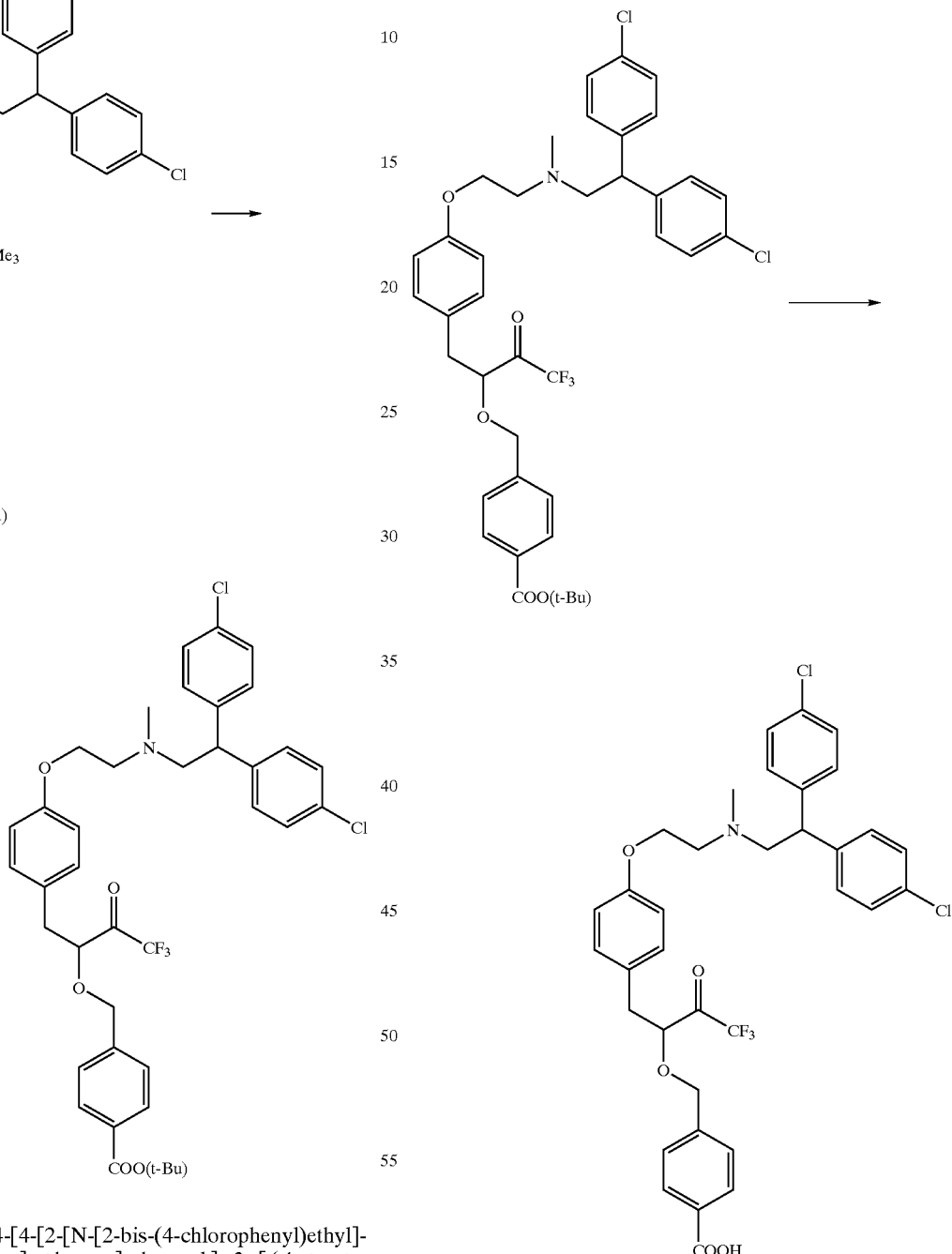

4-[4-[2-[N-[2-Bis-(4-chlorophenyl)ethyl]-N-methylamino]ethoxy]phenyl]-3-[(4-tert-butoxycarbonylpheny)lmethoxy]-1,1,1-trifluoro-2-butanone (14 mg, 0.019 mmol) was treated with a solution of trifluoroacetic acid (10%) in dichlroromethane (3 ml). The mixture was stirred at room temperature for 3 hours and concentrated in vacuo to give the title compound as a yellow sticky solid.

Example 8

4-[4-[2-[N-[2-Bis-(4-chlorophenyl)ethyl]-N-methylamino]ethoxy]phenyl]-3-methoxy-1,1,1-trifluoro-2-butanone

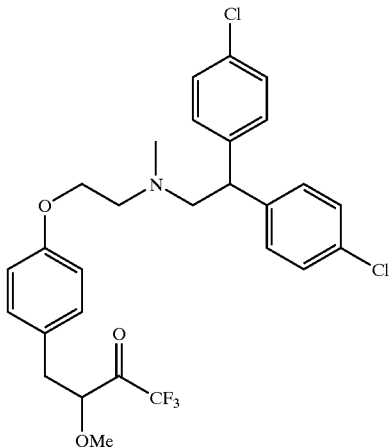

Methyl 3-(4-benzyloxyphenyl)propanoate

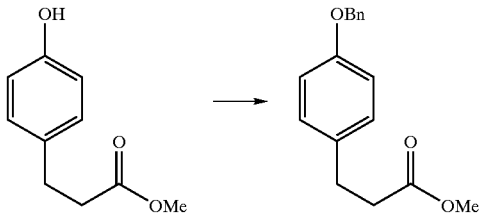

To a suspension of sodium hydride in DMF (50 ml) at 0° C. was added dropwise a solution of methyl 3-(4-hydroxyphenyl)propionate (10.0 g, 55.5 mmol) and benzyl bromide (7.93 ml, 66.7 mmol) dissolved in DMF (100 ml). The mixture was stirred at room temperature for 16 hours, cooled to 0° C., quenched with aqueous ammonium chloride (50 ml) and extracted with ethyl acetate (2×150 ml). The combined organic layers were washed with aqueous ammonium chloride (50 ml), brine (3×60 ml), dried over sodium sulfate and concentrated in vacuo. The residue was crystallized from hexane-ethyl acetate to give the title compound (13.7 g, 91%) as a white solid.

Anal. Calcd. for $C_{17}H_{18}O_3$: C, 75.53%; H, 6.71%; Found: C, 75.48%; H, 6.68%.

3-(4-Benzyloxyphenyl)propanoic acid

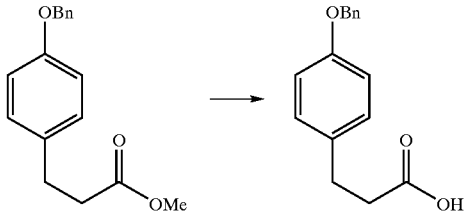

A suspension of methyl 3-(4-benzyloxyphenyl) propanoate in ethanol (200 ml) and THF (100 ml) was treated with an aqueous solution of potassium hydroxide (6.7 g, 1.5 N, 101.2 mmol). The mixture was stirred at 60° C. for 1.5 hours, cooled to room temperature, adjusted to pH 3–4 with 1N HCl. The solvent was removed in vacuo to give the title material (12.8 g, 98%) as a white solid.

Anal. Calcd. for $C_{16}H_{16}O_3 \cdot 0.2H_2O$: C, 73.94%; H, 6.36%; Found: C, 74.02%; H, 6.18%.

4-(4-Benzyloxyphenyl)-1,1,1-trifluoro-2-butanone

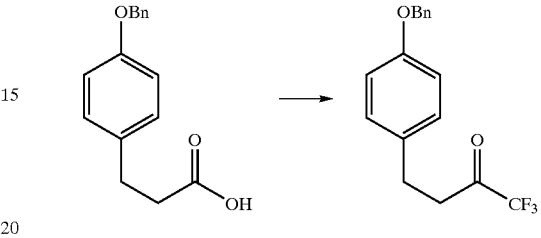

To a solution of 3-(4-benzyloxyphenyl)propanoic acid (12.8 g, 50 mmol) in dichloromethane (100 ml) were added slowly oxalyl chloride (10 ml, 115 mmol) and two small drops of DMF. The mixture was stirred at room temperature for 4 hours and the excess reagent and solvent was removed in vacuo. The residue was dissolved in dry dichloromethane (100 ml), cooled to 0° C. and trifloroacetic anhydride (21 ml, 150 mmol) was added. To this mixture at 0° C. was added dropwise pyridine (8.1 ml, 100 mmol) over 0.5 hours. The resulting mixture was stirred at room temperature for 3 hours, cooled again to 0° C. and quenched with water (25 ml). After stirring at room temperature for 0.5 hours, the mixture was adjusted to pH 7–8 with solid sodium bicarbonate and diluted with ethyl acetate (300 ml). The organic phase was washed with water, aqueous sodium bicarbonate, brine, dried over sodium sulfate and concentrated in vacuo. The residue was chromatographed on silica gel (hexane:ethyl acetate=5:1 to 4:1) to afford the title material (10.6 g, 68.8%) as a pale yellow solid.

4-(4-Benzyloxyphenyl)-1,1,1-trifluoro-2-trimethylsilyloxy-2-butene

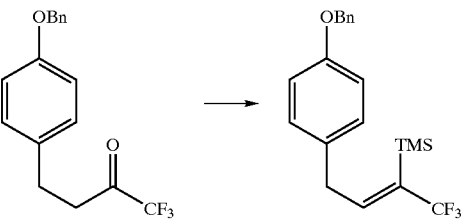

To a solution of 4-(4-benzyloxyphenyl)-1,1,1-trifluoro-2-butanone (2.25 g, 7.26 mmol) and trimethylsilyl chloride (1.84 ml, 14.5 mmol) in THF (20 ml) at 0° C. was added dropwise triethylamine (3.1 ml, 21.8 mmol). The mixture was stirred at room temperature for 1 hour, diluted with hexane (200 ml), filtered and washed with hexane. The filtrate was washed with brine (2×50 ml), dried over sodium sulfate for 2 minutes and concentrated in vacuo to give the title material (2.58 g, 93%) as a yellow solid.

4-(4-Benzyloxyphenyl)-3-bromo-1,1,1-trifluoro-2-butanone and

4-(4-Hydroxyphenyl)-3-bromo-1,1,1-trifluoro-2-butanone

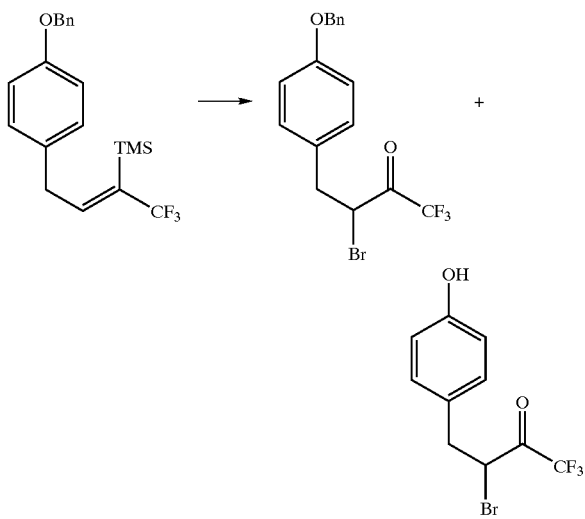

To a solution of 4-(4-benzyloxyphenyl)-1,1,1-trifluoro-2-trimethylsilyloxy-2-butene (2.58 g, 6.79 mmol) in dichloromethane (40 ml) at room temperature was added dropwise a solution of bromine (1.14 g, 7.13 mmol) in dichoromethane (5 ml). The mixture was stirred at room temperature for 2 hours, diluted with diethyl ether (200 ml), washed with brine (2×50 ml), dried over sodium sulfate and concentrated in vacuo. The residue was chromatographed on silica gel (hexane:ethyl acetate=4:1 to 2:1) to afford 4-(4-benzyloxyphenyl)-2-bromo-1,1,1-trifluoro-2-butanone (1.96 g, 75%) as a pale yellow liquid and 4-(4-hydroxyphenyl)-2-bromo-1,1,1-trifluoro-2-butanone (0.22 g, 11%) as a pale yellow liquid.

(2S*, 3R*)-4-(4-Benzyloxyphenyl)-2-methoxy-1,1,1-trifluoro-2,3-epoxy-butane and

(2R*, 3R*)-4-(4-Benzyloxyphenyl)-2-methoxy-1,1,1-trifluoro-2,3-epoxy-butane

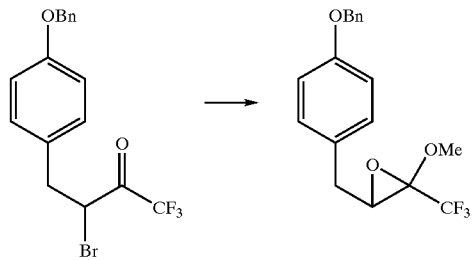

A solution of 4-(4-benzyloxyphenyl)-3-bromo-1,1,1-trifluoro-2-butanone (1.956 g, 5.05 mmol) in methanol (40 ml) was treated with sodium methoxide (1.3M in methanol, 4.1 ml, 5.3 mmol). The mixture was stirred at room temperature for 1 hour, diluted with diethyl ether, washed with water, brine, dried over sodium sulfate and concentrated in vacuo. The residue was chromatographed on silica gel (hexane:ethyl acetate=30:1 to 9:1) to give (2S*, 3R*)-4-(4-benzyloxyphenyl)-2-methoxy-1,1,1-trifluoro-2,3-epoxy-butane (957 mg, 56%) as a white waxy solid and (2R*, 3R*)-4-(4-benzyloxyphenyl)-2-methoxy-1,1,1-trifluoro-2,3-epoxy-butane (382 mg, 22%) as a pale yellow oil.

Anal. Calcd. for $C_{18}H_{17}F_3O_3$ (2S*, 3R* isomer): C, 63.90%; H, 5.06%; Found: C, 63.82%; H, 5.00%.

(2S*, 3R*)-4-(4-Hydroxyphenyl)-2-methoxy-1,1,1-trifluoro-2,3-epoxy-butane

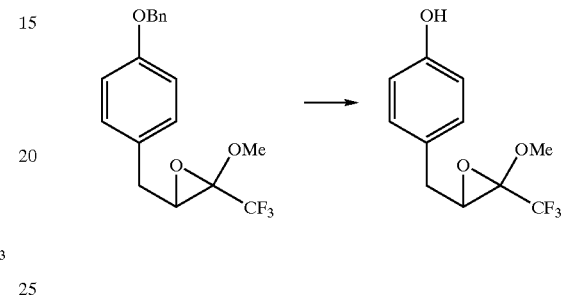

A solution of (2S*, 3R*)-4-(4-benzyloxyphenyl)-2-methoxy-1,1,1-trifluoro-2,3-epoxy-butane (957 mg, 2.8 mmol) in ethyl acetate (30 ml) was hydrogenated at atmospheric pressure over palladium hydroxide/carbon (20%, 290 mg) for 1 hour. The mixture was filtered through celite and washed with ethyl acetate. The filtrate was concentrated in vacuo and chromatographed on silica gel (hexane:ethyl acetate=7:1–5:1) to give the title compound (691 mg, 97%) as a colorless oil.

Anal. Calcd. for $C_{11}H_{11}F_3O_3 \cdot 0.4H_2O$: C, 51.73%; H, 4.66%; Found: C, 51.80%; H, 4.69%.

4-[4-[2-[N-[2-Bis-(4-chlorophenyl)ethyl-N-methylamino]ethoxy]phenyl]-2,3-epoxy-2-methoxy-1,1,1-trifluoro-2-butane

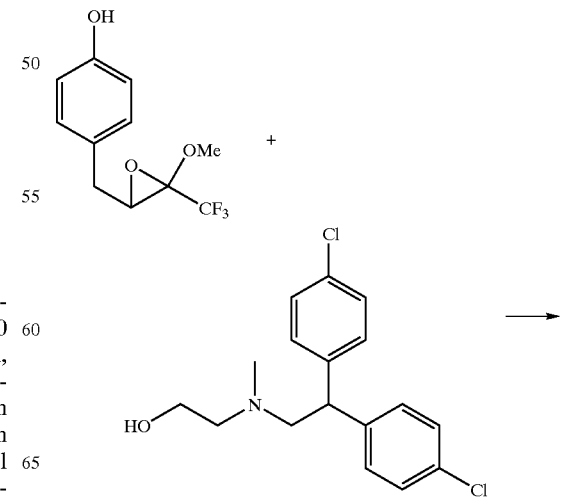

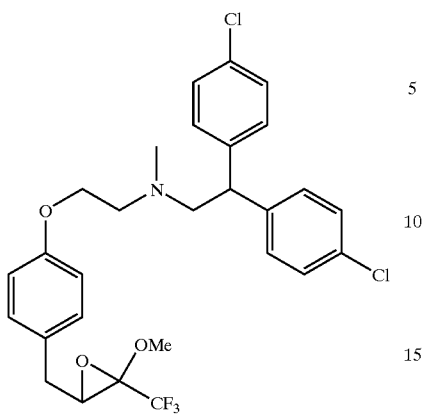

To a solution of (2S*, 3R*)-4-(4-hydroxyphenyl)-2-methoxy-1,1,1-trifluoro-2,3-epoxy-butane (691 mg, 2.78 mmol), 2-{2-[bis(4-chlorophenyl)ethyl]methylamino}ethanol (423 mg, 1.3 mmol) and triphenylphosphine (341 mg, 1.30 mmol) in benzene was added dropwise diethyl azodicarboxylate (0.205 ml, 1.30 mmol). The mixture was stirred at room temperature for 3 hours and concentrated in vacuo. The residue was triturated with hexane, filtered and washed with hexane. The filtrate was concentrated in vacuo and the residue was chromatographed twice on silica gel (dichoromethane:methanol=99:1 and hexane:ethyl acetate:triethylamine=7:1:0.4, respectively) to give the title compound (1.05 g, 68%) as a colorless oil.

4-[4-[2-[N-[2-Bis-(4-chlorophenyl)ethyl]-N-methylamino]ethoxy]phenyl]-3-methoxy-1,1,1-trifluoro-2-butanone

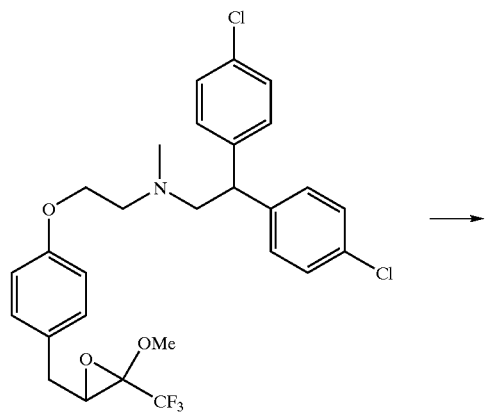

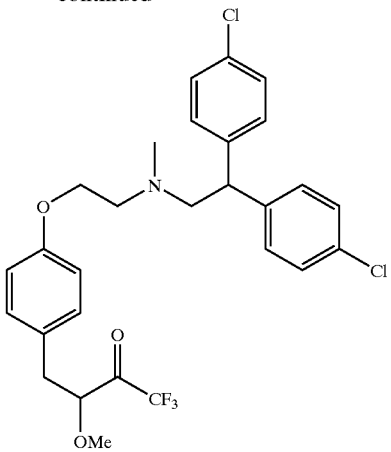

A solution of 4-[4-[2-[N-[2-bis-(4-chlorophenyl)ethyl-N-methylamino]ethoxy]phenyl]-2,3-epoxy-2-methoxy-1,1,1-trifluoro-2-butane (80 mg, 0.144 mmol) in methanol (5 ml) was heated under reflux for 18 hours and concentrated in vacuo. Chromatography of the residue on silica gel (hexane:ethyl acetate=2:1) gave the title compound (70 mg, 88%) as a colorless oil.

Treatment of the above free amine with anhydrous hydrogen chloride (1.0M in ether) gave the hydrochloride salt as a white foam.

Anal. Calcd. for $C_{28}H_{28}NCl_2F_3O_3 \cdot HCl \cdot 1.2H_2O$: C, 54.91%; H, 5.17%; N, 2.29%; Found: C, 54.88%; H, 5.15%; N, 2.25%.

Example 9

4-[4-[2-[N-[2-Bis-(4-chlorophenyl)ethyl]-N-methylamino]ethoxy]phenyl]-3-isopropxy-1,1,1-trifluoro-butanone

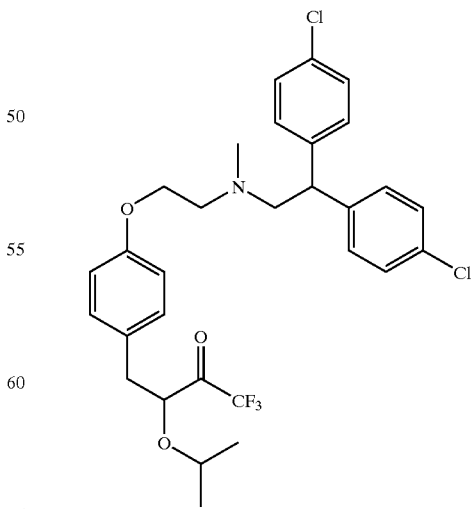

69

4-[4-[2-[N-[2-Bis-(4-chlorophenyl)ethyl]-N-methylamino]ethoxy]phenyl]-3-isopropxy-1,1,1-trifluoro-2-butanone

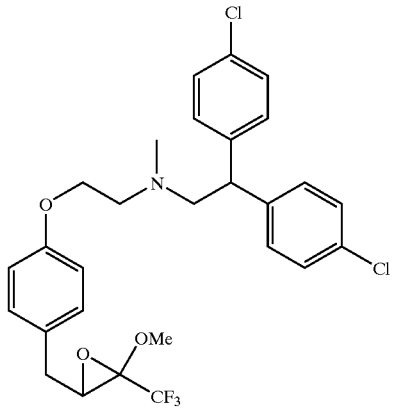

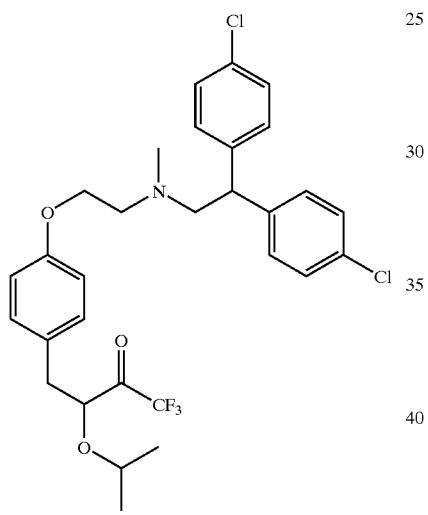

4-[4-[2-[N-[2-Bis-(4-chlorophenyl)ethyl-N-methylamino]ethoxy]phenyl]-2,3-epoxy-2-methoxy-1,1,1-trifluoro-2-butane (86 mg, 0.155 mmol) and isopropanol (4 ml) were reacted by the similar procedure as described in Example 8 for the preparation of 4-[4-[2-[N-[2-bis-(4-chlorophenyl)ethyl]-N-methylamino]ethoxy]phenyl]-3-methoxy-1,1,1-trifluoro-2-butanone and afforded the title material (44 mg, 49%) as a colorless oil.

HRMS for $C_{30}H_{33}Cl_2NF_3O_3$ (M+H)$^+$: Calcd: 582.17896; Found: 582.18100. Treatment of the above free amine with anhydrous hydrogen chloride (1.0M in ether) gave the hydrochloride salt as a white foam.

70

Example 10

4-[4-[2-[2-Bis-(4-chlorophenyl)butylsulfonyl]ethoxy]phenyl]-3-methoxy-1,1,1-trifluoro-2-butanone

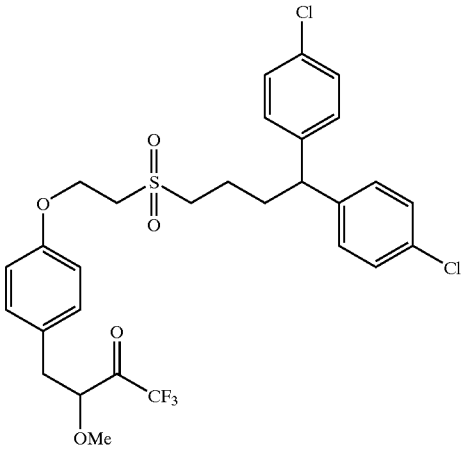

4-[4-[2-[2-Bis-(4-chlorophenyl)butylthio]ethoxy]phenyl]-1,1,1-trifluoro-2-tert-butyldimethylsilyloxy-2-butene

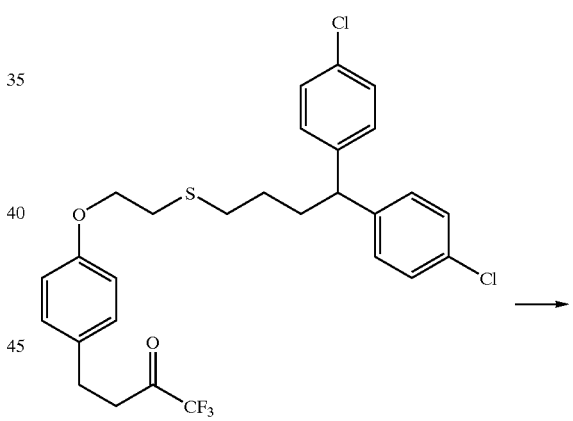

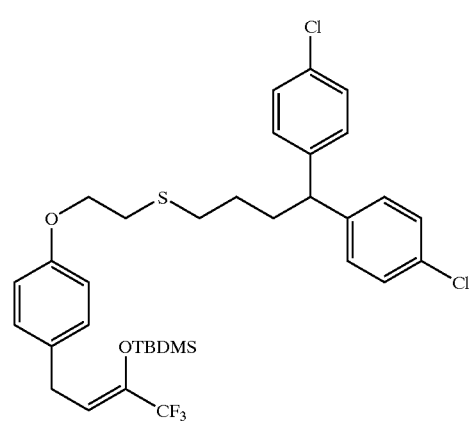

To a solution of 4-[4-[2-[2-bis-(4-chlorophenyl)butylthio]ethoxy]phenyl]-1,1,1-trifluoro-2-butanone [Patent Application WO 99/15129] (1 g, 1.8 mmol) and triethylamine (0.75 ml, 5.4 mmol) in dimethylformamide (15 ml) at 0° C. was added tert-butyl dimethylsilyl chloride (540 mg, 3.6 mmol). The mixture was stirred at room temperature for 1 hour, diluted with ethyl acetate, washed with water, brine, dried over sodium sulfate and concentrated in vacuo. Chromatography of the residue on silica gel (hexane:ethyl acetate= 20:1) gave the title compound (1.2 g, 99%) as a colorless oil.

4-[4-[2-[2-Bis-(4-chlorophenyl)butylsulfonyl]ethoxy]phenyl]-2,3-epoxy-2-tert-butyldimethylsilyloxy-1,1,1-trifluoro-2-butane

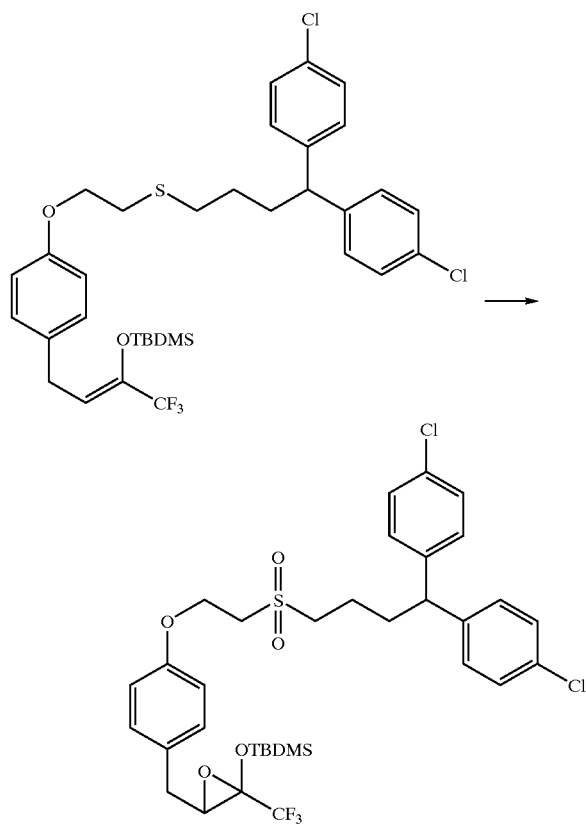

A solution of 4-[4-[2-[2-bis-(4-chlorophenyl)butylthio]ethoxy]phenyl]-1,1,1-trifluoro-2-tert-butyldimethylsilyloxy-2-butene (1.33 g, 1.99 mmol) in dichloromethane (50 ml) at 0° C. was treated with meta-chloroperbenzoic acid (80%, 2.58 g, 12 mmol). The mixture was stirred at room temperature for 70 hours, poured into an aqueous sodium bicarbonate-sodium thiosulfate and extracted with ethyl acetate. The organic layers were washed three times with aqueous sodium bicarbonate, brine, dried over sodium sulfate and concentrated in vacuo. The residue was chromatographed on silica gel (hexane:ethyl acetate= 2:1) to give the title material (1.326 g, 93%) as a colorless syrup.

4-[4-[2-[2-Bis-(4-chlorophenyl)butylsulfonyl]ethoxy]phenyl]-3-methoxy-1,1,1-trifluoro-2-butanone

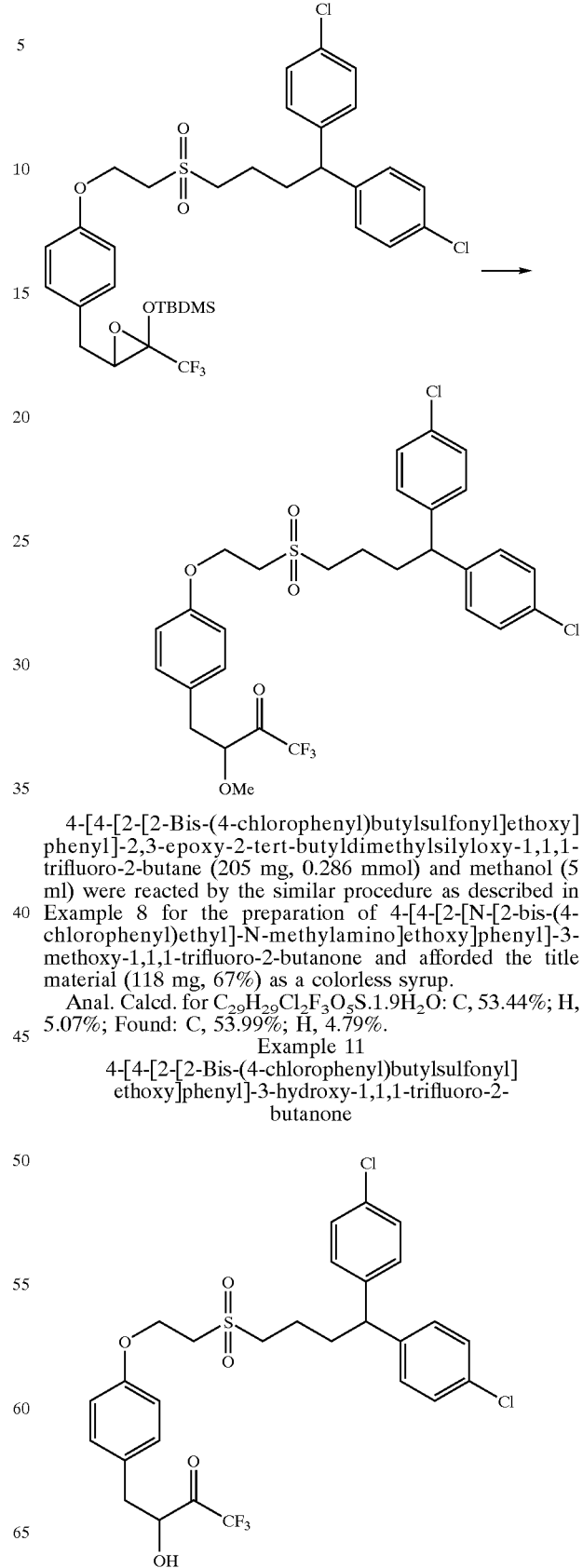

4-[4-[2-[2-Bis-(4-chlorophenyl)butylsulfonyl]ethoxy]phenyl]-2,3-epoxy-2-tert-butyldimethylsilyloxy-1,1,1-trifluoro-2-butane (205 mg, 0.286 mmol) and methanol (5 ml) were reacted by the similar procedure as described in Example 8 for the preparation of 4-[4-[2-[N-[2-bis-(4-chlorophenyl)ethyl]-N-methylamino]ethoxy]phenyl]-3-methoxy-1,1,1-trifluoro-2-butanone and afforded the title material (118 mg, 67%) as a colorless syrup.

Anal. Calcd. for $C_{29}H_{29}Cl_2F_3O_5S.1.9H_2O$: C, 53.44%; H, 5.07%; Found: C, 53.99%; H, 4.79%.

Example 11
4-[4-[2-[2-Bis-(4-chlorophenyl)butylsulfonyl]ethoxy]phenyl]-3-hydroxy-1,1,1-trifluoro-2-butanone

73

4-[4-[2-[2-Bis-(4-chlorophenyl)butylsulfonyl]
ethoxy]phenyl]-3-hydroxy-1,1,1-trifluoro-2-
butanone

74

Example 12

4-[4-[2-[N-[2-Bis-(4chlorophenyl)ethyl]-N-
methylamino]ethoxy]phenyl]-3-hydroxy-1,1,1-
trifluoro-2-butanone

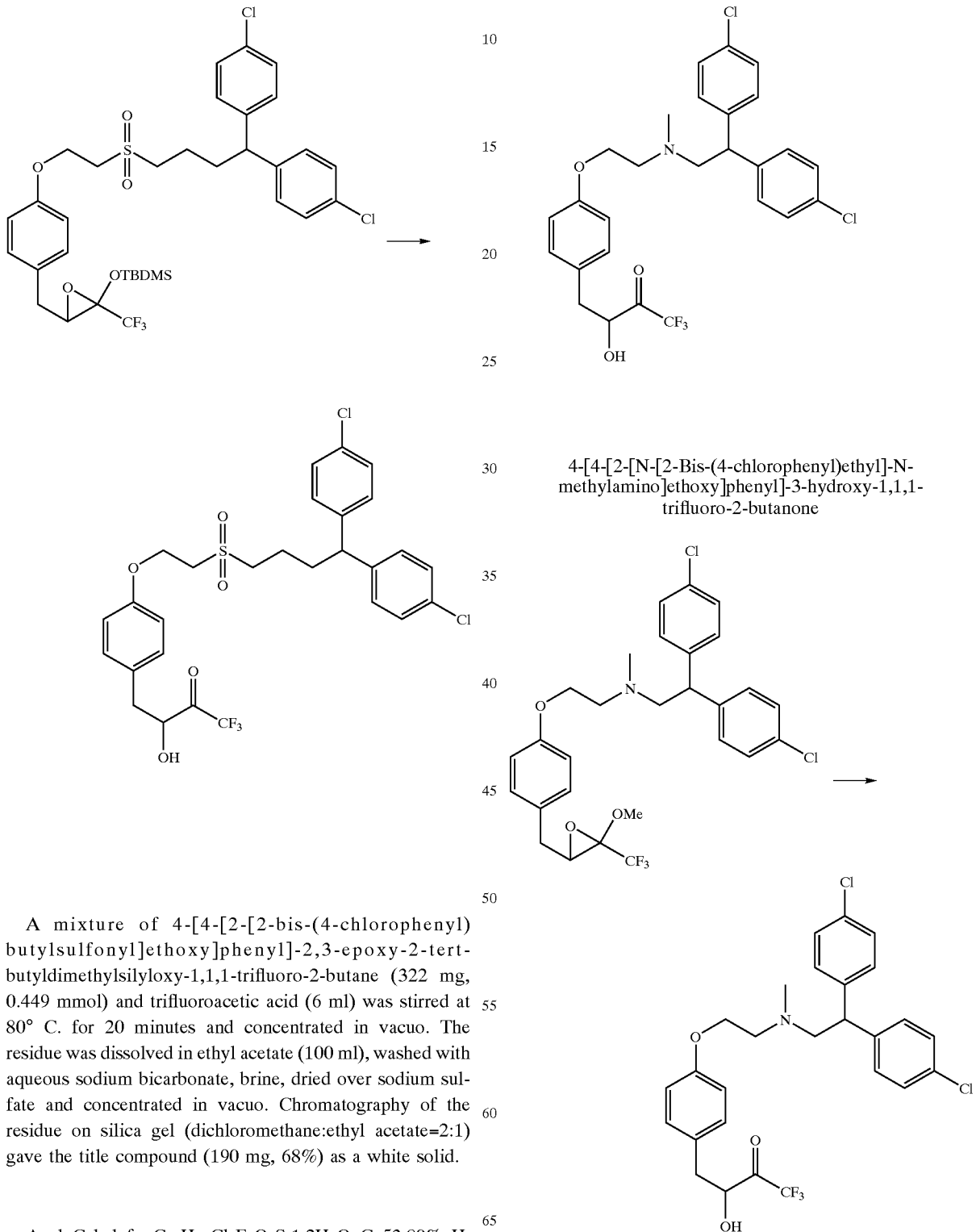

4-[4-[2-[N-[2-Bis-(4-chlorophenyl)ethyl]-N-
methylamino]ethoxy]phenyl]-3-hydroxy-1,1,1-
trifluoro-2-butanone A mixture of 4-[4-[2-[2-bis-(4-chlorophenyl)
butylsulfonyl]ethoxy]phenyl]-2,3-epoxy-2-tert-
butyldimethylsilyloxy-1,1,1-trifluoro-2-butane (322 mg,
0.449 mmol) and trifluoroacetic acid (6 ml) was stirred at
80° C. for 20 minutes and concentrated in vacuo. The
residue was dissolved in ethyl acetate (100 ml), washed with
aqueous sodium bicarbonate, brine, dried over sodium sul-
fate and concentrated in vacuo. Chromatography of the
residue on silica gel (dichloromethane:ethyl acetate=2:1)
gave the title compound (190 mg, 68%) as a white solid.

Anal. Calcd. for $C_{28}H_{27}Cl_2F_3O_5S \cdot 1.2H_2O$: C, 53.80%; H, 4.74%; Found: C, 53.51%; H, 4.62%.

A solution of 4-[4-[2-[N-[2-bis-(4-chlorophenyl)ethyl-N-methylamino]ethoxy]phenyl]-2,3-epoxy-2-methoxy-1,1,1-trifluoro-2-butane (100 mg, 0.18 mmol) in dimethylformamide (1 ml) and water (0.018 ml) was stirred at 80° C. for 6 hours, cooled to room temperature, diluted with ethyl acetate, washed with brine, dried over sodium sulfate and concentrated in vacuo. Chromatography of the residue on silica gel (hexane:ethyl acetate=3:1–2:1) gave the title material (50 mg, 51%) as a colorless oil.

Example 13

4-[4-[2-[Dodecanylthio]ethoxy]phenyl]-3-N-phenylamido-1,1,1-trifluoro-2-butanone

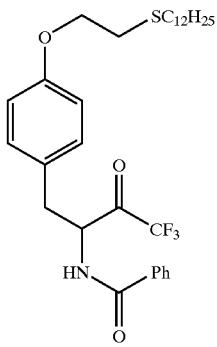

N-Benzoyl-O-dodecanylthioethyl-L-tyrosine ethyl ester

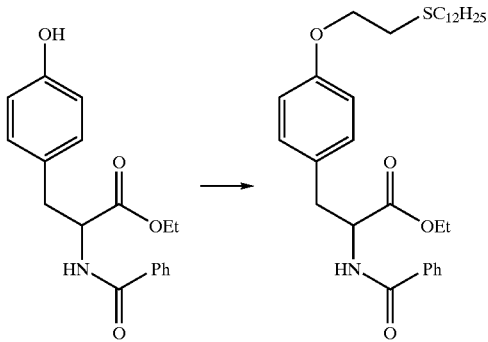

N-Benzoyl-L-tyrosine ethyl ester (4.0 g, 12.76 mmol) and dodecanylthioethanol [Patent Application WO 99/15129] (3.15 g, 12.76 mmol) were reacted as described in Example 2 for the preparation of 1-[2-{2-[bis(4-chlorophenyl)ethyl]methylamino}ethoxy]-4-bromo-benzene and gave the title material (4.6 g, 66%) as a white solid.

N-Benzoyl-O-dodecanylthioethyl-L-tyrosine

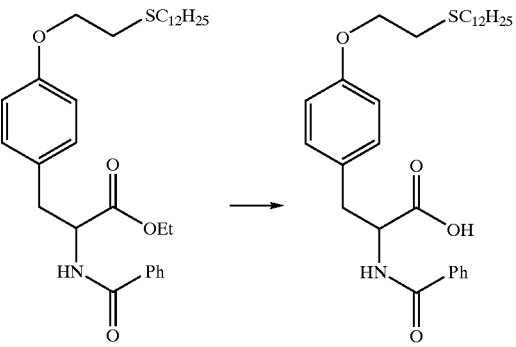

To a suspension of N-benzoyl-O-dodecanylthioethyl-L-tyrosine ethyl ester (4.2 g, 7.75 mmol) in ethanol (50 ml) was added a solution of lithium hydroxide (0.42 g, 10.08 mmol) in water (5 ml). The solution was stirred at room temperature for 4 hours and then diluted with ethyl acetate and washed with 1N hydrochloric acid and brine. The organic phase was dried over anhydrous magnesium sulfate, filtered and concentrated to give the title material (3.84 g, 96%) as a white solid.

4-[4-[2-[Dodecanylthio]ethoxy]phenyl]-3-N-phenylamido-1,1,1-trifluoro-2-butanone

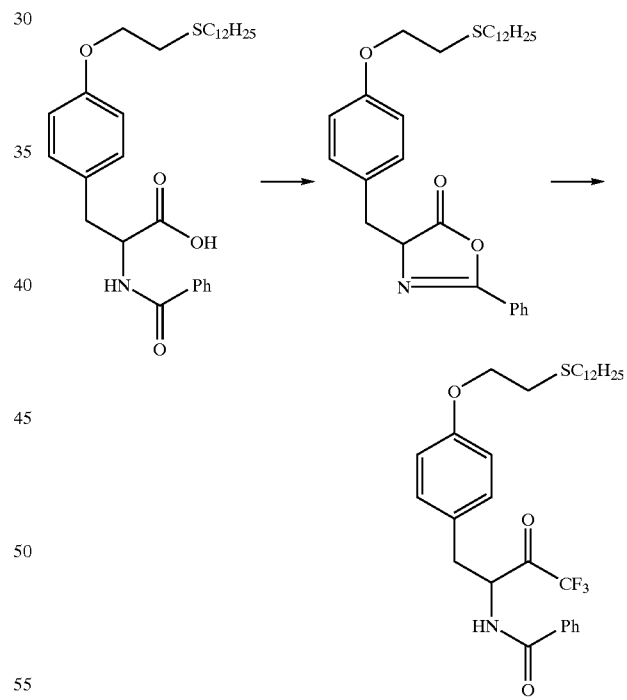

A suspension of N-benzoyl-O-dodecanylthioethyl-L-tyrosine (3.69 g, 7.18 mmol) in acetic anhydride (50 mL) was heated at 90° C. for 45 minutes. The mixture was then concentrated and diluted with ethyl acetate (250 ml). The organic phase was then washed with water (200 ml), saturated sodium bicarbonate (150 ml) and brine, dried over anhydrous magnesium sulfate, filtered and concentrated. The residue was crystallized in hexanes (2.8 g, 78%).

This solid (0.77 g, 1.55 mmol) was then treated with trifluoroacetic anhydride (5 ml) and the resulting suspension was diluted with tetrahydrofuran (4 ml) and heated to 60° C. for 24 hours. The mixture was concentrated and dried over vacuum. Oxalic acid (1.6 ml, 3.9 mmol) was then added and this mixture was stirred at room temperature for 24 hours. The mixture was concentrated and the excess of oxalic acid was precipitated with dichloromethane. The solution was filtered and concentrated. The residue was disoolved in ethyl acetate and washed with saturated sodium bicarbonate and brine, dried over anhydrous magnesium sulfate, filtered and concentrated. The residue was purified by silica gel chromatography (ethyl acetate/hexane 15% to 20%) to give the title material (0.566 g, 64%).

Anal. Calcd. for $C_{31}H_{42}NF_3O_3$. 0.8 $H_2O$: C, 64.18; H, 7.58; N, 2.41. Found: C, 64.16; H, 7.72; N, 2.47.

Example 14

4-[4-[2-[N-[2-Bis-(4chlorophenyl)ethyl]-N-methylamino]ethoxy]phenyl]-3-((3-carboxyphenyl)-2ethyl)-1,1,1-trifluoro-2-butanone, trifluoroacetic acid salt

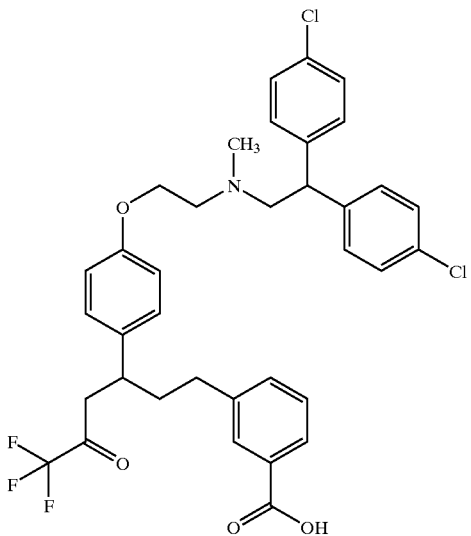

The title material was prepared as described in Example 2 except that methyl 3-oxo-5-(3-tert-butyloxycarbonyl-phenyl)-pentanoate was used instead of 1-methyl, 8-tert-butyl 3-oxo-1,8-octanedioate.

1H NMR (DMSO-d6, δ, ppm): 8.96 (1H, br s, —COOH), 7.77–7.25 and 6.90–6.88 (16H, m, aromatic H), 4.72 (1H, brt, —CH—(Cl—$C_6H_4$)$_2$), 4.39–4.28, 4.15–4.09, 3.92–3.88, 3.69–3.23, 3.11–3.07, 2.61–2.27 and 1.99–1.86 (13H, 7m, —O—(CH$_2$)$_2$—, —NCH$_2$—, —CO—CH$_2$—CH—(CH$_2$)$_2$—), 2.90 (3H, br d, —NCH$_3$—).

MS (ESI). 672.09 (M+H)$^+$; 690.10 (M+H$_2$O)$^+$.

We claim:

1. A compound of the formula

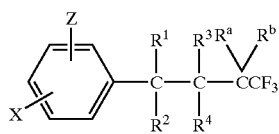

I wherein
$R^a$ and $R^b$ when taken together form an oxo (=O) group, or $R^a$ and $R^b$ are each independently hydrogen or OH;

X is H, CF$_3$, halogen, NR$^5$R$^6$, NH(CO)NR$^5$R$^6$, C(O)NR$^5$R$^6$, OH, OR$^7$, SH, S(O)$_n$R$^7$, C(O)OR$^8$, NH(CO)OR$^{10}$, C$_1$–C$_7$ alkyl, C$_2$–C$_7$ alkenyl, C$_2$–C$_7$ alkynyl or C$_3$–C$_7$ cycloalkyl, said alkyl, alkenyl, alkynyl or cycloalkyl group being optionally substituted by COOR$^8$, CN, C(O)NR$^5$R$^6$, PO$_3$R$^8$, SO$_3$R$^8$, heterocyclic, OH, OR$^7$, SH, S(O)$_n$R$^7$, NR$^5$R$^6$, NH(CO)NR$^5$R$^6$, NH(CO)OR$^{10}$, OC(O)OR$^{10}$, aryl or heteroaryl, said aryl or heteroaryl being optionally substituted by one or two groups independently selected from COOR$^8$, SO$_3$R$^8$, OCOR$^8$, PO$_3$R$^8$ or heterocyclic;

R$^1$ and R$^2$ are each independently H, OH, OR$^7$, SH, S(O)$_n$R$^7$, substituted C$_1$–C$_7$ alkyl, C$_2$–C$_7$ alkenyl, C$_2$–C$_7$ alkynyl or C$_3$–C$_7$ cycloalkyl, said alkyl, alkenyl, alkynyl or cycloalkyl group being substituted by COOR$^8$, CN, C(O)NR$^5$R$^6$, PO$_3$R$^8$, SO$_3$R$^8$, heterocyclic, OH, OR$^7$, SH, S(O)$_n$R$^7$, NR$^5$R$^6$, NH(CO)NR$^5$R$^6$, NH(CO)OR$^{10}$, OC(O)OR$^{10}$, aryl or heteroaryl, said aryl or heteroaryl group being optionally substituted by one or two groups independently selected from COOR$^8$, SO$_3$R$^8$, PO$_3$R$^8$ or heterocyclic;

R$^3$ and R$^4$ are each independently H, methylene, OH, OR$^7$, SH, S(O)$_n$R$^7$, NHCOR$^7$, COOR$^8$, C(O)NR$^5$R$^6$, substituted C$_1$–C$_7$ alkyl, C$_2$–C$_7$ alkenyl, C$_2$–C$_7$ alkynyl or C$_3$–C$_7$ cycloalkyl, said alkyl, alkenyl, alkynyl or cycloalkyl group being substituted by COOR$^8$, CN, C(O)NR$^5$R$^6$, PO$_3$R$^8$, SO$_3$R$^8$, heterocyclic, OH, OR$^7$, SH, S(O)$_n$R$^7$, NR$^5$R$^6$, NH(CO)NR$^5$R$^6$, NH(CO)OR$^{10}$, OC(O)OR$^{10}$, aryl or heteroaryl, said aryl or heteroaryl group being optionally substituted by one or two groups independently selected from COOR$^8$, SO$_3$R$^8$, PO$_3$R$^8$ or heterocyclic;

R$^5$ and R$^6$ are each independently H, C$_1$–C$_7$ alkyl, C$_2$–C$_7$ alkenyl, C$_2$–C$_7$ alkynyl, C$_3$–C$_7$ cycloalkyl, heterocyclic, aryl or heteroaryl, said alkyl, alkenyl, alkynyl, cycloalkyl, heterocyclic, aryl or heteroaryl group being optionally substituted with COOR$^8$, CN, OR$^8$, NR$^8$R$^9$, SO$_3$R$^8$, PO$_3$R$^8$, halogen, aryl or heteroaryl, said aryl or heteroaryl substituent being optionally substituted with one or two groups independently selected from COOR$^8$, SO$_3$R$^8$, PO$_3$R$^8$ or heterocyclic;

R$^7$ is C$_1$–C$_7$ alkyl or C$_3$–C$_7$ cycloalkyl, said alkyl or cycloalkyl group being optionally substituted by COOR$^8$, CN, C(O)NR$^5$R$^6$, PO$_3$R$^8$, SO$_3$R$^8$, heterocyclic, OR$^5$, SR$^5$, S(O)$_n$R$^{10}$, NR$^5$R$^6$, NH(CO)NR$^5$R$^6$, NH(CO)OR$^{10}$, C(O)$_2$OR$^{10}$, aryl or heteroaryl, said aryl or heteroaryl group being optionally substituted with one or two groups independently selected from COOR$^8$, SO$_3$R$^8$, PO$_3$R$^8$ or heterocyclic;

R$^8$ and R$^9$ are each independently H, C$_1$–C$_7$ alkyl or C$_3$–C$_7$ cycloalkyl;

R$^{10}$ is the same as R$^5$ and R$^6$ but is not H;

Z is Y—Z$^1$ in which

Y is —O—, —S(O)$_n$—,

or —CH$_2$;

n is 0, 1 or 2;

$R^c$ is H, —COCF$_3$, —COC$_6$H$_5$, —COO(C$_1$–C$_6$)alkyl,

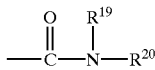

in which $R^{19}$ and $R^{20}$ are each independently H or (C$_1$–C$_6$)alkyl, (C$_1$–C$_{18}$)alkyl or (C$_1$–C$_{18}$)alkyl substituted by one or more of phenyl or phenyl substituted by 1–5 fluoro, 1–3 halo (other than fluoro), 1–3 (C$_1$–C$_6$)alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$)alkylamino, 1–3 di(C$_1$–C$_6$)alkylamino, 1–3 carboxyl, 1–3 —COO(C$_1$–C$_6$)alkyl, 1–3 —SO$_3$H, 1–3 —SO$_2$NHR$^{21}$ in which R$^{21}$ is hydrogen or (C$_1$–C$_6$)alkyl, or 1–3

in which $R^{19}$ and $R^{20}$ are as defined above; and $Z^1$ is

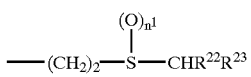  (a)

in which n$^1$ is 0, 1 or 2 and R$^{22}$ and R$^{23}$ are phenyl or phenyl substituted by 1–5 fluoro, 1–3 halo (other than fluoro), 1–3 (C$_1$–C$_6$)alkoxy, 1–3 (C$_1$–C$_6$)alkyl, 1–3 nitro, 1–3 cyano, 1–3 hydroxy, 1–3 trifluoromethyl, 1–3 (C$_1$–C$_6$)alkylthio, 1–3 amino, 1–3 (C$_1$–C$_6$)alkylamino, 1–3 di(C$_1$–C$_6$)alkylamino, 1–3 carboxy, 1–3 —COO(C$_1$–C$_6$)alkyl, 1–3 —SO$_3$H, 1–3 —SO$_2$NHR$^{21}$ in which R$^{21}$ is hydrogen or (C$_1$–C$_6$)alkyl, or

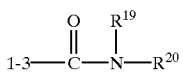

in which $R^{19}$ and $R^{20}$ are as defined above;

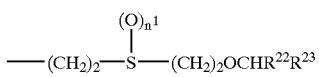  (b)

in which n$^1$ is 0, 1 or 2 and R$^{22}$ and R$^{23}$ are as defined above;

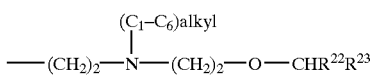  (c)

in which R$^{22}$ and R$^{23}$ are as defined above;

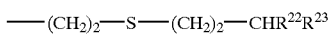  (d)

in which R$^{22}$ and R$^{23}$ are as defined above;

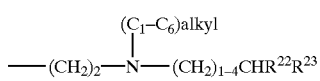  (e)

in which R$^{22}$ and R$^{23}$ are as defined above; or

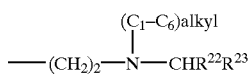  (f)

in which R$^{22}$ and R$^{23}$ are as defined above; or a pharmaceutically acceptable salt thereof with the proviso that at least one of R$^1$, R$^2$, R$^3$ and R$^4$ is other than hydrogen.

2. A compound according to claim 1 wherein Z is in the para-position.

3. A compound according to claim 1 or claim 2 wherein R$^1$ and R$^2$ are both hydrogen.

4. A compound according to claim 1 or claim 2 wherein R$^3$ and R$^4$ are both hydrogen.

5. A compound of claim 1 in which R$^1$ and R$^2$ are both hydrogen, R$^3$ is hydrogen, R$^4$ is —OH, —OCH$_3$, —O-i-propyl, —CH$_2$OH, —CH$_2$OCH$_2$OCH$_3$, —COOCH$_3$, —(CH$_2$)$_v$COO-t-butyl, —(CH$_2$)$_v$COOC$_2$H$_5$, —(CH$_2$)$_v$COOH,

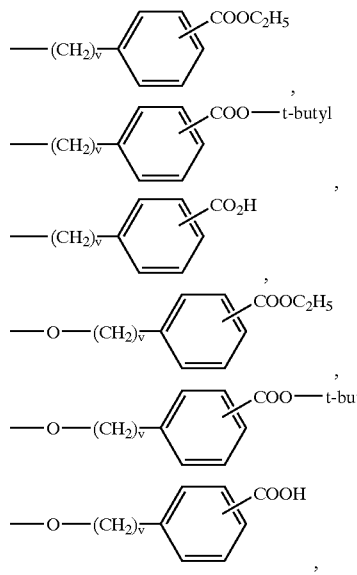

or

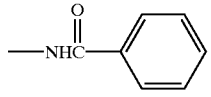

and v is 0 or an integer of from 1–6.

6. A compound of claim 1 in which R$^1$, R$^3$ and R$^4$ are hydrogen, R$^2$ is —S(CH$_2$)$_v$COO-t-butyl, —S—(CH$_2$)$_v$CO$_2$H, —(CH$_2$)$_v$COO-t-butyl, —(CH$_2$)$_v$CO$_2$H,

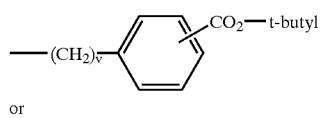

or

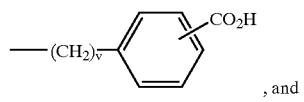
, and v is 0 or an integer of from 1–6.

7. A compound of any of claim 1 wherein X is H.

8. A pharmaceutical composition for the inhibition of cytosolic phospholipase $A_2$ comprising a therapeutically effective amount of a compound of claim 1 and a pharmaceutically acceptable carrier.

9. A method of inhibiting cytosolic phospholipase $A_2$ in a mammal in need thereof, comprising administering to said mammal a therapeutically effective amount of a compound of claim 1.

* * * * *